US012590961B2

(12) United States Patent
Oh et al.

(10) Patent No.: US 12,590,961 B2
(45) Date of Patent: Mar. 31, 2026

(54) QUANTUM DOT CONJUGATED VIRUS SPIKE PROTEIN FOR CELL-BASED BIO-SENSING SYSTEMS AND DRUG SCREENING

(71) Applicants: The Government of the United States of America, as represented by the Secretary of the Navy, Arlington, VA (US); The Government of the United States of America, as represented by the Secretary, Department of Health, Rockville, MD (US)

(72) Inventors: Eunkeu Oh, Alexandria, VA (US); Kimihiro Susumu, Alexandria, VA (US); Mason A. Wolak, Alexandria, VA (US); Kirill Gorshkov, Gaithersburg, MD (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 1102 days.

(21) Appl. No.: 17/389,645

(22) Filed: Jul. 30, 2021

(65) Prior Publication Data

US 2022/0034884 A1 Feb. 3, 2022

Related U.S. Application Data

(60) Provisional application No. 63/060,161, filed on Aug. 3, 2020.

(51) Int. Cl.
*G01N 33/58* (2006.01)
*G01N 33/569* (2006.01)

(52) U.S. Cl.
CPC ..... *G01N 33/56983* (2013.01); *G01N 33/588* (2013.01); *G01N 2333/165* (2013.01); *G01N 2500/02* (2013.01); *G01N 2500/10* (2013.01)

(58) Field of Classification Search
None
See application file for complete search history.

(56) References Cited

U.S. PATENT DOCUMENTS

| | | |
|---|---|---|
| 7,927,547 B2 | 4/2011 | Medintz et al. |
| 2009/0270269 A1 | 10/2009 | Kumar et al. |
| 2021/0302434 A1* | 9/2021 | Wang .................. C07K 14/165 |

OTHER PUBLICATIONS

Oh, et al. Journal of the American Chemical Society, 127, 3270-3271, doi:10.1021/a0433323 (Year: 2005).*
Cai, et al. (Science. Sep. 25, 2020;369(6511):1586-1592. doi: 10.1126/science.abd4251. Epub Jul. 21, 2020. PMID: 32694201. (Year: 2020).*
Oh, E. et al. Inhibition Assay of Biomolecules based on Fluorescence Resonance Energy Transfer (FRET) between Quantum Dots and Gold Nanoparticles. Journal of the American Chemical Society 127, 3270-3271, doi:10.1021/ia0433323 (2005).
Wang, H. et al. SARS coronavirus entry into host cells through a novel clathrin- and caveolae-independent endocytic pathway. Cell Research 18, 290-301, doi:10.1038/cr.2008.15 (2008.
Yang, N. & Shen, H.-M. Targeting the endocytic pathway and autophagy process as a novel therapeutic strategy in COVID-19. Int J Biol Sci 16, 1724 (2020).
International Search Report, dated Apr. 26, 2022, for counterpart application PCT/US2021/043846.
Written Opinion, daed Apr. 21, 2022, for counterpart application PCT/US2021/043846.
Oh, E. et al. Inhibition Assay of Biomolecules based on Fluorescnece Resonance Energy Transfer (FRET) betweeb Quantum Dots and Gold Nanoparticles. Journal of the American Chemical Society 127, 3270-3271 (2005).
Lan, J. et al., "Structure of the SARS-CoV-2 spike receptor-binding bound to th ACE2 receptor." Nature, Mar. 30, 2020, vol. 581, pp. 215-220.
NCBI, GenBank Accession No. 6W41_C, "Chain C, Spike glycoprotein receptor binding domain." Mar. 26, 2020.
Kuo, Kai-Wei, et al. "Cell Uptake and Intracellular Visualization Using Quantum Dots or Nuclear Localization Signal-Modified Quantum Dots with Gold Nanoparticles as Quenchers." J. Nanosci. Nanotechnol. 2010, vol. 10, No. 7, pp. 417-4177.

* cited by examiner

*Primary Examiner* — Michael Allen
*Assistant Examiner* — Jeffrey Mark Sifford
(74) *Attorney, Agent, or Firm* — US Naval Research Laboratory; Fariborz Moazzam

(57) ABSTRACT

Quantum dots conjugated to SARS-CoV-2 Spike protein receptor binding domain (RBD) interact with gold nanoparticles bound to angiotensin converting enzyme 2 (ACE2) and thus undergo energy transfer. This energy transfer indicates RBD/ACE binding and can be used to assay for inhibitors thereof. Moreover, these labeled quantum dots were found to undergo endocytosis in cells expressing ACE2.

5 Claims, 24 Drawing Sheets

Specification includes a Sequence Listing.

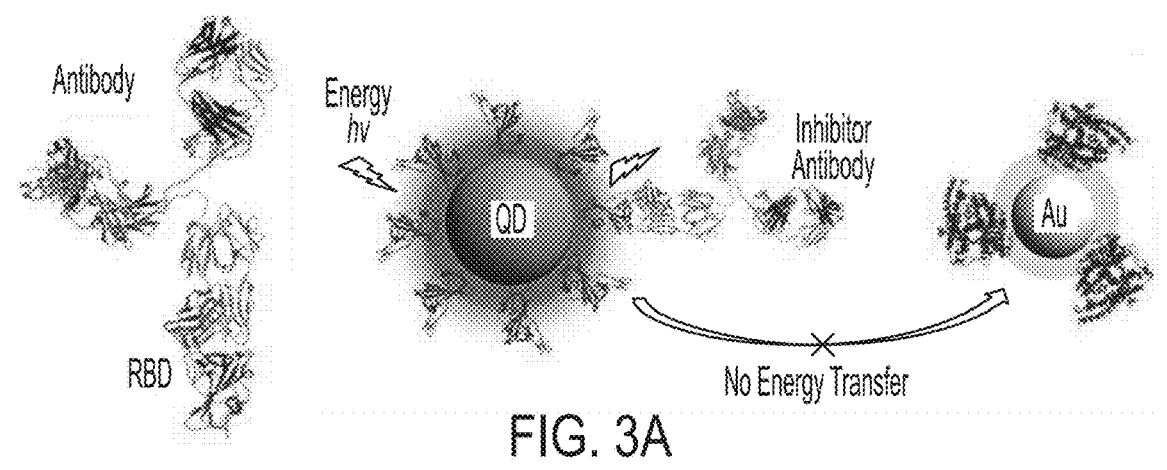
FIG. 3A
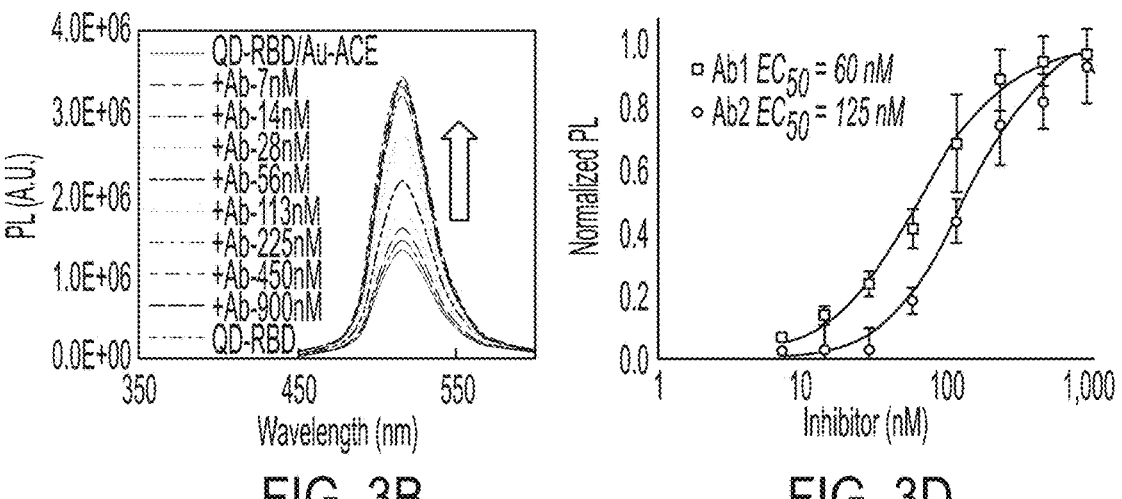
FIG. 3B
FIG. 3D
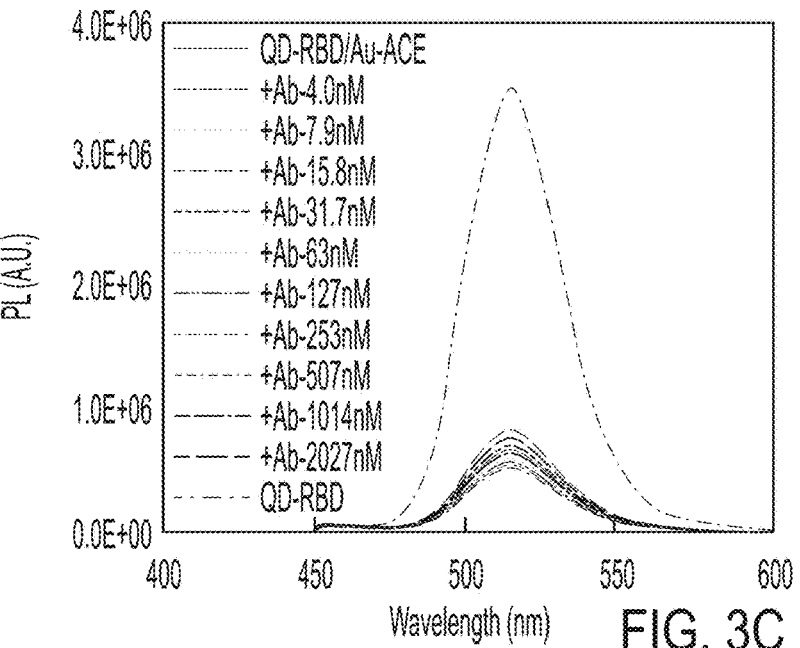
FIG. 3C

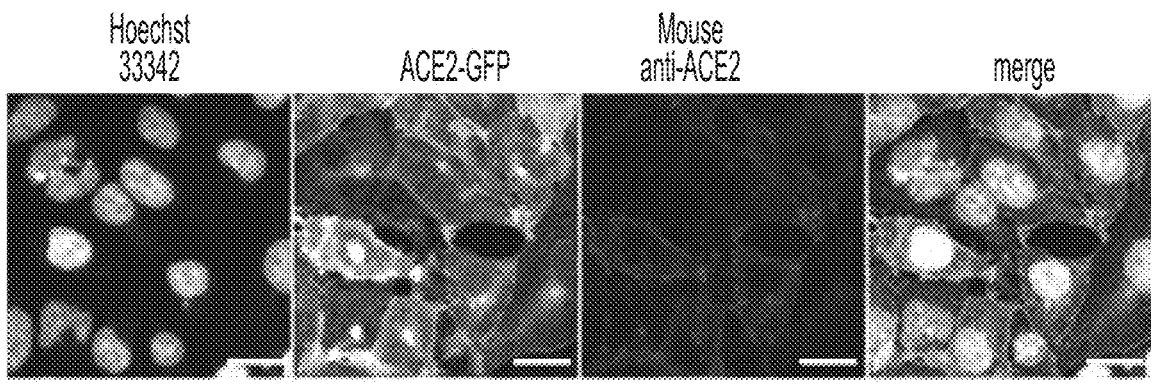
FIG. 4C
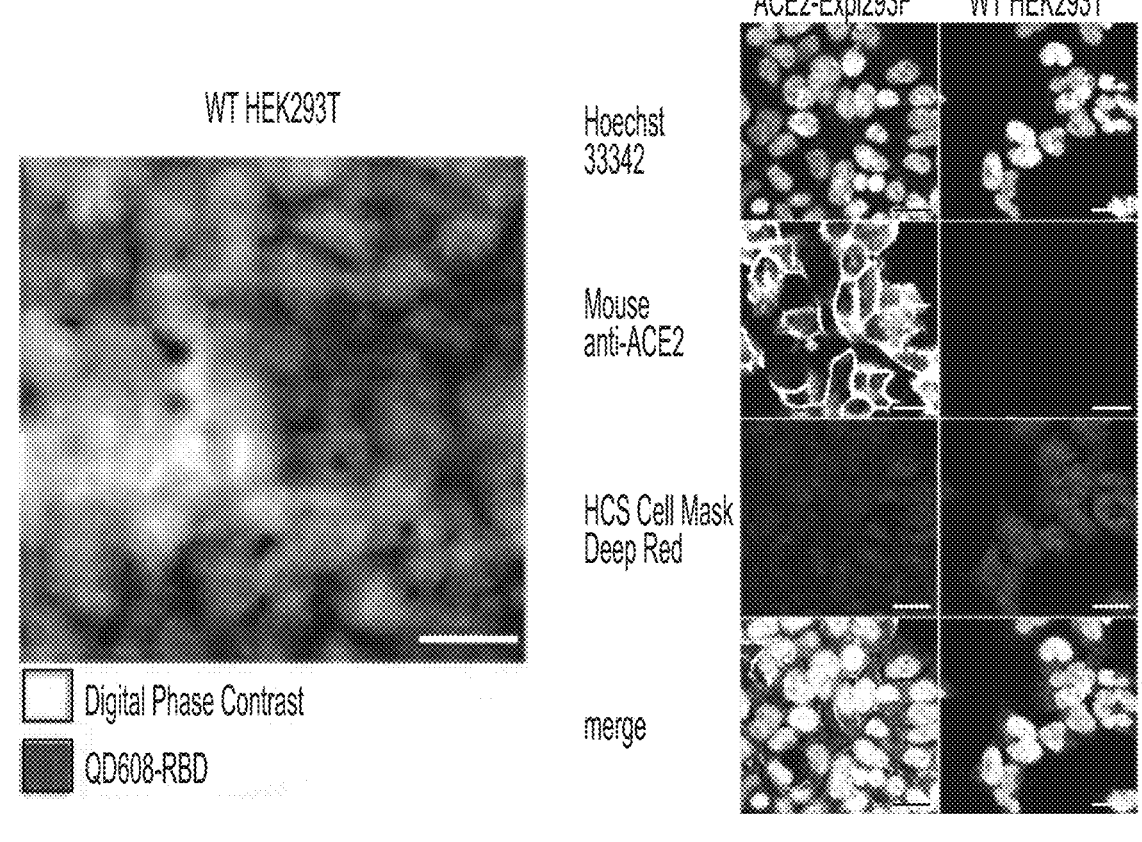
FIG. 4D                    FIG. 4E

| | ACE2 -GFP | QD608 -RBD |
|---|---|---|
| Ab1 EC50(nM) | 5.58 | 6.63 |
| Ab2 EC50(nM) | 11.2 | 20.9 |
| ACE2-Fc EC50(nM) | 95 | 102 |

| Rel. Spot. Int. | 10% FBS | 5% FBS | 2.5% FBS | 1.25% FBS | 0% FBS |
|---|---|---|---|---|---|
| S/B | 1157 | 255 | 33 | 67 | 105 |
| CV% | 24.2 | 6.3 | 6.9 | 5.1 | 7.1 |
| Z-factor | 0.27 | 0.76 | 0.34 | 0.62 | 0.67 |

| Spot Count | 10% FBS | 5% FBS | 2.5% FBS | 1.25% FBS | 0% FBS |
|---|---|---|---|---|---|
| S/B | 300 | 147 | 34 | 60 | 62 |
| CV% | 27 | 20 | 17 | 13 | 16 |
| Z-factor | 0.17 | 0.34 | 0.09 | 0.42 | 0.40 |

| Spot Area (μm²) | 10% FBS | 5% FBS | 2.5% FBS | 1.25% FBS | 0% FBS |
|---|---|---|---|---|---|
| S/B | 460 | 188 | 35 | 73 | 88 |
| CV% | 24 | 19 | 16 | 12 | 13 |
| Z-factor | 0.26 | 0.38 | 0.09 | 0.47 | 0.49 |

FIG. 7B

QUANTUM DOT CONJUGATED VIRUS SPIKE PROTEIN FOR CELL-BASED BIO-SENSING SYSTEMS AND DRUG SCREENING

CROSS-REFERENCE TO RELATED APPLICATIONS

This application claims the benefit of U.S. Provisional Application 63/060,161 filed on Aug. 3, 2020, the entirety of which is incorporated herein by reference.

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, D.C. 20375, USA; +1.202.767.7230; techtran@nrl.navy.mil, referencing NC 113,397.

BACKGROUND

The severe acute respiratory syndrome coronavirus of 2019 (SARS-CoV-2) is known to cause the coronavirus disease of 2019 (COVID-19)'. The global SARS-CoV-2 viral pandemic has resulted in many millions of COVID-19 cases around the world: as of Jul. 29, 2021, there have been over 195 million cases globally and over 4,180,000 confirmed deaths[2]. This deadly virus has prompted a mobilization of research activity on an unprecedented scale. The field of drug discovery and development for COVID-19 antivirals requires tools and reagents to study the viral mechanisms of infection in order to identify targets for therapeutic intervention.

The first step of SARS-CoV-2 infection involves the attachment of the large trimeric Spike glycoprotein to the cell. In particular, Spike's S1 subunit receptor binding domain (RBD) binds to the host cell's angiotensin converting enzyme 2 (ACE2), a transmembrane enzyme expressed on the plasma membrane surface[3,4]. Because the Spike and its binding to the ACE2 receptor plays such a vital role in initiating viral infection, the development of probes to study this interaction are needed by researchers engaged in SARS-CoV-2 drug discovery efforts[5].

Tools and reagents developed to combat SARS-CoV-2 may be useful in work relating to other viruses.

BRIEF SUMMARY

In one embodiment, a method of assaying inhibitors of spike protein binding includes providing a quantum dot labeled with a protein comprising SARS-CoV-2 Spike protein receptor binding domain (RBD); contacting the quantum dot (QD) with a nanoparticle conjugated to angiotensin converting enzyme 2 (ACE2) in the presence of a possible inhibitor of binding between the RBD and ACE2; and measuring energy transfer between the QD and the nanoparticle, wherein the energy transfer indicates binding between the RBD and ACE2 and thereby possible inhibition thereof.

In a further embodiment, a method of assaying inhibitors of viral binding includes providing a QD labeled with a viral surface protein; contacting, in the presence of a possible inhibitor, the QD with a metallic nanoparticle configured as an energy transfer partner of the QD, wherein the metallic nanoparticle is conjugated to a binding partner of the viral surface protein (for example, a viral target found in human cells); and measuring energy transfer between the QD and the metallic nanoparticle, wherein the energy transfer indicates binding between the viral surface protein and the binding partner thereof and thereby possible inhibition.

In yet another embodiment, a method of analyzing spike protein activity includes providing cells expressing angiotensin converting enzyme 2 (ACE2); contacting the cells with a QD labeled with a protein comprising SARS-CoV-2 Spike protein receptor binding domain (RBD) optionally in the presence of a possible inhibitor of binding between the RBD and ACE2; and observing the cells for possible endocytosis of the QD.

In a still further embodiment, a method of assaying for cell-based receptors binding to a viral protein includes providing cells expressing a possible binding partner of the viral protein; contacting the cells with a quantum dot labeled with the viral protein and optionally in the presence of a possible inhibitor of binding between the viral protein and the biding partner of viral protein; and observing the cells for possible endocytosis of the quantum dots.

In various aspects of any of these embodiments, the protein comprising RBD is a Spike protein trimer.

In further aspects, the measured energy transfer can be quenching of QD fluorescence via proximity to the nanoparticle. Energy transfer can be measured using techniques including but not limited to microscopy, spectrophotometry, high-throughput screening, computer-aided analysis, and combinations thereof.

BRIEF DESCRIPTION OF THE DRAWINGS

FIG. 1A is a schematic diagram of the biochemical assay using energy transfer from QD-RBD to AuNP-ACE2 (top) and the cellular assay using QD-RBD interaction with ACE2 (with or without modification at the end of C-terminal with green fluorescent protein, also termed GFP) on the cell membrane (second image from top). The next image shows the binding formation of ACE2 and RBD (third from top, with estimated size marked in Å) and the chemical structure of surface ligands for both QDs and AuNPs (bottom). FIG. 1B provides transmission electron micrograph (TEM) images of nanoparticles (NPs). Top: As synthesized $QD_{608}$ (10.1±0.94 nm) and $QD_{514}$ (8.4±0.84 nm). Bottom: $QD_{608}$-RBD (10.1±0.89 nm), AuNP-ACE2 (5.8±0.8 nm). FIGS. 1C and 1D show absorption and fluorescence spectra of CL4-coated $QD_{608}$ and of CL4-coated $QD_{514}$, respectively, each in water.

FIG. 2A shows photoluminescence (PL) changes of $QD_{514}$-RBD mixed with different ratios of AuNP-ACE2/$QD_{514}$-RBD; from 0 (noted as 'QD') to 10 (noted as 'QD+10Au'). FIG. 2B displays energy transfer efficiency as a function of the ratio of AuNP-ACE2 per $QD_{514}$-RBD; the experimental plots and three different theoretical models. FIG. 2C shows TEM images of clustered AuNPs due to the binding between AuNP-ACE2 and $QD_{514}$-RBD (ratio=8) (top) and TEM images of freely dispersed AuNP and $QD_{514}$ without ACE2 or RBD which shows no clustering between nanoparticles (bottom).

FIGS. 3A-3D show results of NPs-based inhibition assays. FIG. 3A left depicts the binding structure of neutralization antibody (top) against SARS 2-RBD with RBD (bottom) while the right side is a schematic diagram of inhibition assay depicting blocking of the interaction between RBD and ACE2 and the resulting inhibition of energy transfer from QD to AuNP. FIG. 3B is data showing PL recovery of $QD_{514}$-RBD in the presence of Ab1 neutralizing antibody against Spike S1 protein. FIG. 3C shows results from an inhibition test using anti-Spike antibody without neutralizing ability, showing almost no PL recovery of $QD_{514}$-RBD. FIG. 3D shows the calculated $EC_{50}$ of neutralizing antibodies Ab1 and Ab2 was 60 nM and 125 nM with $R^2 > 99\%$, respectively.

FIGS. 4A-4E show that quantum dot-conjugated Spike-RBD domain induces translocation of ACE2 and internalizes into cells. FIG. 4A is a representative image montage of ACE2-GFP HEK293T clone 2 treated with 100 nM $QD_{514}$-RBD and $QD_{608}$-RBD. Digital phase contrast was used during live-cell imaging to identify cell somas. FIG. 4B shows high-content analysis averages of Spot Count for $QD_{514}$-RBD and $QD_{608}$-RBD and ACE2-GFP. N=>400 cells from duplicate wells. FIG. 4C is a representative image montage of immunofluorescence staining for ACE2 in ACE2-GFP HEK293T cells. Cells were stained with Hoechst 33342 for nuclei, mouse anti-ACE2 antibody, and HCS Cell Mask Deep Red for whole cell fill. N=9 fields each from 3 triplicate wells. In FIG. 4D, WT HEK293T cells were treated with 100 nM $QD_{608}$-RBD. Digital phase contrast in cyan and $QD_{608}$-RBD in magenta. FIG. 4E is a representative image montage of ACE2-Expi293F and WT-HEK293T cells stained with Hoechst 33342, mouse anti-ACE2 antibody, and HCS Cell Mask Deep Red. N=3 triplicate wells. Optimem I alone used as control. N=10 fields from a single well. Scale bar, 25 μm.

FIGS. 5A-5F show $QD_{608}$-RBD induced translocation of ACE2-GFP is blocked using endocytosis inhibitor Dyngo-4a. FIG. 5A is a representative image montage of ACE2-GFP signal in HEK293T clone 2 treated with 10 nM $QD_{608}$-RBD. ACE2-GFP is represented by a yellow look-up table. FIG. 5B depicts the same cells from FIG. 5A showing the $QD_{608}$-RBD signal. Control cells were incubated with Optimem I alone. Dyngo-4a treated cells were first preincubated with compound for 15 min. Time course spans 3 h and imaging began immediately after treating cells with $QD_{608}$-RBD. Images were captured using a 63× objective. Scale bar, 25 μm. FIG. 5C is a high-content analysis averages of Spot Count for ACE2-GFP and $QD_{608}$-RBD. Curves fit using non-linear regression. N≥1100 cells from 4 fields each from 10 wells per condition, representative of three experiments. Error bars indicate S.D. FIG. 5D is a single particle imaging of QD (left) and overlay with tracks (right) in ACE2-GFP HEK293T cells. Scale bar, 5 μm. In FIG. 5E, the ensemble mean of all mean square displacements (MSD) (1562 tracks) shown as a solid line. The grayed area represents the weighted standard deviation over all MSD curves. FIG. 5F shows the distribution of one-step jump distances with fitted curve (solid line) of QDs in the ACE2-GFP HEK293T cells.

FIG. 6A is a representative image montage of ACE2-GFP HEK293T clone 2 treated with 10 nM $QD_{608}$-RBD. Digital phase contrast was used during live-cell imaging to identify cell bodies. Cells were treated with neutralizing antibodies Ab1 and Ab2 starting at 100 nM. FIG. 6B shows high-content analysis averages for ACE2-GFP and $QD_{608}$-RBD Relative Spot Intensity, Spot Count, and Spot Area (μm²) treated with neutralizing antibodies. FIG. 6C is a representative image montage of ACE2-GFP HEK293T clone 2 treated with 10 nM $QD_{608}$-RBD. Digital phase contrast was used during live-cell imaging to identify cell bodies. Cells were treated with ACE2-Fc starting at 1.5 μM. FIG. 6D is a high-content analysis averages for ACE2-GFP and $QD_{608}$-RBD Relative Spot Intensity, Spot Count, and Spot Area (μm²) treated with ACE2-Fc. N≥2000 cells from triplicate wells each from three independent experiments. Error bars indicate S.D. FIG. 6E provides a table showing the $EC_{50}$ values for Ab1, Ab2, and ACE2-Fc based on Spot Count from FIGS. 6B and 6D. Images were captured using a 40× objective. FIG. 6F is an illustration of $QD_{608}$-RBD internalization via receptor-mediated endocytosis and the inhibition using Ab1, Ab2, and ACE2-Fc.

FIGS. 7A and 7B show how this technique can be employed for high-throughput screening. FIG. 7A shows Relative Spot Intensity of $QD_{608}$-RBD in a 1536-well plate with ACE2-GFP HEK293T at different concentrations of fetal bovine serum (FBS) using a ThermoFisher Scientific Multidrop Combi reagent dispenser. The data presented in FIG. 7B reveal that 5% FBS produced good statistics for $QD_{608}$-RBD Relative Spot Intensity. In these figures, CV=coefficient of variation; standard deviation/average; S/B=signal to background; signal from QD-treated cells/ signal from untreated cells; Z-factor=assay robustness for screening; and Z-factor=1−3((SD pos. ctrl+SD neg. ctrl)/ (abs(mean pos. ctrl−mean neg. cap)).

FIG. 8B is a representative image montage of ACE2-GFP HEK293T clone 2 treated with 10 nM $QD_{608}$-Spike. Digital phase contrast was used during live-cell imaging to identify cell somas.

FIGS. 8C and 8D shows high-content analysis averages of Spot Count for various types of $QD_{608}$-Spike and ACE2-GFP with different types of Spike trimer. N=>400 cells from duplicate wells. Scale bar, 25 μm.

FIG. 8E is a representative image montage of ACE2-GFP HEK293T clone 2 treated with 10 nM $QD_{608}$-Spike. Digital phase contrast was used during live-cell imaging to identify cell bodies. Cells were treated with neutralizing antibodies Ab1 and Ab2 at 30 μg/mL. FIGS. 8F and 8G are high-content analysis averages for ACE2-GFP and various types $QD_{608}$-Spike Relative Spot Count (normalized to QD conjugated with WT of Spike) treated with neutralizing antibodies. FIG. 8H is a representative image montage of ACE2-GFP HEK293T clone 2 treated with 10 nM $QD_{608}$-Spike. Digital phase contrast was used during live-cell imaging to identify cell bodies. Cells were treated with ACE2-Fc starting at 1.2 μM. FIG. 8I is a high-content analysis of ACE2-GFP and $QD_{608}$-Spike Relative Spot Count showing the Efficacy (%) of ACE2-Fc. N≥2000 cells from triplicate wells. Error bars indicate S.D. Data normalized to QD only (100% efficacy) and QD-Spike (0%) treated cells. Images were acquired using a 40× objective.

DETAILED DESCRIPTION

Definitions

Figure 1A:
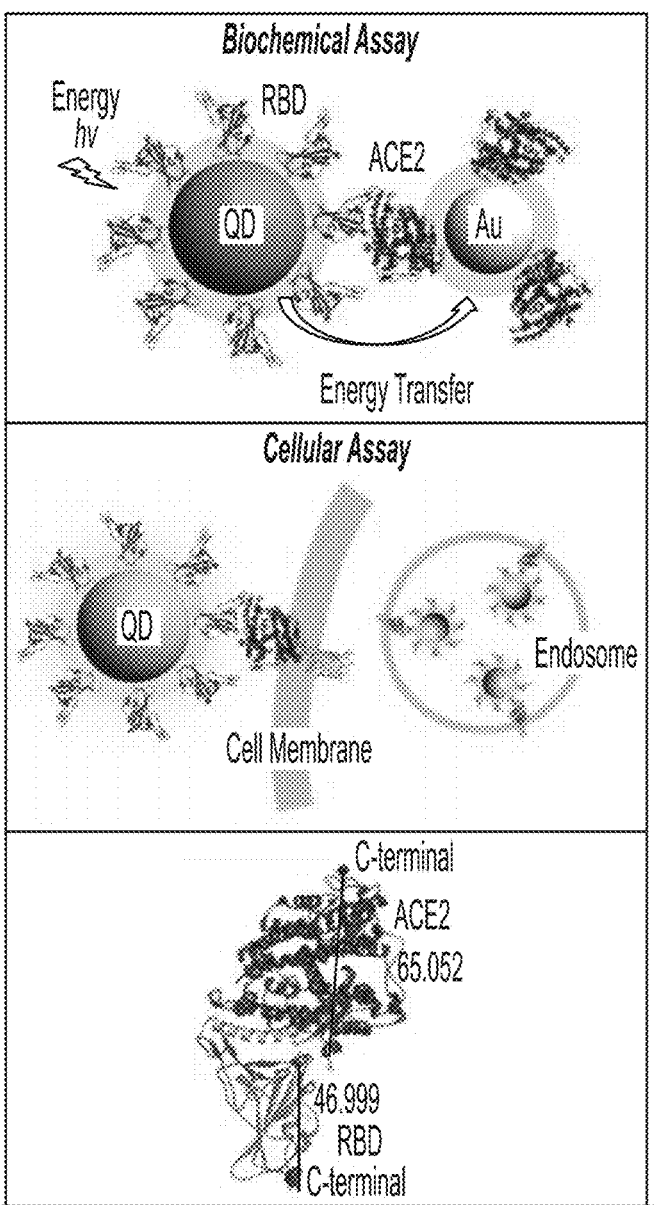
FIGS. 1A-1D depict assay design and physical properties of nanoparticles.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

SARS-CoV-2 begins cellular infection via binding of the spike protein's receptor binding domain to the host cell's ACE2 receptor on the plasma membrane. Described herein is a versatile imaging probe using recombinant Spike receptor binding domain conjugated to fluorescent quantum dots (QDs) useful to detect potential inhibitors of this binding, and thus possible therapeutics. This probe is capable of engaging in energy transfer quenching with ACE2-conjugated gold nanoparticles. Neutralizing antibodies and recombinant human ACE2 blocked quenching, demonstrating a specific binding interaction. In cells transfected with ACE2-GFP, there was immediate binding of the probe on the cell surface followed by endocytosis. Neutralizing antibodies and ACE2-Fc fully prevented binding and endocytosis with low nanomolar potency. This QD nanoparticle probe can be used to identify and validate inhibitors of the SARS-CoV-2 Spike and ACE2 receptor binding in human cells. This foundational work opens the door for facile, rapid, and high-throughput cell-based screening of inhibitors for coronavirus Spike-mediated cell recognition and entry.

The nanoparticle probes described herein, comprising Spike subunits conjugated to quantum dots (QD), can (1) monitor Spike/ACE2 binding, (2) measure the cellular spatiotemporal dynamics of Spike/ACE2 binding and internalization, and (3) scale for high-throughput drug screening. While the examples used QDs of about 7-10 nm in size, making them smaller than an average SARS-CoV-2 virion[3], nonetheless these QD probes approximate the virus particle shape and mimic its interactions with human cells. It is also possible to use QDs of larger size (for example, about 20-30 nm) to better approximate the size of the virion. Notwithstanding their size, the constructs of Spike subunits conjugated to QDs can be considered as model 'pseudo-virions.' Thus, they facilitate the study of Spike protein-protein interactions and spatiotemporal dynamics.

A QD features well-tailored emission characteristics and the ability to serve as a central anchor for multiple spike proteins. QDs have garnered significant attention over conventional organic fluorophores due to their unique photophysical properties that include (1) size and composition dependent tuning of fluorescence spectra, (2) broad excitation spectra, (3) high molar absorptivity, (4) high fluorescence quantum yield (QY) and (5) photochemical stability[6-9]. Because QDs are photostable, relatively small in size, and their surfaces can be easily functionalized with a series of biological molecules, there is great interest in developing QD-based Forster resonance energy transfer (FRET) biosensing systems with various energy transfer partners. One of the best energy acceptors for QDs are gold nanoparticles (AuNPs), due to their large absorptivity in the visible electromagnetic spectrum[10-13].

As detailed below, the utility of fluorescent QDs, AuNPs, and ACE2-green fluorescent protein tagged (ACE2-GFP) cells have been combined to allow for facile monitoring of Spike-ACE2 interactions. Here, conjugates of Spike subunits bound to a central QD are referred to as "QD-[subunit]" (e.g. QD-RBD) and ACE2 receptors bound to a central AuNP as "AuNP-ACE2". An energy transfer system allows monitoring of Spike-ACE2 binding in vitro where QD fluorescence is quenched by the nearby AuNP upon binding. This quenching can be disrupted by unlabeled ACE2 or neutralizing SARS-CoV-2 antibodies competing with or blocking QD-Spike binding to ACE2-AuNP, respectively. The QD-RBD was further used with ACE2-GFP to directly image Spike-ACE2 endocytosis [endo(RBD:ACE2)] using real-time confocal microscopy and high-resolution single molecule tracking in living cells.

Examples

Nanoparticle-Based Assay Design

An energy transfer system was sought to monitor the interaction between Spike and ACE2, using QD-RBD (Green $QD_{514}$, fluorescence maximum at 514 nm) and AuNP-ACE2 that quenches QD fluorescence with close proximity facilitated by RBD-ACE2 binding[10]. Photoluminescence (PL) quenching of QDs is dependent on the binding affinity, conjugation ratio, and the integral overlap of donor-acceptor pair (details in Methods). For cellular assays, QD-RBD and ACE2-GFP internalization was monitored using orange-emitting QD ($QD_{608}$, fluorescence maximum at 608 nm) and GFP signal (fluorescence maximum at 509 nm). The pseudo-virion QD-RBD was used to study RBD:ACE2 internalization and its inhibition by recombinant ACE2 with Fc region of the human immunoglobulin IgG1 (ACE2-Fc) or neutralizing antibodies.

Figure 1B:
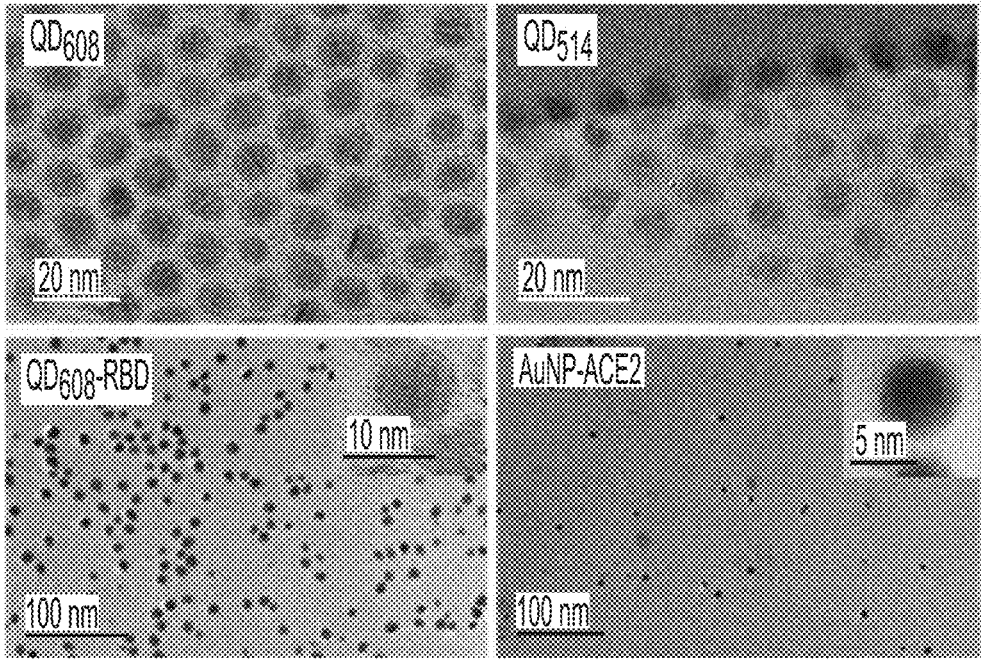
Figure 1C:
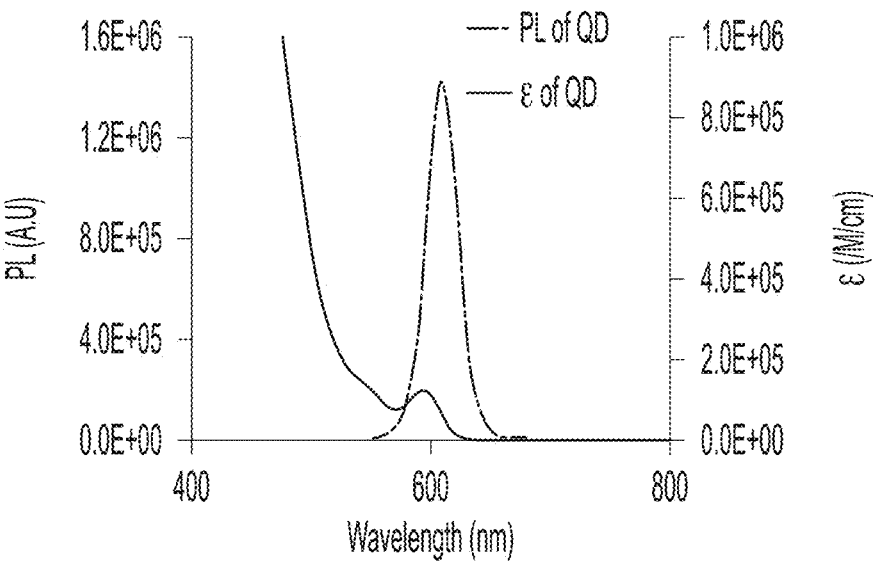
Figure 1D:
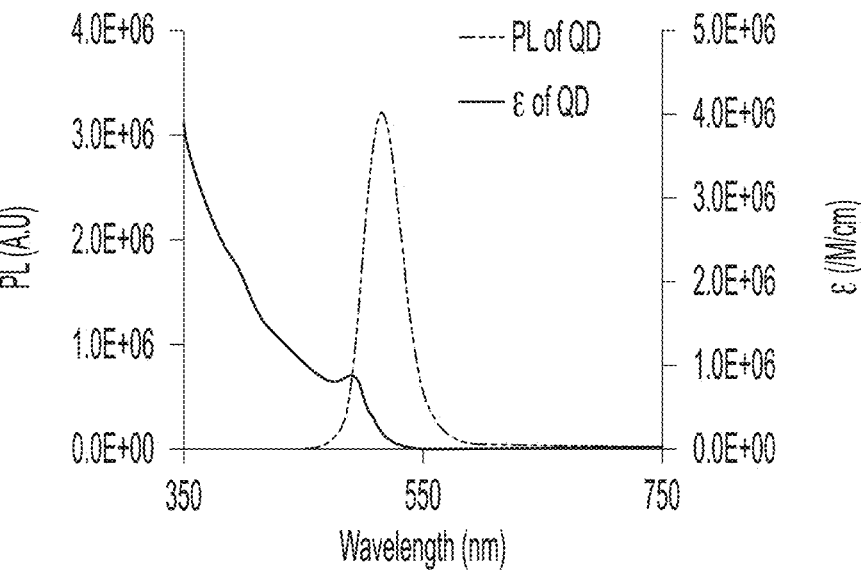

For this, QD surfaces were modified with compact ligands (CL4) and AuNPs with dihydrolipoic acid (DHLA) mixed with nitrilotriacetic acid-modified DHLA (DHLA-PEG-NTA, DHLA-NTA)[12] (FIG. 1A). QDs have narrow emission spectra, and measurements using transmission electron microscopy (TEM) determined their diameter to be 10.4 nm for orange $QD_{608}$ and 8.4 nm for green $QD_{514}$ (FIG. 1B). TEM also confirmed that the QD sizes and shapes were not affected by ligand exchange nor protein conjugation and that the QDs were well dispersed (Table 1). AuNP exhibited a surface resonance peak at 520 nm and the size was 5.6 nm as measured by TEM (FIG. 1B). The hydrodynamic size of NPs in an aqueous solution was 13.2 nm and 16.6 nm for $QD_{514}$-CL4 and $QD_{608}$-CL4, respectively, and 15.6 nm for AuNP-NTA, which were larger than the TEM core sizes due to the hydration layer and ligand layer[18] (Table 1). Next, histidine-tagged RBD (RBD-His) and histidine-tagged ACE2 (ACE2-His) were conjugated to NPs via coordination directly to the QD surface or NTA on the AuNP surface (details in Methods). The tested RBD comprised SEQ ID NO: 1. After conjugation, the QD hydrodynamic size was increased by 7 nm with RBD (molar ratio of RBD/QD=8, hereafter), 15 nm with S1 (S1/QD=4) and 40 nm with S1+S2 (S1+S2/QD=3), which were reasonable increases according to the protein sizes (Table 1). Similarly, the hydrodynamic size of AuNP was increased by 6 nm with ACE2 conjugation (ACE2/AuNP=3). Gel electrophoresis revealed decreases in the mobility shifts as the conjugation ratio of RBD to QD increased from 0 to 16, and confirmed efficient conjugation of RBD-His to QD as well as ACE2-His to AuNP.

RBD:AuNP-ACE2 complex captured clustering of QD and AuNP (FIG. 2C) and the decreased distance between NPs (FIG. 2B) further corroborated specific RBD-ACE2 binding, while control samples without protein conjugates did not show any clustering. However, the inner-screening effect of AuNP, the electron transfer, or the electrostatic interaction cannot be completely excluded as additional contributions to quenching[21,22]. Regardless of the fit to the models, the observed PL quenching indicated the binding between the

TABLE 1

| | | Characteristics of Nanoparticles and Nanoparticle-protein conjugates | | | |
|---|---|---|---|---|---|
| | Emission Peak | Extinction Coefficient (/M/cm) | TEM size (nm) | Hydrodynamic Size (Intensity Mode) | Hydrodynamic Size (Number Mode) |
| $QD_{608}$-CL4 | 608 nm | $1.2 \times 10^5$ @592 | 10.0 ± 0.93 | 16.6 ± 0.6 | 12.2 ± 0.1 |
| $QD_{608}$-RBD | (FWHM~26 nm) | | 10.1 ± 0.89 | 23.8 ± 2.4 | 19.9 ± 0.9 |
| $QD_{608}$-S1 | (QY~30%) | | — | 28.2 ± 1.1 | 23.4 ± 0.7 |
| $QD_{608}$-S1 + S2 | | | — | 56.1 ± 0.9 | 53.1 ± 1.6 |
| $QD_{514}$-CL4 | 514 nm | $8.9 \times 10^5$ @488 | 8.4 ± 0.84 | 13.2 ± 0.5 | 10.8 ± 1.6 |
| $QD_{514}$-RBD | (FWHM~34 nm) | | 8.2 ± 0.72 | 21.8 ± 2.3 | 17.0 ± 1.3 |
| | (QY~40%) | | | | |
| AuNP-NTA | — | $1.4 \times 10^7$ @520 | 5.6 ± 0.7 | 15.6 ± 0.5 | 11.8 ± 0.4 |
| AuNP-ACE2 | | | 5.8 ± 0.8 | 21.7 ± 0.7 | 17.4 ± 1.7 |

Mean ± S.D.

NP-Based Energy Transfer Biosensor for RBD-ACE2 Binding

Figure 2A:
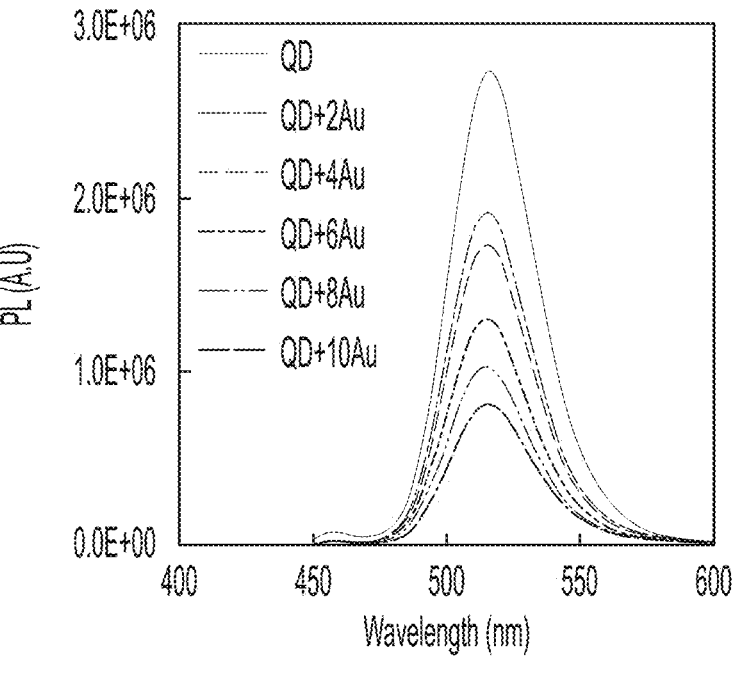
FIGS. 2A-2C provide results of energy transfer quenching assays using QD-RBD and AuNP-ACE2.
Figure 2B:
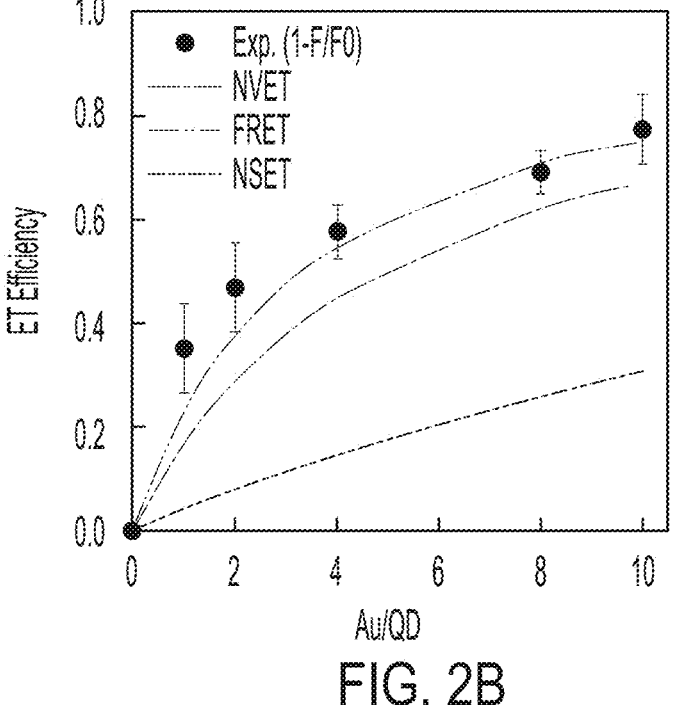
Figure 2C:
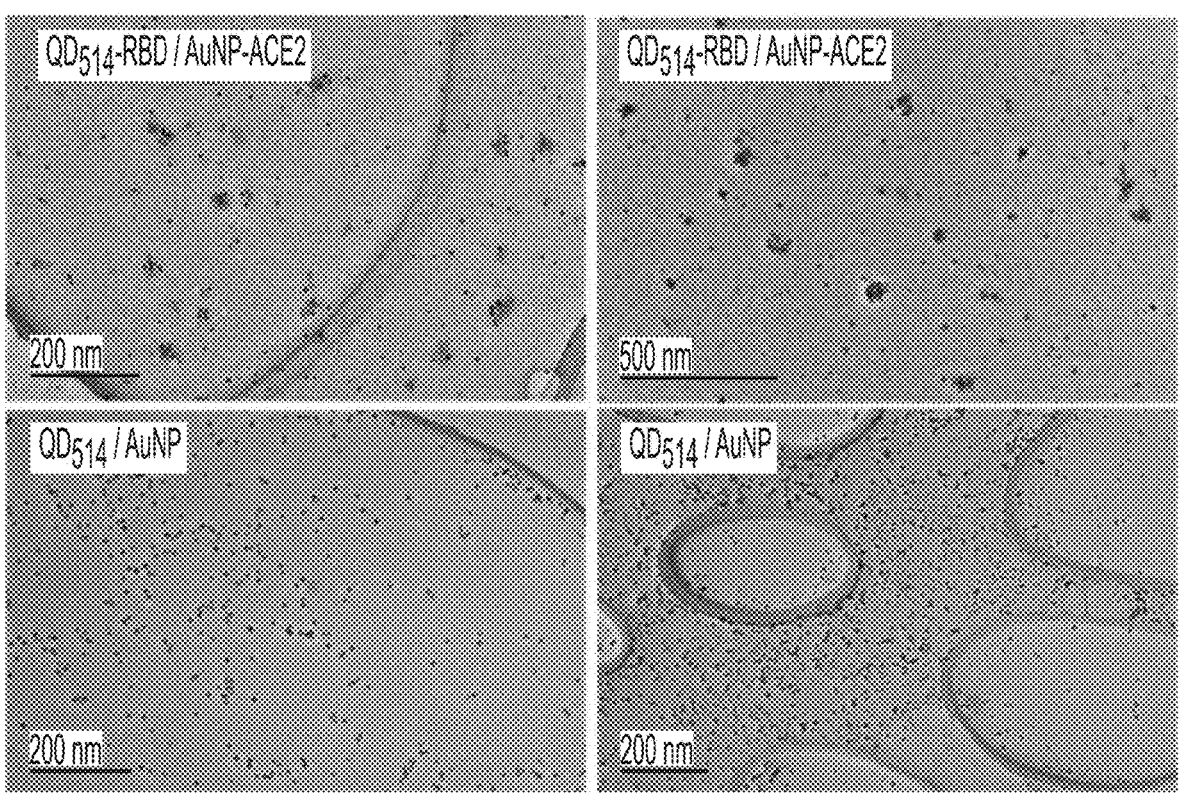

These trials used $QD_{514}$ as the energy transfer donor to achieve higher efficiency due to a better spectral overlap (J) with the AuNP absorption peak (520 nm) and its smaller core size (details in Methods). QD fluorescence decreased with increasing ratios of acceptor per donor (AuNP/QD=0-10) (FIG. 2A). The optimized biochemical assays exhibited 80% maximum energy transfer efficiency and the control AuNP (without ACE2) did not quench the $QD_{514}$-RBD PL, which confirmed the specificity of the RBD-ACE2 interaction. The experimental energy transfer efficiency, $E=(1-F/F_0)$, was compared with three theoretical models; FRET (dipole-dipole interaction, E proportional to $R^6$), NSET (nano-surface damping energy transfer, E proportional to $R^4$) and NVET (nano-volume damping energy transfer, E proportional to $R^3$), as described in the Methods[19-21] (FIG. 2B). Here, F and $F_0$ are the PL of QD with and without AuNP, respectively. The center-to-center distance between QD and AuNP, R, was 17 nm based on the hydrodynamic size. The calculated distance between $QD_{514}$-RBD and AuNP-ACE2 with 50% energy transfer, $R_0$, was 14.4 nm for FRET, which was longer than that for general organic dye acceptors (typically $R_0$<10 nm), owing to the large extinction coefficient of AuNP ($\varepsilon$=1.4×10$^7$ M$^{-1}$cm$^{-1}$ at 520 nm)[22]. With $QD_{514}$-AuNP, the FRET model provided the best fit to the experimental data, which was different from a previous study using QDs and ultra-small AuNP (1.5 nm). Compared to prior work, the calculated FRET model estimated higher efficiency than other models because the extinction coefficient of 5 nm AuNP is 2-3 orders of magnitude higher than that of 1.5 nm AuNP. The NVET model moderately estimated the experimental data, while the NSET model fit poorly because it does not account for acceptor size. While consistent QD quenching was observed using 3 nm AuNP-ACE2 and $QD_{514}$-RBD, the FRET model underestimated the efficiency of smaller AuNPs due to the larger R-dependence. $QD_{514}$-S1 was also tested as the energy donor, and exhibited much lower efficiency because the larger size of S1 compared to RBD (76.5 kDa to 26.5 kDa) resulted in increased separation, R. The TEM images of the Spike- Spike subunit and ACE2, demonstrating that QD-Spike is a viable method for the production of pseudo-virions that can be monitored in real time by their emission characteristics.

Biologics Inhibit NP-Based Energy Transfer

After confirming that $QD_{514}$-RBD quenching could be used to monitor RBD-ACE2 binding, a method was developed to test the inhibitory activity of biological molecules (FIG. 3A). As a proof-of-concept, Fc-tagged recombinant ACE2 (ACE2-Fc) was used in a competition assay to block the interaction of $QD_{514}$-RBD and AuNP-ACE2. Addition of 0.9 μM free ACE2-Fc resulted in 90% PL recovery and half maximal effective concentration ($EC_{50}$) of 200 nM (data not shown). The efficacy of neutralizing antibodies Ab1 and Ab2, specific for SARS-CoV-2 S1 or RBD, respectively, was then tested and found that the PL of $QD_{514}$-RBD was fully recovered in the presence of the neutralizing antibodies (FIG. 3B). The calculated $EC_{50}$ using normalized PL was 60 nM and 125 nM with $R^2$>99% for Ab1 and Ab2, respectively (FIG. 3D). As a control, another non-neutralizing anti-spike antibody was tested and observed no PL recovery (FIG. 3C). These results indicate that the pseudo-virions can enable facile and rapid biochemical screening for repurposed or newly synthesized drugs in addition to neutralizing antibodies or other biologics to prevent SARS-CoV-2 infection.

Quantum Dot Conjugates Induce ACE2-Spike Translocation

The biochemical assays described above demonstrated how QDs conjugated to SARS-CoV-2 Spike can act as a pseudo-virion and bind to ACE2. To understand whether these nanoparticle probes were active in a cell-based system, a C-terminal GFP-tagged ACE2 fusion protein was stably transfected into HEK293T cells (ACE2-GFP HEK293T). This line propagated well, had a high transfection efficiency, and expressed high levels of ACE2 on the plasma membrane. ACE2-GFP clone 2 was treated with 100 nM $QD_{514}$-RBD or $QD_{608}$-RBD for 3 h and the live cells were imaged using an Opera Phenix automated high-content confocal microscope (FIG. 4A).

Figure 4A:
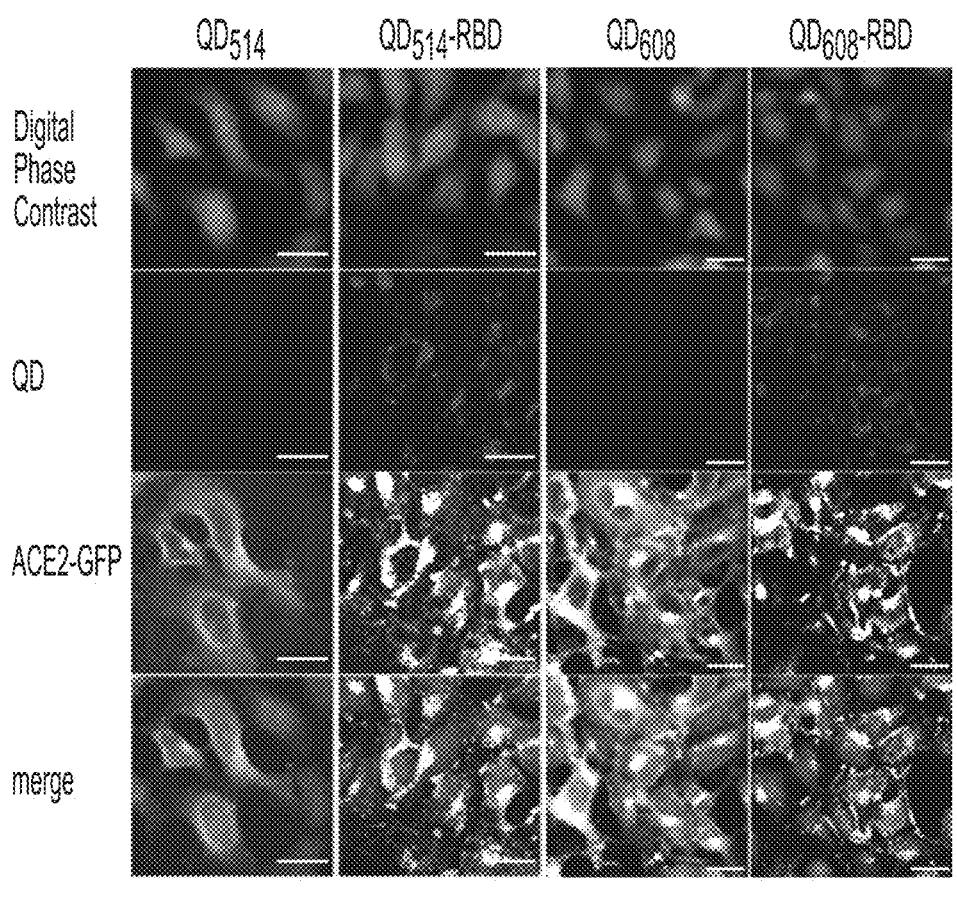
Figure 4B:
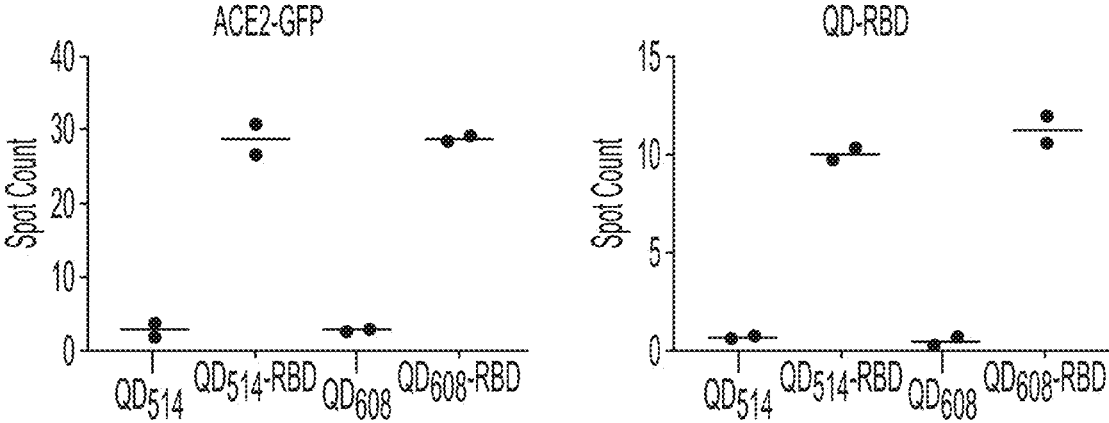

The control unconjugated QDs did not enter cells, nor did they induce any changes in the localization of ACE2-GFP (FIG. 4A). $QD_{514}$-RBD and $QD_{608}$-RBD were both observed to internalize into cells and induced strong translocation of ACE2-GFP. Importantly, the separate ACE2-GFP and $QD_{608}$-RBD signals were strongly co-localized, with little to no $QD_{608}$ signal independent of ACE2-GFP fluorescence. The $QD_{514}$ signal could not be discerned from the ACE2-GFP signal because of overlapping emission spectra and bleed-through as seen in stably transfected ACE2-Expi293F cells that do not have a GFP tag on ACE2. There was no bleed-through in signal when using $QD_{608}$-RBD, therefore it was selected for subsequent cell-based experiments. Furthermore, the QD-RBD fluorescence was only observed in ACE2-GFP cells as seen with ACE2-GFP HEK293T clone 1 that had a lower transfection efficiency. High-content analysis of fluorescent signals demonstrated a large assay window between cells treated with $QD_{608}$-RBD and cells treated with unconjugated $QD_{608}$ when analyzing Spot Counts, indicative of internalized QDs and ACE2 receptor (FIG. 4B). $QD_{528}$ was also generated during initial optimizations and conjugated to the virtually full length recombinant SARS-CoV-2 S1+S2 ECD-His protein. $QD_{528}$-S1+S2 bound to the cell surface and subsequently intracellular puncta could be observed, although internalization was reduced compared to that observed with QD-RBD. In addition, recombinant SARS-CoV-2 RBD alone was able to induce ACE2-GFP translocation. Furthermore, QDs conjugated to the original SARS Spike, SARS-CoV 51, were internalized and strongly colocalized with ACE2-GFP.

To verify that ACE2-GFP cells indeed expressed ACE2, fixed cells were immunostained with mouse anti-ACE2 antibody and no independent yellow or magenta signal corresponding to GFP and QD, respectively, was observed (FIG. 4C). Similarly, no uptake of $QD_{608}$-RBD was observed in wild-type (WT) HEK293T cells (FIG. 4D). In contrast to untagged ACE2-Expi293F, WT HEK239T did not express detectable levels of ACE2 as assessed by immunofluorescence staining (FIG. 4E).

Figure 5A:
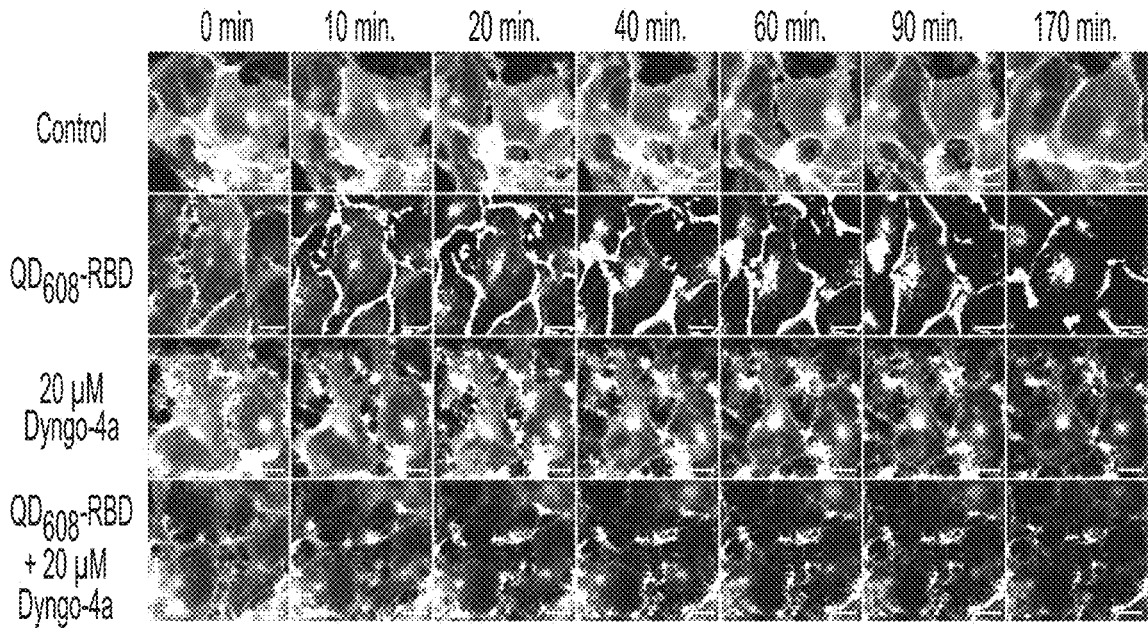

QD$_{608}$-RBD Enters Cells and Induces ACE2-GFP Internalization Through Endocytosis It was observed that $QD_{608}$-RBD could be used at concentrations as low as 5 nM and still observe binding, internalization, and translocation of ACE2-GFP. Concentrations of 10 nM and 20 nM were used in subsequent experiments to ensure sufficient amounts of QD-RBD. One potential mechanism of this translocation and internalization of ACE2-GFP bound to $QD_{608}$-RBD is dynamin- and clathrin-dependent receptor endocytosis, a mechanism that has been proposed for viral entry in some cell types[23]. To confirm this hypothesis, live-cell imaging of ACE2-GFP clone 2 cells was done, with the cells treated with Optimem I as a control, 10 nM or 20 nM $QD_{608}$-RBD and 20 μM Dyngo-4a[24], a dynamin inhibitor (FIG. 5A).

Figure 5B:
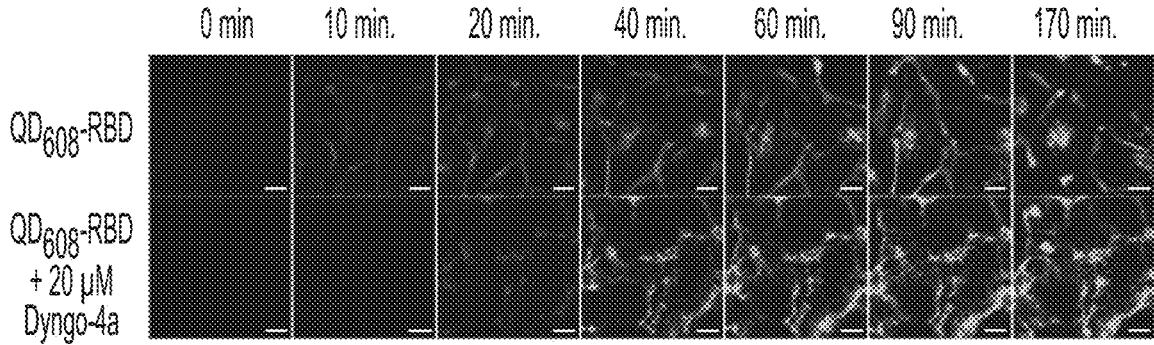
Figure 5C:
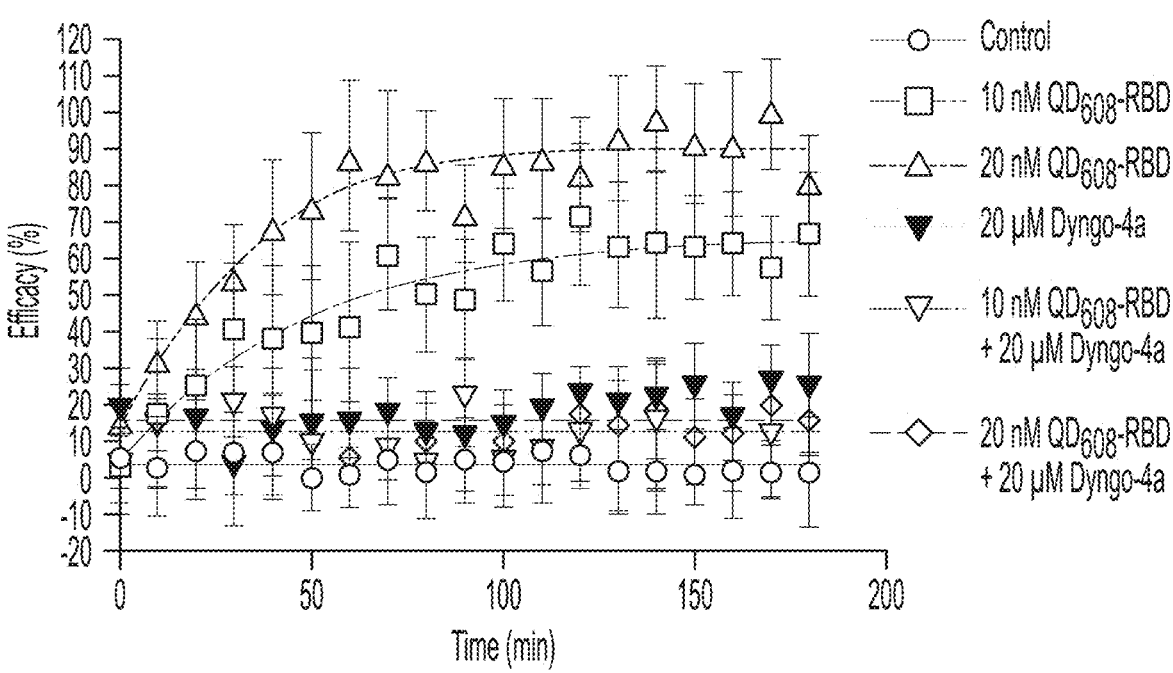
Figure 5C:
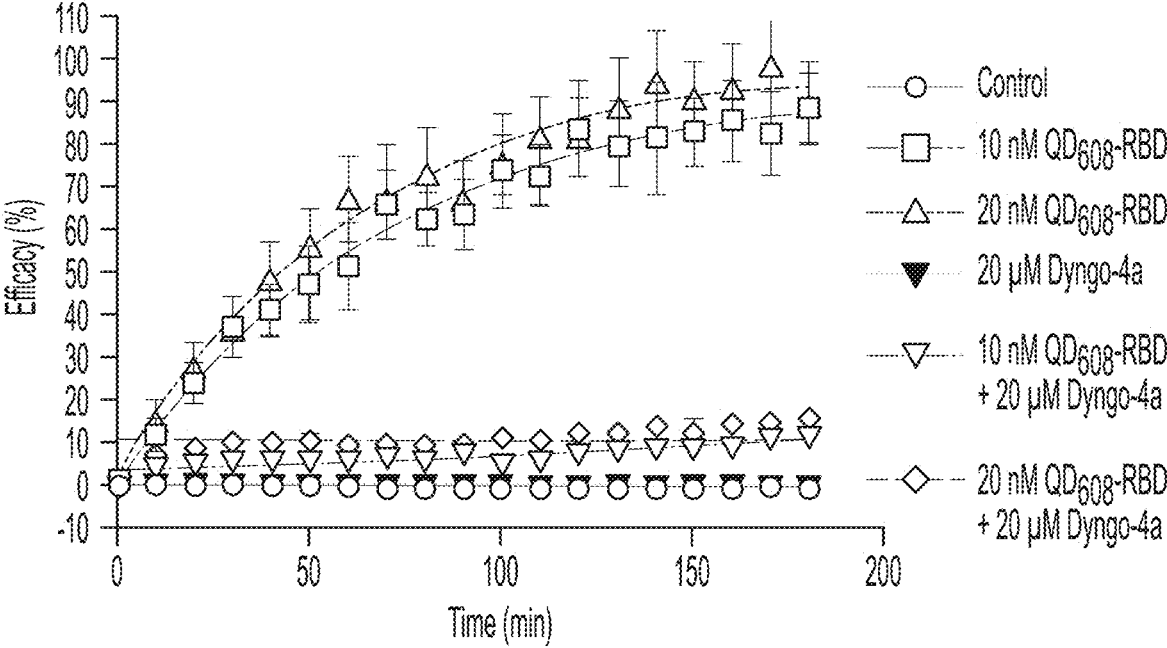

Signals from ACE2-GFP and $QD_{608}$-RBD were captured for cells treated with and without $QD_{608}$-RBD or Dyngo-4a. $QD_{608}$-RBD rapidly bound to ACE2-GFP cells and began internalizing with ACE2-GFP within 10 minutes to form endo(RBD-ACE2). Dyngo-4a alone did not affect the ACE2-GFP localization, but treatment with Dyngo-4a prior to $QD_{608}$-RBD treatment robustly blocked endo(RBD-ACE2). The inhibitory effect of Dyngo-4a was more apparent when quantifying the signal for $QD_{608}$-RBD than for ACE2-GFP. The residual signal from the clustering of ACE2-GFP at the membrane was identified as "Spots" during the high-content analysis (FIG. 5B). However, $QD_{608}$-RBD, while able to bind at the cell surface, was not able to enter cells in the presence of Dyngo-4a, and therefore the quantification revealed a strong inhibitory effect (FIG. 5C).

Single Molecule Tracking Confirms Endocytosis of $QD_{608}$-RBD

Figure 5D:
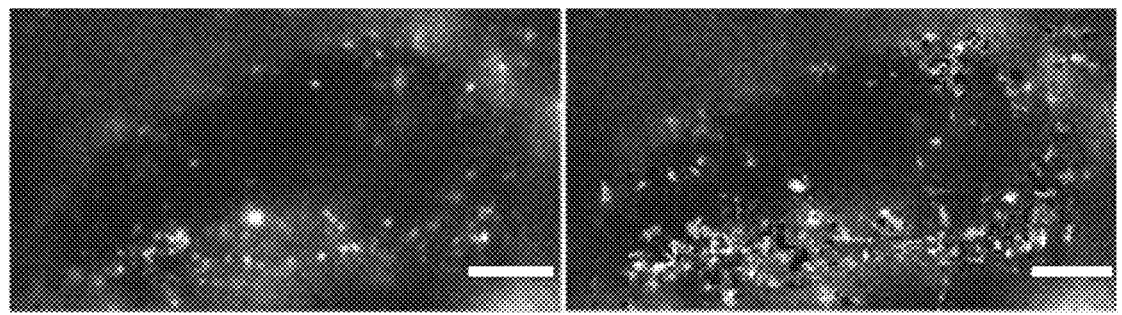
Figure 5E:
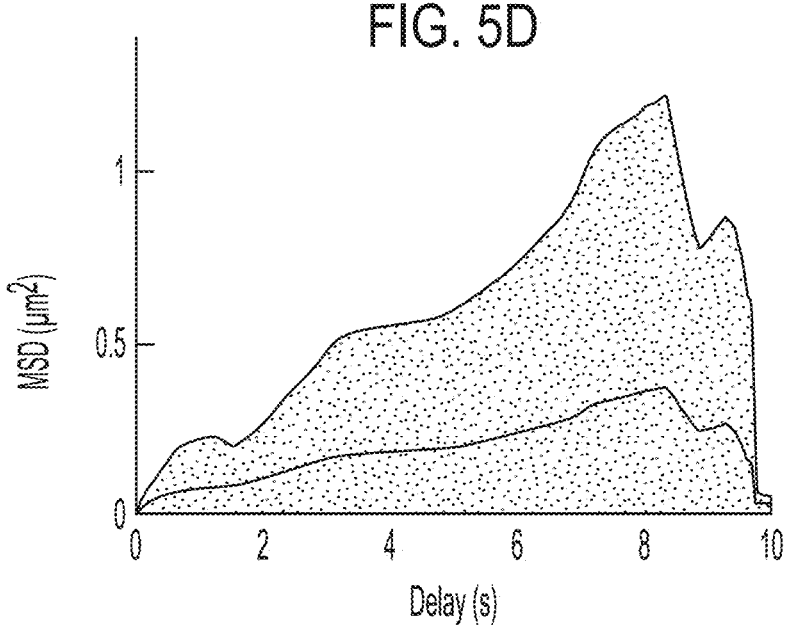
Figure 5F:
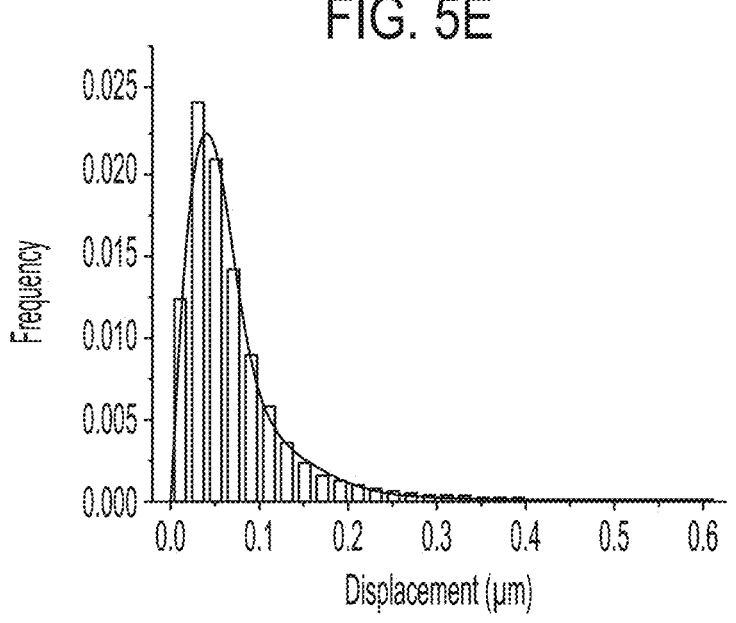

Inclined/total internal reflection fluorescence (TIRF) illumination microscopy[25], a high resolution single molecule microscopy method, was performed in order to further study the spatiotemporal dynamics of $QD_{608}$-RBD. This measured the kinetics of individual quantum dots binding and internalizing into the ACE2-GFP HEK293T cell line (FIGS. 5D-F). In order to image single QDs, a very low concentration of $QD_{608}$-RBD (200 pM) was incubated with ACE2-GFP HEK293T cells for 20 minutes to capture bound and endocytosing particles. One observed very fast binding (within minutes) of $QD_{608}$-RBD to the surface of ACE2 HEK293T cells. Furthermore, the fluorescence intensity fluctuation of $QD_{608}$-RBD on the plasma membrane under TIRF mode was observed suggesting single QD blinking (data not shown). The localization of single QDs was determined through two-dimensional Gaussian fitting. The average mean square displacement (MSD) curve clearly indicated the nature of confined motion of QDs (FIG. 5E). The ensemble MSD analysis reveals the average behavior of $QD_{608}$-RBD. In order to better understand the mobility behavior in the population, one calculated the jump distance traveled by each QD track from one frame to the next and found three different mobilities of $QD_{608}$-RBD in ACE2-GFP HEK293T cells: immobile (0.03 μm$^2$/s), slow (0.13 μm$^2$/s), and fast (0.84 μm$^2$/s) occupying 32%, 52%, and 16% of the population, respectively (FIG. 5F). Most of the tracks corresponded to immobile and slow population demonstrating $QD_{608}$-RBD interacted with the ACE2 receptor. The fast diffusion coefficient population likely reflects receptor-mediated endocytosis as evidenced by active transport that was observed during imaging. These results for the slow diffusion of $QD_{608}$-RBD corresponded to those shown in the literature with regards to membrane compartments where confined diffusion was determined to be 0.12 μm$^2$/s[26]. These results indicate that the nanoparticle movement was vastly different from free diffusion[27] and suggest that $QD_{608}$-RBD interacted with the ACE2 receptor. While this experiment was conducted after 20 min. of $QD_{608}$-RBD incubation, longer-term incubations may reveal different endo(RBD:ACE2) mobility dynamics based on the endosomal location in the cell.

Inhibition of Spike Using Antibodies and Recombinant ACE2

Figure 6A:
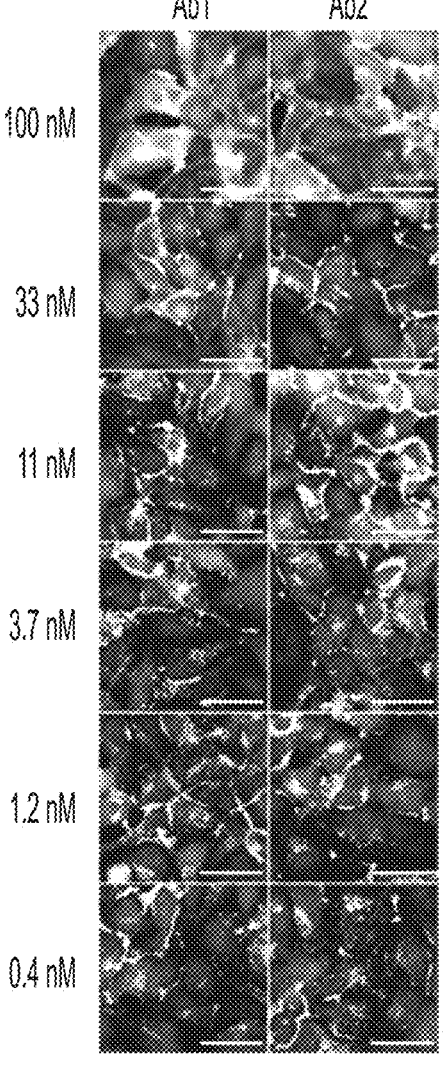
FIGS. 6A-6F show that neutralizing antibodies and ACE2-Fc block $QD_{608}$-RBD induced endocytosis.
Figure 6B:
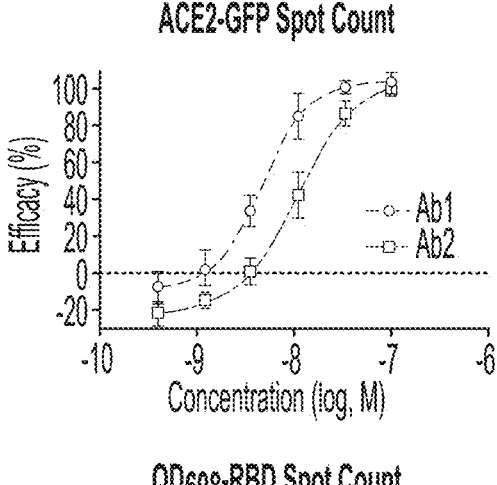
Figure 6B:
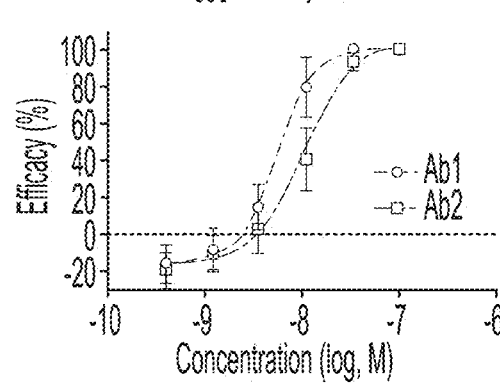
Figures 6C, 6D, 6E:
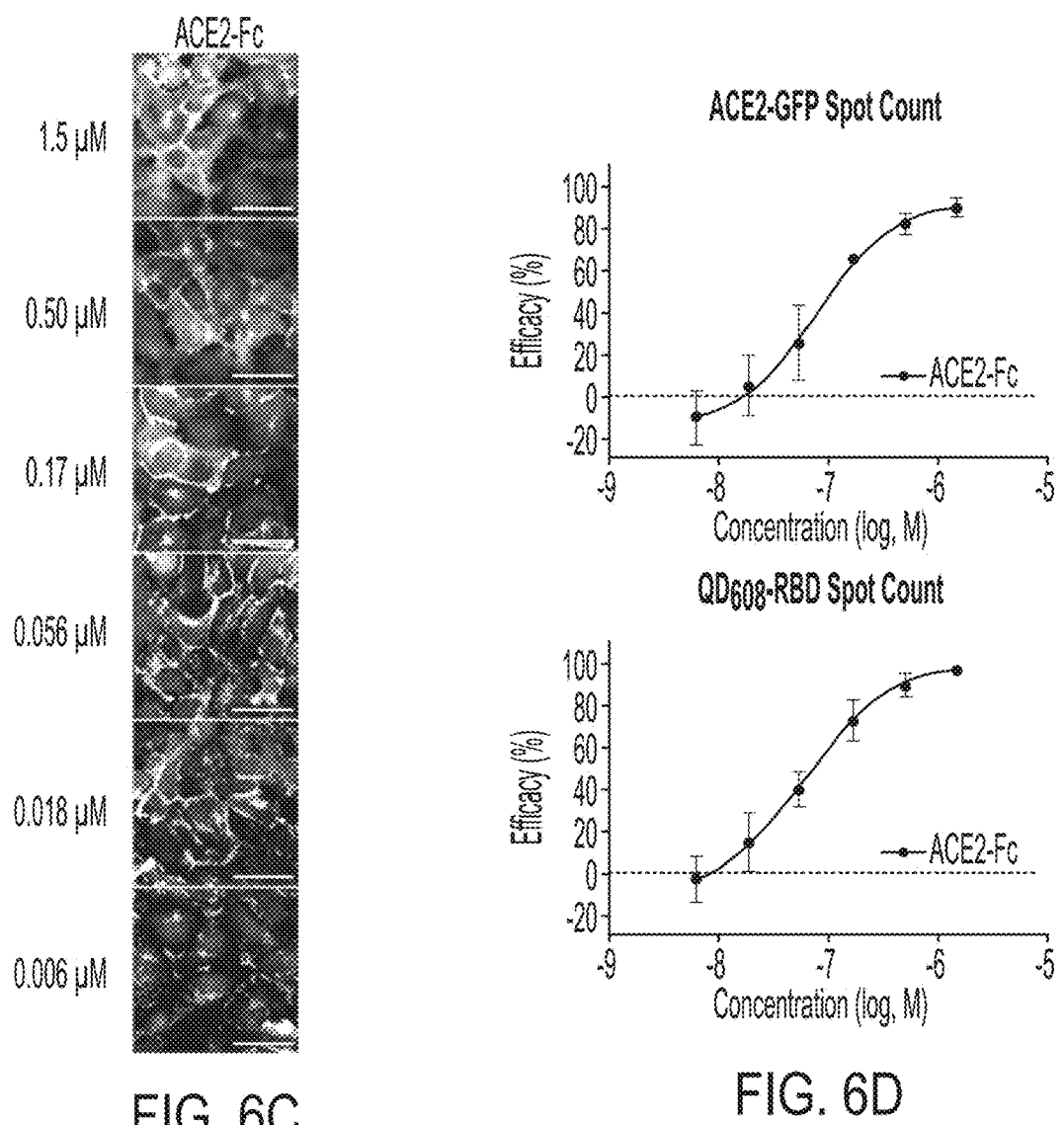
Figure 6F:
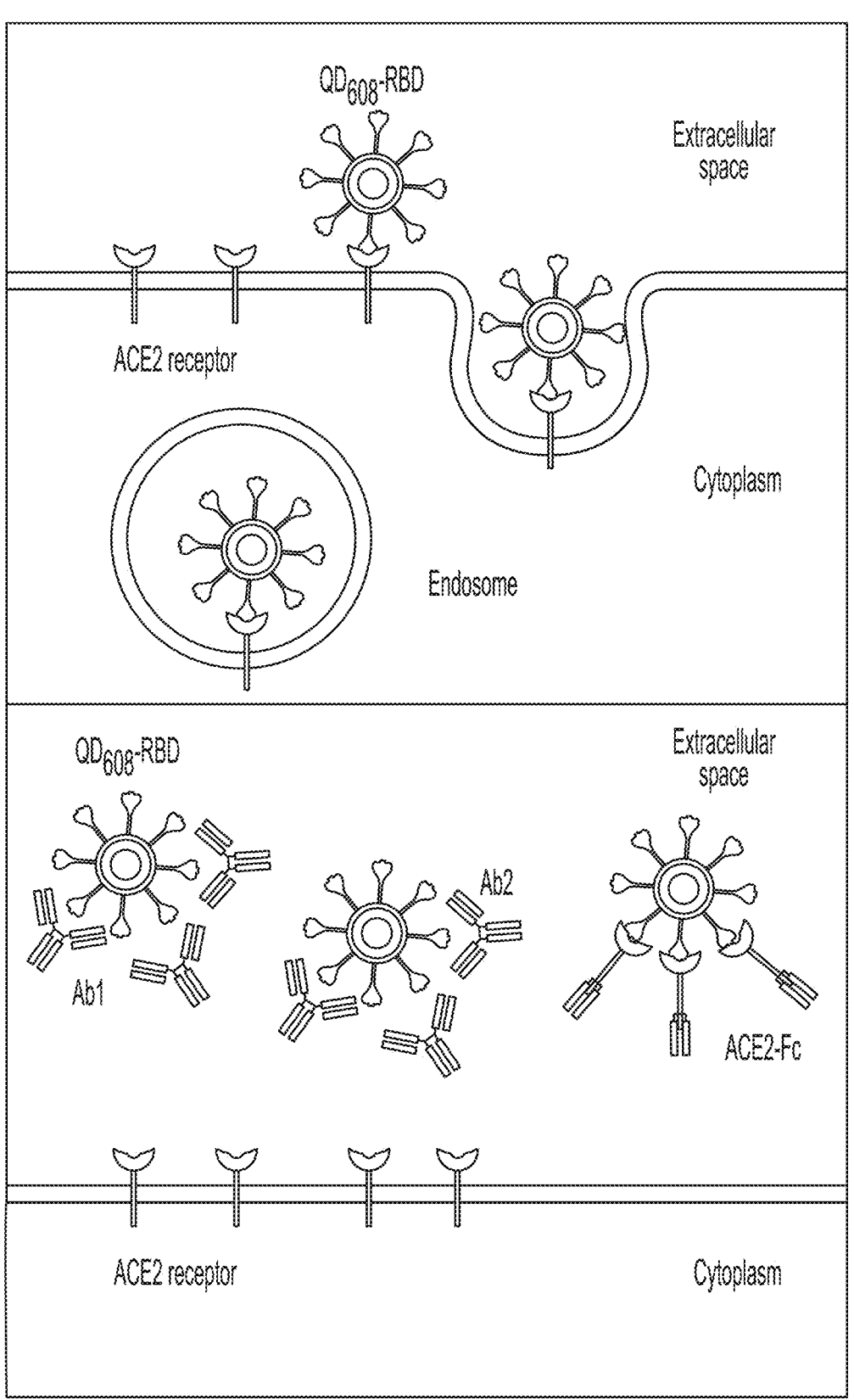

The development of neutralizing antibodies and biologics as SARS-CoV-2 anti-virals has garnered much attention because they can directly block viral entry[28-30]. Using $QD_{608}$-RBD, it was demonstrated that neutralizing antibodies developed against SARS-CoV-2 S1 and RBD potently blocked the binding and internalization phenotype observed in ACE2-GFP HEK293T cells (FIG. 6). While Ab1 was raised against SARS-CoV-2 S1-Fc, Ab2 was raised against SARS-CoV-2 RBD. However, this data demonstrated that Ab1 was more potent than Ab2 against RBD (FIGS. 6A,B). This result is consistent with the biochemical inhibitions carried out prior to the cell-based assays and ELISA assay data reported by the vendor. As with the biochemical inhibition assays, ACE2-Fc was less effective at blocking QD-RBD binding than were the antibodies; Ab1 was 8-fold more potent than ACE2-Fc (FIGS. 6C-E).

The addition of any exogenous material, whether small molecule or biologic, may have cytotoxic effects that can confound any observed experimental phenomenon. In order to assess the cytotoxicity of $QD_{608}$-RBD, ATPlite cell viability assays were conducted following the biologics inhibition assays. The ATPlite luminescence signal is dependent upon the amount of ATP in cells. Cells with low viability will have lower levels of ATP than cells with high viability. Neither $QD_{608}$-RBD, Ab1, Ab2, nor ACE2-Fc exhibited any cytotoxicity after three h of treatment. The negative control cells treated with $QD_{608}$-RBD alone and the positive control cells treated with Optimem I alone both had equal levels of ATP as reported by the ATPlite luminescence-based reading. These data support the idea that QDs used in this study were not cytotoxic, as previously reported[31], nor was the RBD domain from SARS-CoV-2 itself.

The Epithelial Lung Cancer Cell Line Calu-3 can Uptake $QD_{608}$-RBD

The permissiveness of different cell types and tissues for SARS-CoV-2 infection is a central question for the research community[32-34]. It is important to understand how and whether cells are infected by SARS-CoV-2 and what those effects may be, cytopathic or otherwise[35]. To shed some light on this question and to explore the utility of the QD-RBD reagent further, Calu-3 cells[36], a cancer cell line derived from lung epithelium and commonly used in coronavirus infection assays, were cultured and treated with 20 nM $QD_{608}$-RBD. A maximum intensity projection from a 28 μm confocal Z-stack demonstrated entry into some Calu-3 cells, particularly ones that were isolated as opposed to clustered. Calu-3 cells were immunostained for ACE2 expression using the mouse anti-ACE2 antibody and revealed some level of expression, although weaker than the ACE2-Expi293F cells shown above. It seems possible that even low levels of ACE2 expression in Calu-3 can facilitate $QD_{608}$-RBD binding and cell entry.

Nanobody Inhibition of Binding

It was further found that appropriate single-domain antibodies (also known as nanobodies) were effective in preventing binding (data not shown).

High-Throughput Assays

Figure 7A:
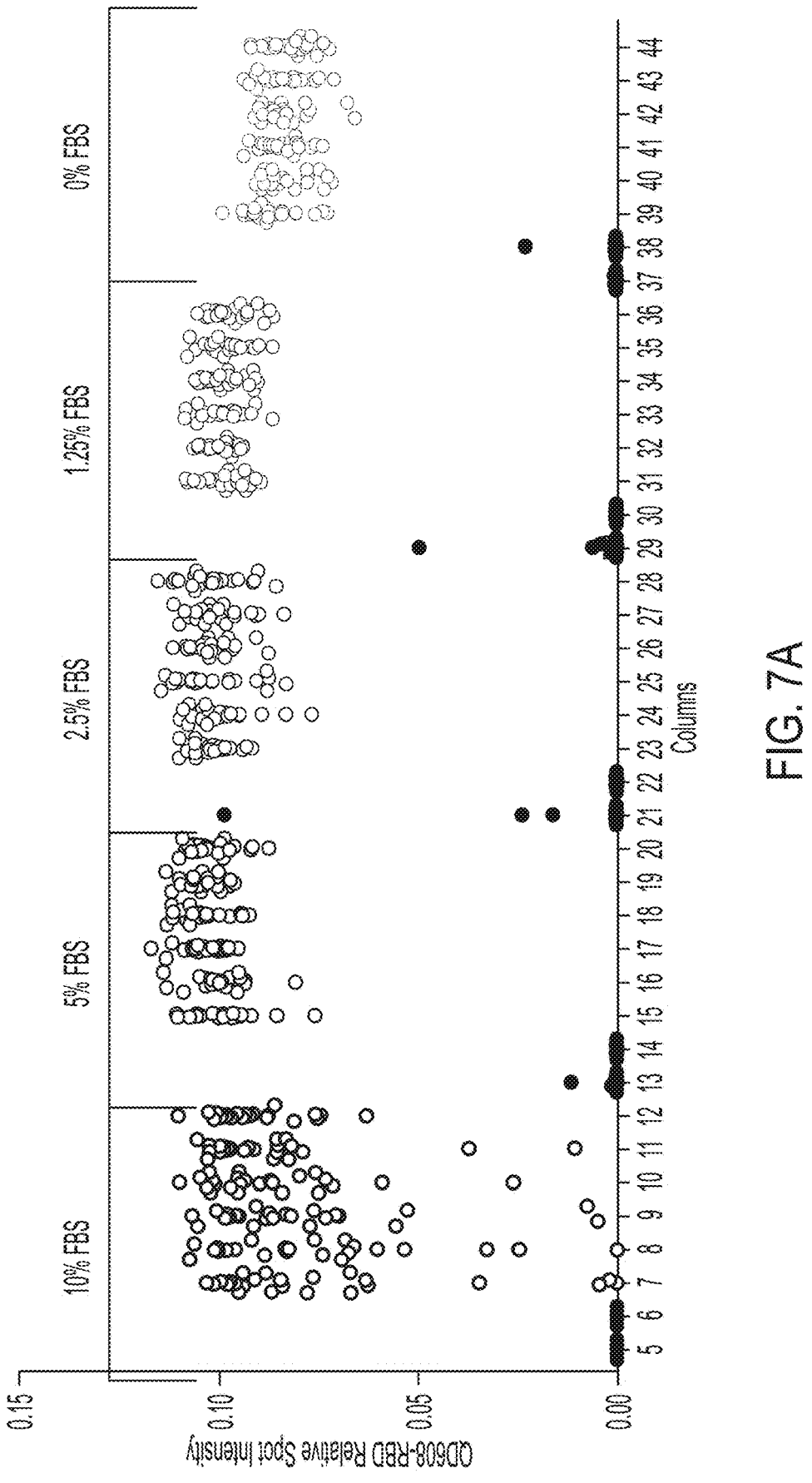
Figure 7A:
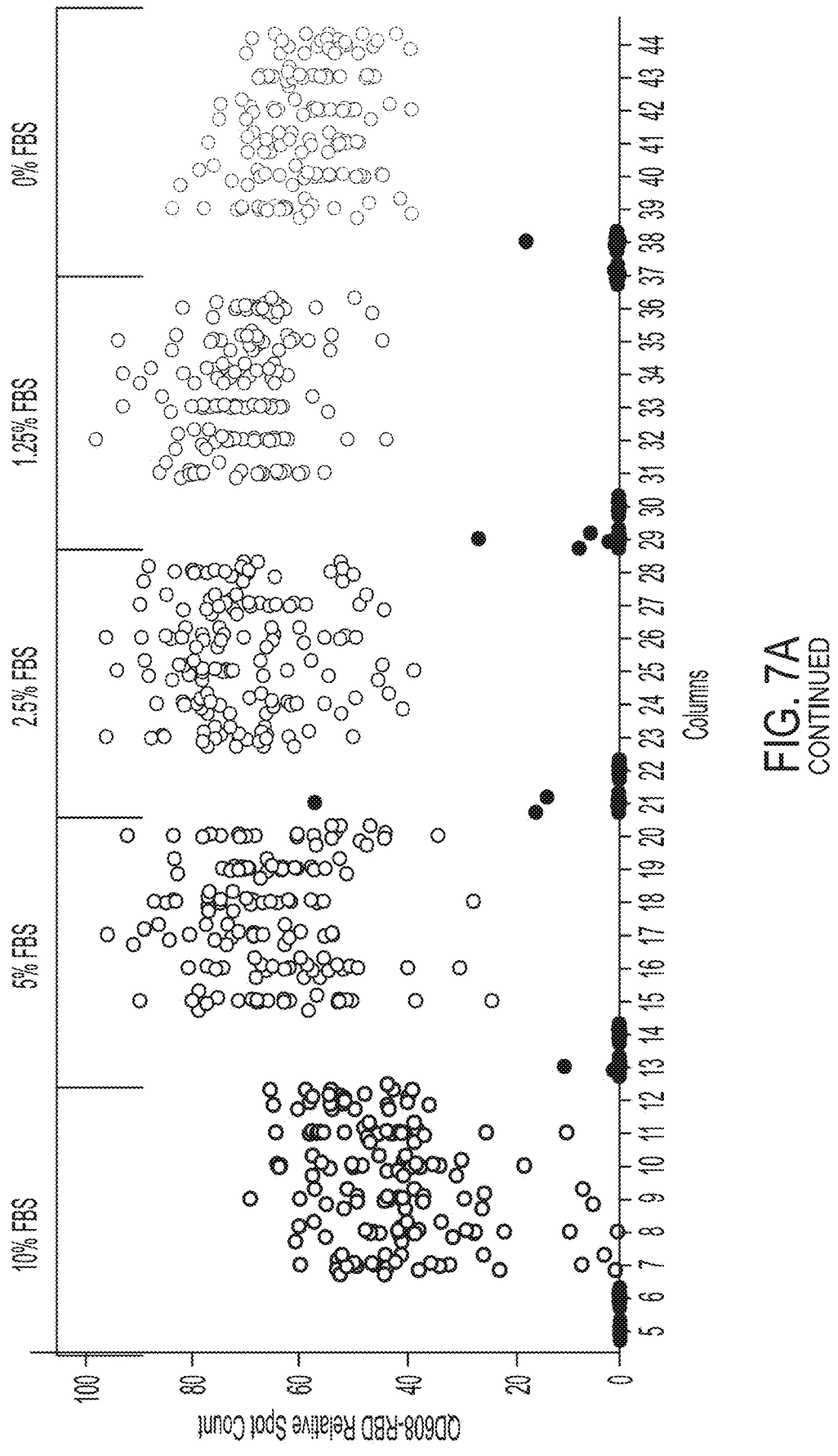
Figure 7A:
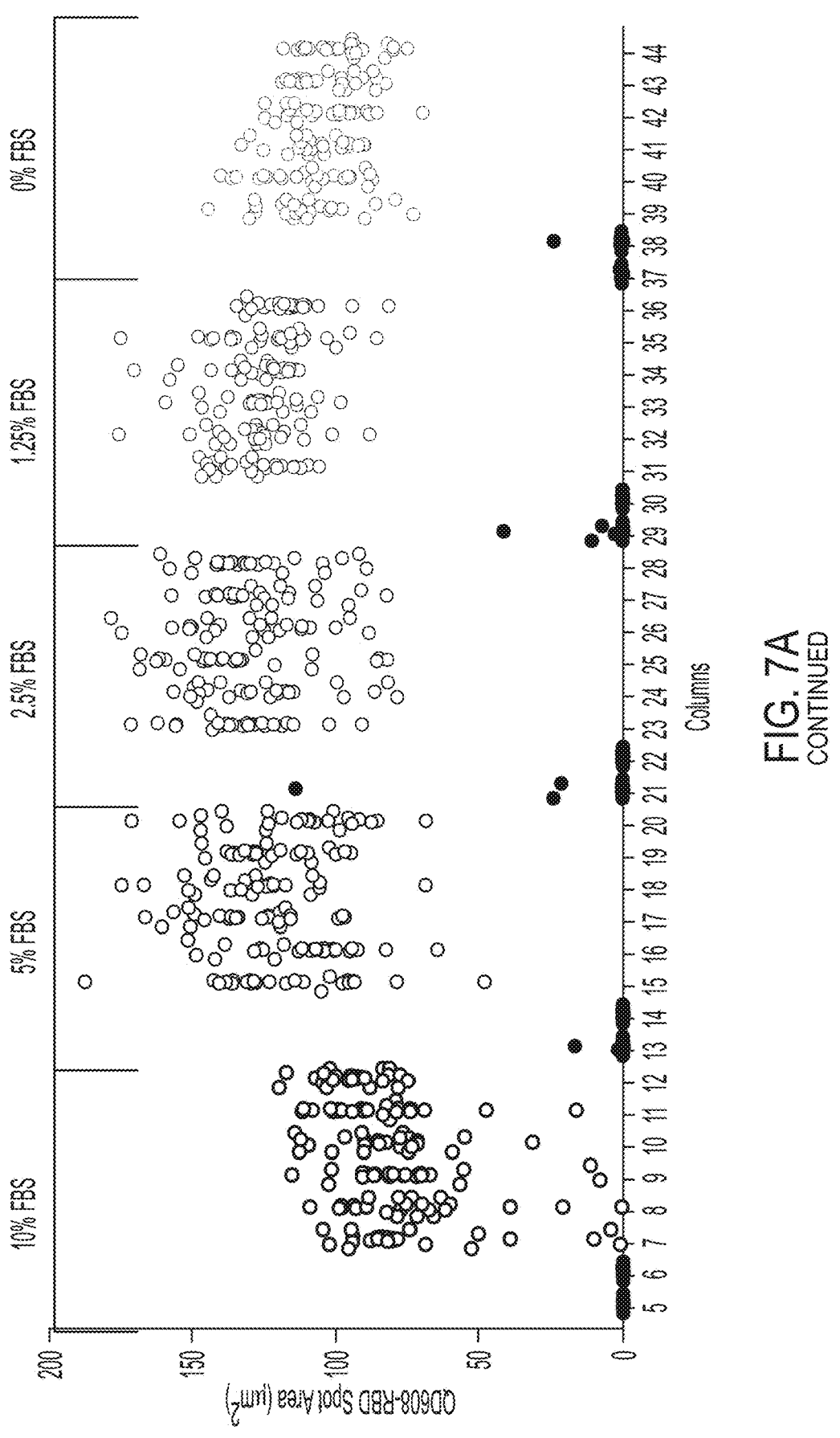
Figure 8A:
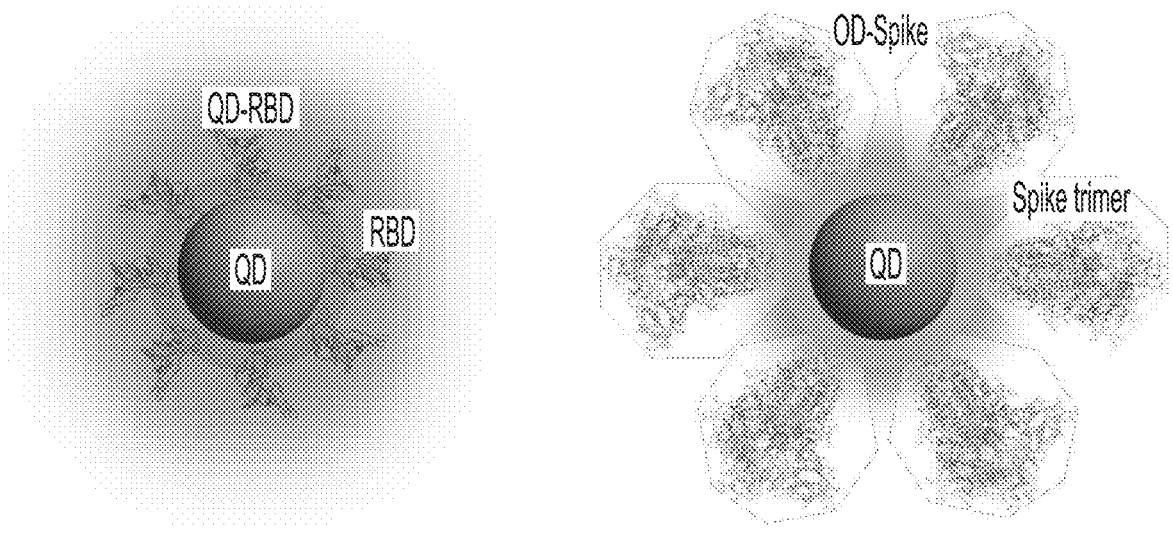
FIG. 8A depicts the extended design of QD using full Spike trimer including Washington Strain Spike and variants of concern in Spike (QD-Spike), instead of using RBD (QD-RBD).
Figure 8B:
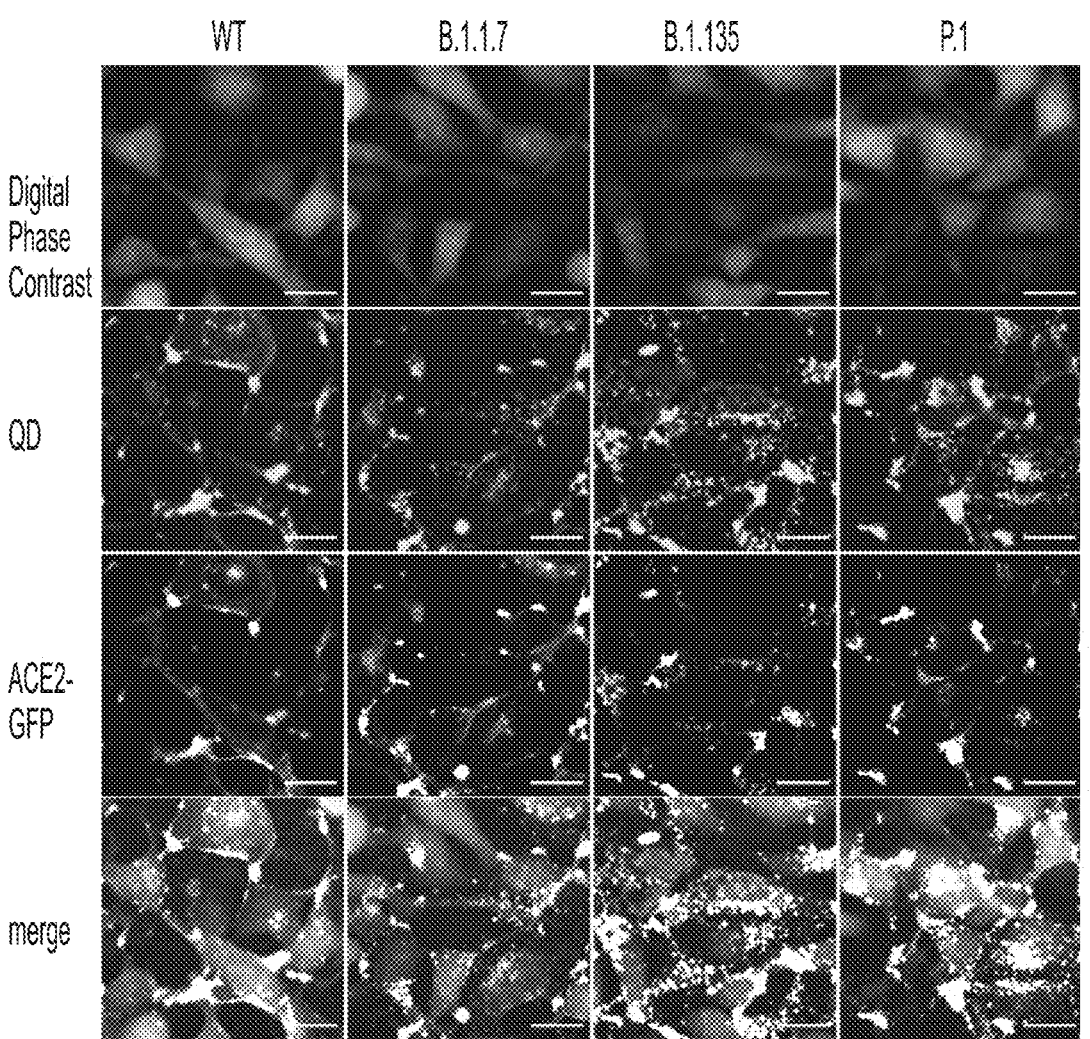
FIGS. 8B-8D show that quantum dot (QD)-conjugated with various types of full Spike trimers induces translocation of ACE2 and internalizes into cells, whose results are different depending on Spike variants (Washington strain: WT, Variants of concerns: UK Strain (B.1.1.7, alpha α), South African Strain (B.1.135, beta β) and Brazilian Strain (P.1, gamma γ)).
Figure 8C:
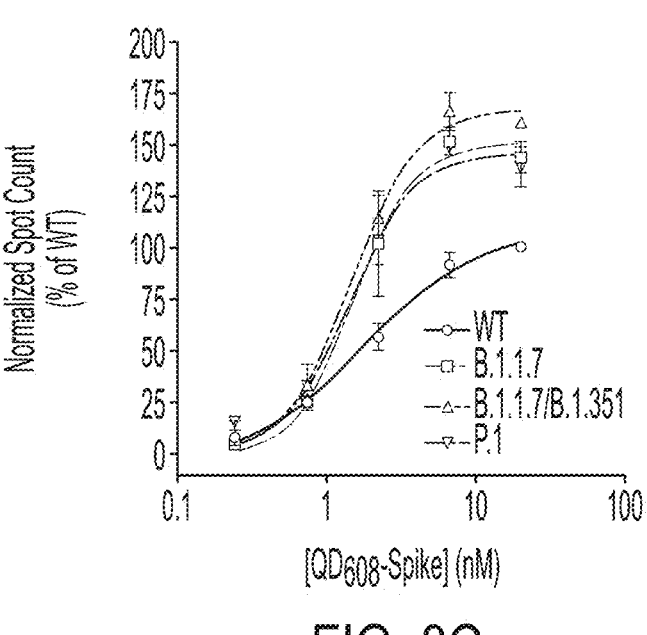
Figure 8D:
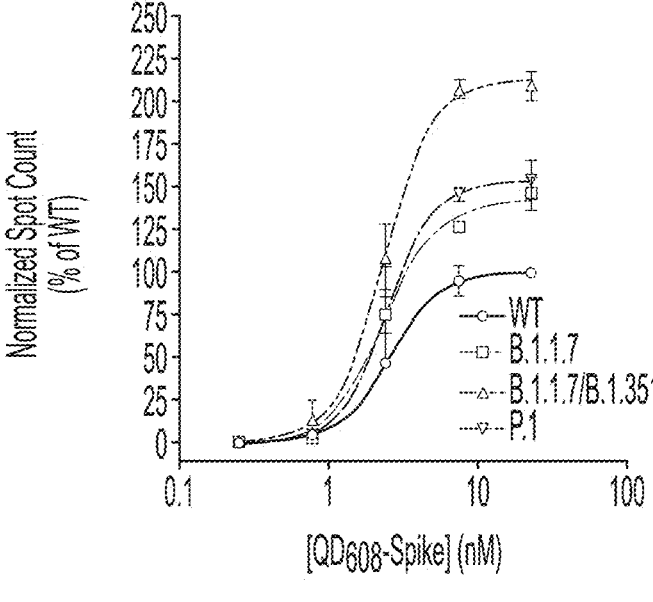
Figure 8E:
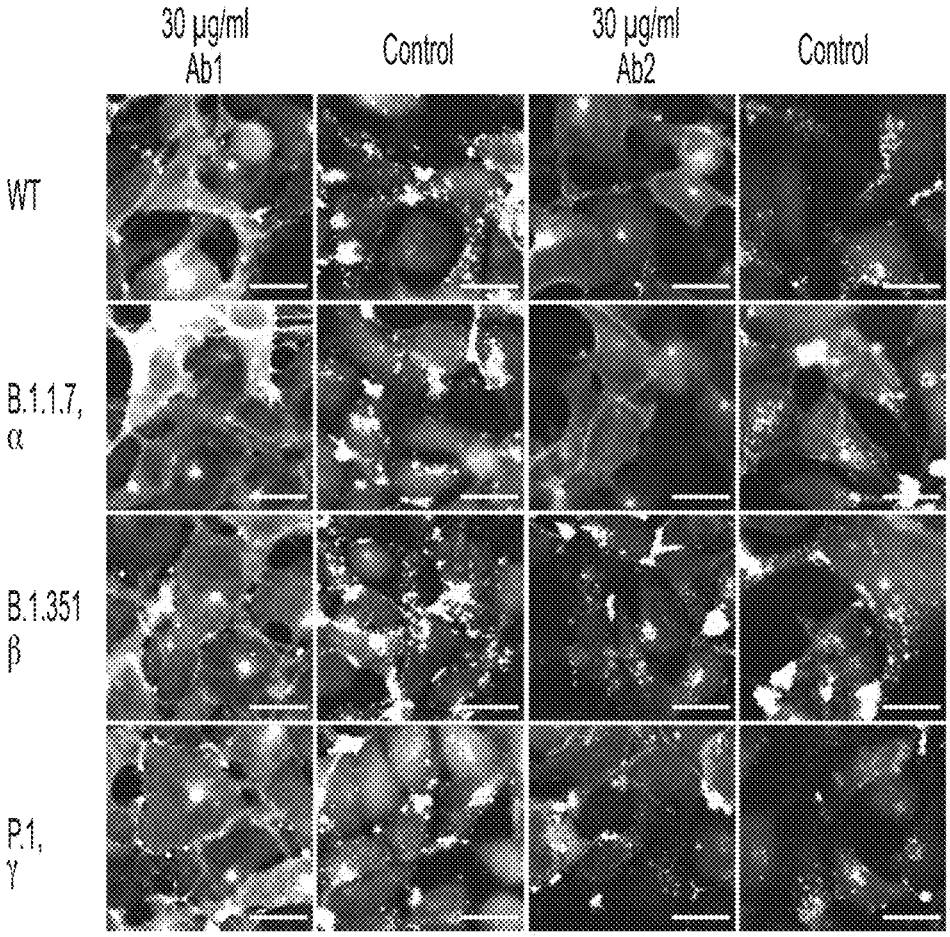
FIGS. 8E-8I show that neutralizing antibodies (Ab1 and Ab2) and ACE2-Fc block various types of $QD_{608}$-Spike trimer induced endocytosis. The results are different depending on Spike variants (Washington strain: WT, Variants of concerns: UK Strain (B.1.1.7, alpha α), South African Strain (B.1.135, beta β) and Brazilian Strain (P.1, gamma γ)).
Figure 8F:
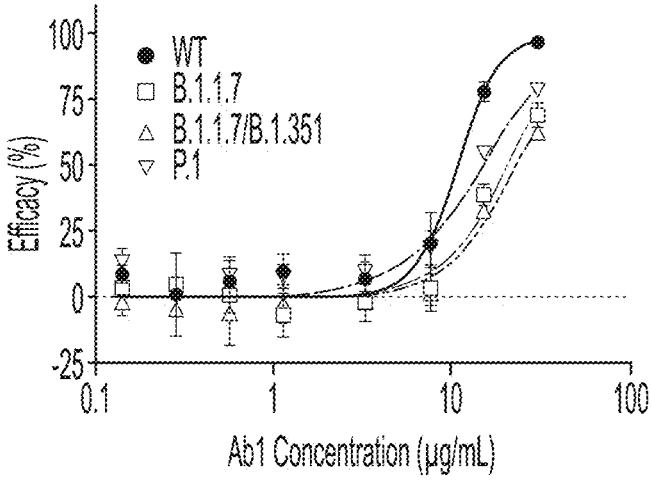
Figure 8G:
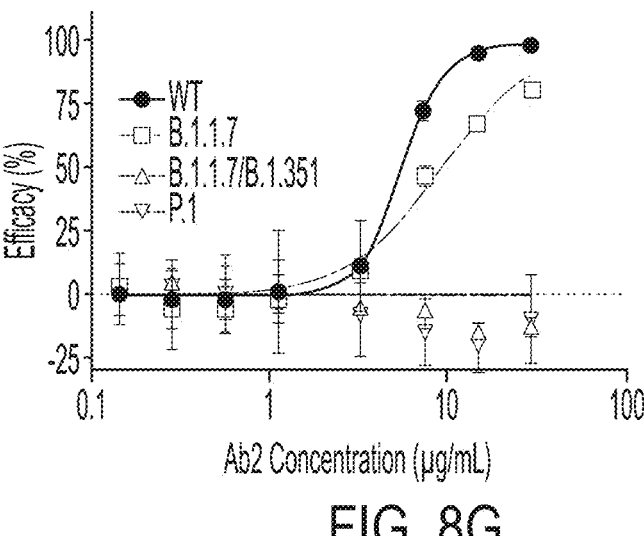
Figure 8H:
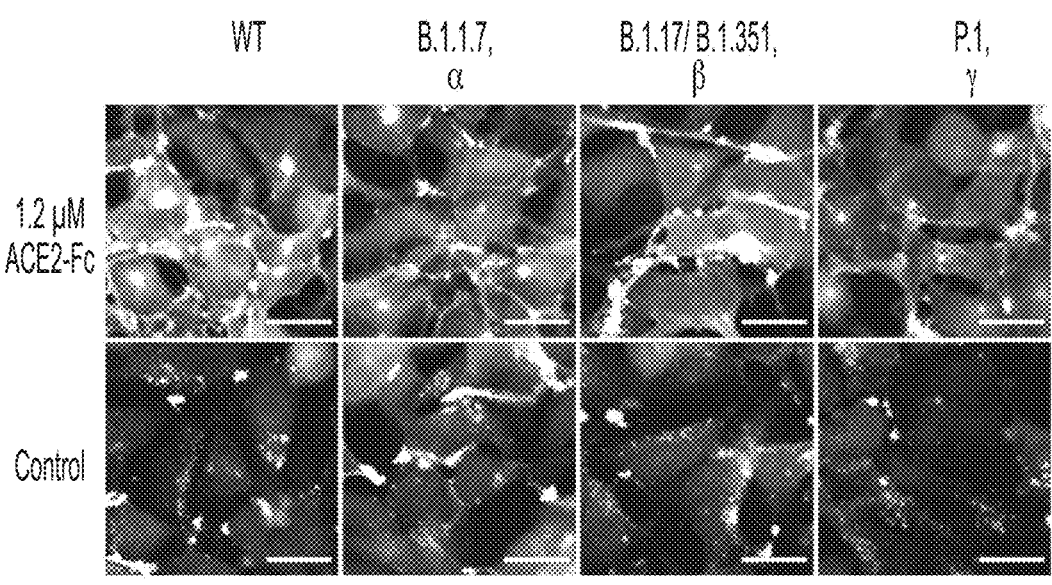
Figure 8I:
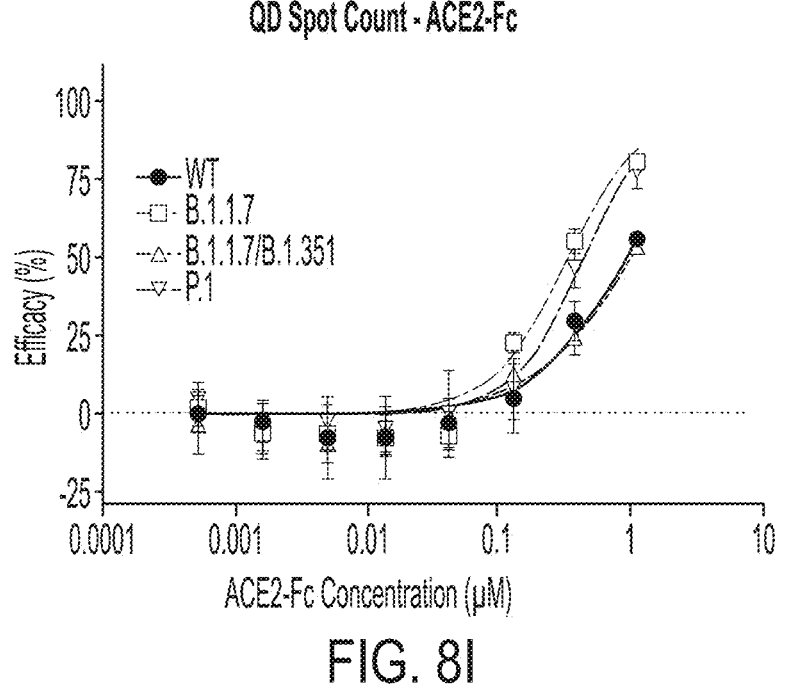

This technique was demonstrated in a high-throughput screening application. ACE2-GFP HEK293T cells were plated at 1000 cells per well in Fluorobrite DMEM containing varying concentrations of FBS. Cells were cultured for 24 hours before QD treatment. Total volume of cell suspension was 3 μL per well. $QD_{608}$-RBD was diluted in Optimem I without phenol red and 1 μL of a 4× solution was dispensed into 3 μL of Fluorobrite DMEM. Plates were incubated for 3 hours before imaging on the Opera Phenix (Perkin Elmer) using a 40× water immersion objective. Images were processed in Columbus Analyzer (Perkin Elmer) and high-content analysis was used to produce quantitative measurements of Relative Spot Intensity, Spot Count, and Spot Area (μm²). Data are provided in FIGS. 7A and 7B.

Assays Using Full Spike Trimers

Beyond testing with RBD, this assay format was demonstrated to operate with the full Spike trimer protein (S1+S2) of several variants of interest. These proteins included RBD domains comprising SEQ ID NOs: 1 through 4, inclusive. The four sequences correspond to the same "wild-type" domain used in the above-described tests, and the alpha, beta, and gamma variants, respectively. The RBD of the delta variant, SEQ ID NO: 5, was not tested, but it is expected to perform just as the others. The tested S1+S2 Spike trimers (which include the embedded RBDs) comprised the sequences of SEQ ID NOs: 6 through 9, inclusive, plus short linkers and polyhistidine tags. These correspond to the wild-type, alpha, beta, and gamma variants, respectively. SEQ ID NO: 10 corresponds to the full Spike trimer of the Delta protein, again not tested but expected to perform the same.

Methods

Reagents and Materials

CdO (99%) and tri-n-octylphosphine (TOP; min. 97%) were purchased from Strem Chemicals. Behenic acid (99%), 1,2-hexadecanediol (technical grade, 90%), Oleylamine (technical grade, 70%), n-octanethiol (98.5+%), and LiOH (≥98%) were purchased from Sigma-Aldrich. 1-Octadecene (ODE; technical grade, 90%) was purchased from Acros Organics. Selenium dioxide (≥97%) was purchased from Fluka. Oleic acid (technical grade, 90%) and 2-(2-amino-ethoxy)ethanol (98%) were purchased from Alfa Aesar. All other chemicals, including solvents, were purchased from Sigma-Aldrich or Acros Organics and were used as received.

Dulbecco's Modified Essential Media (DMEM) (10313021), tetrachloroauric (III) acid, sodium hydroxide, ascorbic acid, sodium citrate, boric acid, Optimem I (11058021), Penicillin/Streptomycin (15140122), 7.5% Bovine Serum Albumin Fraction V (15260037), Goat-anti-mouse AlexaFluor 488 (A32723; RRID:AB_2633275), High Content Screening Cell Mask Deep Red (1132721), Hoechst 33342 (H3570), and Lipofectamine 3000 (L3000001), was purchased from ThermoFisher Scientific. Mouse anti-ACE2 Antibody (E-11): sc-390851 was purchased from Santa Cruz. Hyclone Fetal Bovine Serum (FBS) (SH30071.03) was purchased from General Electric Healthcare. 32% paraformaldehyde (15714S) was purchased from Electron Microscopy Sciences. Greiner 96-well poly-D-lysine coated clear bottom black microplates (655946) were purchased from Greiner Bio-One. SARS-CoV S1-His (40150-V08B1), SARS-CoV-2 S1S2 ECD-His (40589-V08B1), SARS-CoV-2 S1-His (40591-V08H), and SARS-CoV-2 RBD-His (40592-V08B), anti-SARS-CoV-2 S1 neutralizing antibody mouse mAb Ab1 (40591-MM43), and anti-SARS-CoV-2 RBD neutralizing antibody mouse mAb Ab2 (40592-MM57) was purchased from Sino Biological. ACE2-Fc (Z03484) was purchased from Genscript. pCMV6-AC-ACE2-GFP (RG208442) plasmid was purchased from Origene Technologies. Dyngo-4a (ab12068) was purchased from Abcam. ACE2-GFP HEK293T (CB-97100-203) and ACE2-untagged Expi293F cells were purchased from Codex Biosolutions.

QD Synthesis.

514 nm emitting $ZnSe/Cd_{0.4}Zn_{0.6}S/ZnS$ core-shell QDs and 528 nm emitting CdSe/CdS/ZnS core-shell QDs were synthesized as previously described[43,44]. 608 nm emitting CdSe/CdS/ZnS core-shell QDs were synthesized via modification of published procedures. (i) CdSe core synthesis: CdSe core was synthesized following the published procedure with some modifications[45]. CdO (77 mg, 0.60 mmol), behenic acid (0.613 g, 1.80 mmol) and ODE (5.0 ml) were loaded in a 50-mL three-neck flask. The mixture was heated to 260° C. under $N_2$ to dissolve the Cd precursor. The mixture was cooled to 50° C., and ODE (15 ml) and 1,2-hexadecanediol (0.155 g, 0.60 mmol) were further added. The mixture was degassed at 100° C. for 30 min, then cooled to room temperature. $SeO_2$ (66.6 mg, 0.60 mmol) was added, and the reaction mixture was heated to 240° C. at a rate of −25° C./min under $N_2$. In 3 min after the temperature reached 240° C., oleic acid (0.60 ml) was added dropwise, the heating mantle was removed, and the reaction mixture was cooled below 50° C. TOP (0.6 ml), oleylamine (0.6 ml), hexane (9 ml) and methanol (18 ml) were added to the reaction mixture, and the methanol layer was discarded after vigorous stirring for a few min. An identical washing procedure was repeated a few more times. The QD solution was transferred to 40-mL vials, and excess isopropanol and ethanol were added to flocculate the QDs. The mixture was centrifuged at 3,800 rpm for 5 min. The supernatant was discarded and the QD pellet was dissolved in $CHCl_3$. The final CdSe QD concentration was estimated following the literature method[46]. (ii) Precursor preparation for overcoating: 0.2 M Cd oleate, 0.2M Zn oleate and 0.2M n-octanethiol solutions for overcoating procedure were prepared as previously described[43]. (iii) Overcoating of CdSe core with CdS and ZnS shells: ODE (5.0 mL), oleylamine (5.0 mL), TOP (1.5 mL), and the CdSe QD core (0.15 μmol in 0.54 mL of $CHCl_3$ solution) were loaded into a 100-mL four-neck round-bottom flask. The reaction mixture was degassed under vacuum at 100° C. to remove $CHCl_3$ and other volatiles, and backfilled with $N_2$. The amount of shell precursors used for the overcoating was calculated following the literature procedure[47]. For the coating of CdS layers, 0.2 M n-octanethiol in ODE (0.20 ml) was added to the reaction mixture at 100° C. Then the reaction mixture was heated to 300° C. 0.2 M Cd oleate and 0.2 M n-octanethiol in ODE was separately added dropwise using syringe pumps starting at 200° C. 1.2-fold excess of n-octanethiol to Cd oleate was used during the CdS overcoating. After the precursor addition was done, the reaction mixture was left for 5 min, then cooled to 200° C., and annealed for 30 min. The reaction mixture was further cooled to 100° C., and degassed for 30 min to remove volatiles. After backfilling with $N_2$, a coating of ZnS layers was further performed in a similar fashion. The reaction mixture was heated to 290° C. 0.2 M Zn oleate and 0.2 M n-octanethiol in ODE were separately added dropwise starting at 250° C. 1.4-fold excess of n-octanethiol to Zn oleate was used during the ZnS overcoating. After the precursor addition was done, the reaction mixture was left for 5 min, then cooled to 240° C., and annealed for 30 min.

QD Ligand Exchange.

Typical procedures for the ligand exchange are as follows: QDs coated with native hydrophobic ligands (8.0 nmol in stock solution) were flocculated by mixing with isopropanol and methanol in a 20-mL vial. The mixture was centrifuged at 3,800 rpm for 5 min. The clear supernatant was discarded. The QD pellet was mixed with 2-(2-aminoethoxy)ethanol (0.5 mL), $CHCl_3$ (0.8 ml) and methanol (0.8 ml). The reaction mixture was stirred at 45° C. overnight under $N_2$. Excess ethyl acetate was added to the mixture to flocculate the QDs. The mixture was centrifuged at 3,800 rpm for 5 min, and the supernatant was discarded. The QD pellet was mixed with $CHCl_3$ (1.0 mL) and methanol (0.5 mL). For the ligand preparation, LiOH (10.2 mg, $4.3\times10^{-4}$ mol) was added to a mixture of CL4 methyl ester precursor[48] (76 mg, $1.8\times10^{-4}$ mol), methanol (0.8 mL) and DI water (0.7 mL). The reaction mixture was stirred at room temperature for 30 min. 4 M HCl was then added dropwise to the reaction mixture to adjust the pH to approximately 7, and $NaBH_4$ (20.4 mg, $5.4\times10^{-4}$ mol) was added to the ligand solution, which was further stirred at room temperature for 1 h under $N_2$. Then, 4 M HCl was added dropwise to the reaction mixture to adjust the pH to approximately 7. The ligand solution was injected by a syringe into the QD solution prepared above with vigorous stirring, and DI water (~0.7 mL) was further mixed in. The biphasic mixture was stirred at 45° C. overnight under $N_2$. After cooling, the $CHCl_3$ layer was collected by a syringe and discarded. The residual $CHCl_3$ in the aqueous layer was removed by evaporation. The aqueous layer was then filtered through a Millex-LCR membrane filter (pore size 0.45 μm, Millipore) and transferred to a centrifugal spin dialyzer (Amicon Ultra 50K, Millipore). The mixture was diluted with DI water and centrifuged at 3,800 rpm for 5 to 10 min., and the clear, filtered solution was discarded. To remove excess unbound ligands and other byproducts, the QD dispersion was subject to a few additional rounds of centrifugation with DI water, followed by filtration through a Millex-LG membrane filter (pore size 0.20 μm, Millipore).

Synthesis of 5 nm AuNPs

AuNPs were synthesized as previously described with slight modification[49]. 5 nm AuNPs were synthesized by a seeded growth method using 3.2 nm seed AuNPs. First 3.2 nm seed NPs were synthesized with sodium citrate and $NaBH_4$. 125 μL ($1.25\times10^{-5}$ mol) of 100 mM tetrachloroauric (III) acid ($HAuCl_4\cdot3H_2O$) aqueous stock solution, 125 μL ($2.5\times10^{-5}$ mol) of 200 mM of sodium citrates stock solution were dissolved in 50 mL of deionized $H_2O$; the mixture was then stirred at room temperature for 5 min. 125 μL ($1.0\times10^{-4}$ mol) of 1 M sodium borohydride ($NaBH_4$) stock solution in deionized water was added with vigorous stirring. For 5 nm AuNP, the growth solution was prepared with 100 μL ($1.00\times10^{-5}$ mol) of 100 mM tetrachloroauric (III) acid ($HAuCl_4\cdot3H_2O$) aqueous stock solution and 100 μL ($2.0\times 10^{-5}$ mol) of 200 mM of sodium citrates stock solution that were dissolved in 50 mL of deionized $H_2O$. The desired amount of seed NPs, calculated based on the target size of AuNPs and seed size, was added to the growth solution followed by addition of L-ascorbic acid (2 mM final concentration). The reaction mixture was stirred for 30 min at room temperature and kept without stirring for an additional 24 h for the complete reaction. Reaction completion was confirmed by the red shift of the AuNP surface plasmon band peak and the corresponding decrease of the ascorbic acid and aurate peaks in the near UV region (<300 nm) using UV-vis absorption spectroscopy. The final sizes were confirmed by TEM measurement.

Ligand Exchange of AuNPs with TA-NTA/TA Ligands

Synthesis of the nitrilotriacetic acid modified thioctic acid (TA-NTA, disulfide ring in close form) solubilizing ligand was as previously described[17,30]. For ligand exchange, the pre-synthesized larger AuNPs were added to an excess TA-NTA/TA mixture[36]. Briefly, 10 mL of as-synthesized citrate-modified AuNPs were mixed with an excess amount of mixed ligand stock solution containing 50% TA and 50% TA-NTA, which had been deprotected from the ester derivative with an equivalent molar concentration of NaOH for an h before mixing with TA. The solution was stirred for 8 h, adjusted to pH 8 by adding NaOH, and the dispersion was purified from free ligands by three cycles of centrifugation using a membrane filtration device (Amicon). For Ni coordination for NTA ligand, excess amount of $NiCl_2$ (500 times of 5 nm AuNP) was directly added to the as-prepared NTA-modified AuNPs and gently stirred for 30 min to promote the interaction between the $Ni^{2+}$ and NTA on the AuNP surface. The $Ni^{2+}$-NTA-modified AuNPs were purified using a centrifugal membrane filter (Amicon) and kept in 4° C. until further required.

Protein Conjugation to NPs: QD-Spike and AuNP-ACE2

Histidine-tagged RBD (RBD-His) was conjugated to the QD surface through coordination between the imidazole units of histidine and the ZnS QD shell. The ACE2-His was conjugated to the NTA on the AuNP after activation with the Nickel ion that simultaneously coordinates the imidazole units of histidine and NTA[15]. For QD-Spike conjugates, the prepared QDs were mixed with stock solution of the histidine-tagged Spike at targeted ratios of protein per QD, and the reaction mixture was adjusted to pH 8 by addition of borate solution (20 mM). After 1 h at room temperature with gentle agitation, BSA (20 μM final concentration) was added to the reaction mixture to prohibit potential non-specific binding. The prepared QD-Spike conjugates were washed using a centrifuge membrane filter (Amicon Ultra) (100 kDa Molecular Cut-off, Millipore. Inc.) to remove small chemicals and the mixture was redispersed in BSA buffer and stored at 4° C. until further use.

For AuNP-ACE2 conjugates, histidine-tagged ACE2 protein was directly added to the Ni-coordinated AuNPs at targeted ratios of ACE2 per AuNP and the mixture was kept at 4° C. for at least 8 h to complete the reaction (see Results section for AuNP/ACE2 ratios studied in this work). BSA (20 μM final concentration) was added to the reaction mixture to prohibit non-specific binding. The prepared AuNP-ACE2 conjugates were washed using a centrifuge membrane filter (100 kDa Molecular Cut-off, Millipore. Inc) to remove low molecular weight impurities and the mixtures were redispersed in borate buffer (with BSA) and stored at 4° C. until further use.

Unconjugated NP Characterization

Three different techniques were used to characterize the QDs and AuNP used in this study: (1) Electronic absorption and PL emission spectra were recorded using a Shimadzu UV-1800 UV-vis spectrophotometer and a Horiba, Inc. fluorometer (excitation at $\lambda$=395 nm), respectively. (2) Dynamic Light Scattering (DLS) was used to measure hydrodynamic size. The samples were transferred into a square shaped capillary and measurements were recorded on a ZetaSizer™ Ultra instrument equipped with a HeNe laser source ($\lambda$=633 nm) (Malvern Instruments Ltd., Worcestershire, UK) and analyzed using Dispersion Technology Software (Malvern Instruments Ltd.) as previously described[18]. (3) Structural characterization and elemental analysis of the as-prepared NPs was carried out using a JEOL 2200-FX analytical high-resolution transmission electron microscope (TEM) with a 200 kV accelerating voltage. TEM samples were prepared by spreading a drop (5-10 μl) containing the NPs onto an ultrathin carbon/holey support film on a 300 mesh Au grid (Ted Pella, Inc.) and letting it dry. The concentration of NPs used for TEM was 50-100 nM. Individual particle sizes were measured using a Gatan Digital Micrograph (Pleasanton, CA); average sizes along with standard deviations were extracted from analysis of at least 50-100 nanoparticles.

Gel Electrophoresis

Conjugation of proteins to $QD_{608}$ or AuNPs was confirmed using an electrophoretic mobility shift assay with a 1% Agarose gel, and 1×TBE buffer at 90 mV[5]. Gel images were taken every 5 min. utilizing a Bio-Rad ChemiDoc XRS+ gel imager under fluorescent light for QDs or Epi-white light for AuNPs. Ratios of RBD to $QD_{608}$ varied from 0 to 16 and ACE2 to AuNP from 1 to 3. The retardation of migration through the gel as the ratio of protein to NP increased confirmed conjugation of the protein to NP.

NP-Based Energy Transfer Assay

QD-RBD conjugates (or QD-S1) were mixed with AuNP-ACE2 conjugates with targeted ratios of AuNP-ACE2 to QD-RBD ranging from 0 to 10. The reaction mixtures were incubated for 2 h at room temperature. The general concentration of QD was approximately 3 nM to 10 nM. A basic buffer containing 20 mM borate and 20 μM BSA was used to stabilize all reactions, unless described separately. The QD fluorescence spectra were obtained at each ratio with 395 nm excitation. The fluorescence images of a series of solutions at increasing AuNP-ACE2 to QD-RBD ratios were taken under excitation with a hand-held UV lamp at 375 nm. For inhibition assays, the desired amount of inhibitor was incubated with QD-RBD for 3 h at room temperature, followed by adding AuNP-ACE2 and incubating for 2 h at room temperature. Fluorescence spectra were obtained in an identical manner as described above.

Quantum Yield Measurements

Fluorescence quantum yields ($\Phi$) were measured at room temperature with fluorescein in 0.1 N NaOH ($\Phi$=0.93)[51] for $QD_{514}$ and $QD_{528}$ or Rhodamine 101 in ethanol ($\Phi$=1.0)[52] for $QD_{608}$ as standards. The obtained fluorescence spectra were corrected using the spectral output of a calibrated light source supplied by the National Bureau of Standards. The parameters in Eq. 1 include the integrated PL intensities of the QD and standard in arbitrary units (A.U.), $PL_{QD}$ and $PL_{st}$, their optical density at excitation wavelength, $OD_{QD}$ and $OD_{st}$, and the refractive indices of their media, $n_{QD}$ and $n_{st}$, respectively[49].

$$\Phi_{QD} = \frac{\int PL_{QD}(\lambda)d\lambda}{\int PL_{st}(\lambda)d\lambda} \left\{ \frac{OD_{st}}{OD_{QD}} \right\} \left\{ \frac{n_{QD}^2}{n_{st}^2} \right\} \Phi_{st} \qquad (1)$$

Generation of Stably Transfected Cell Lines

To create the ACE2-GFP HEK293T cell line, HEK293T cells were seeded into cells in a 6-well plate with 70-80% confluency. For each well, the cells were transfected with 2.5 μg pCMV6-AC-ACE2-GFP plasmid using Lipofectamine 3000 (ThermoFisher). 24 h later, the cells were disassociated with trypsin and transferred into 100 mm dishes. The cells were selected with 1.0 mg/mL G418 for 2-3 weeks. Single colonies were picked into 24-well plates containing 1.0 mL of DMEM with 10% FBS supplemented with 1.0 mg/mL G418. The clones with the brightest GFP signals were picked for propagation.

For the ACE2-Expi293F cell line, Expi293F cells (ThermoFisher) were seeded into cells in a 6-well plate with 70-80% confluency. For each well, the cells were transfected with 2.5 μg pCMV-ACE2-IRES-Puromycin plasmid (Codex BioSolutions) using Lipofectamine 3000. 24 h later, the cells were disassociated with trypsin and transferred into 100-mm dishes. The cells were selected with 1 μg/mL Puromycin for 2-3 weeks. Single colonies were picked into 24-well plates containing 1 mL of DMEM and 10% FBS supplemented with 1 μg/mL Puromycin. Western blot was performed to screen the ACE2 expression clones with an ACE2-specific antibody.

Cell Culture

ACE2-GFP and ACE2-Expi293 cells were cultured using DMEM complete with 10% FBS, and 1% Pen/Strep in large T175 flasks until 80 to 90% confluence prior to seeding in 96 well plates at 25,000 cells per well. Cells were incubated overnight at 37° C. and 5% $CO_2$.

Calu-3 cells were cultured using EMEM complete with 10% FBS, and 1% Pen/Strep in large T175 flasks until 80 to 90% confluence prior to seeding in 96 well plates at 20,000 cells per well. Cells were incubated overnight at 37° C. and 5% $CO_2$.

Immunofluorescence Staining

Cells were washed 3 times with PBS prior to fixation using 4% PFA in PBS with 0.1% BSA for 30 min. Cells were washed 3 times followed by permeabilization with 0.5% saponin in Cell Staining Buffer for 15 min followed by blocking in Cell Staining Buffer for an additional 45 min. Then, cells were incubated with 1:200 mouse anti-ACE2 antibody overnight at 4° C. The next day, cells were washed 3 times with PBS and incubated with 1:1000 goat anti-mouse AlexFluor 488 for 1 h followed by 3×PBS washes. Finally, cells were incubated with Hoechst 33342 to stain the nuclei and HCS Cell Mask Deep Red when required. Cells were washed 3 final times in PBS prior to sealing of the plates for imaging.

QD and Spike Treatment

Prior to treatment with QD-Spike conjugates, cells were washed once with prewarmed Optimem I. Stock QD or recombinant protein solution was diluted directly in Optimem I and 50 μL of QD working solution was added to cells for the indicated amount of time at 37° C. and 5% $CO_2$.

High-Content Imaging and Analysis

Cells were placed into the Opera Phenix (Perkin Elmer) automated confocal imaging system that was preheated to 37° C. A 40× or 63× water immersion objective was used to capture multiple fields per well at a single Z-position. Cells were not washed further prior to imaging. Images were captured with digital phase contrast, Green, and Orange channels. QDs were first exposed to UV light prior to capturing emission using the Orange (λ=570-630 nm) emission bandpass. Images were uploaded into the Columbus Analyzer (Perkin Elmer) and analyzed using custom protocols. Where applicable, the digital phase contrast channel was used to identify the cell bodies, and the Spots were identified in the Green (Cam1: 435-550 nm) and Orange (Cam2: 570-630 nm) channels for ACE2-GFP and $QD_{608}$, respectively. Data was exported into Microsoft Excel and graphs were plotted using Graphpad Prism V8.4.3. For inhibition experiments using neutralizing antibodies or ACE2-Fc, data was normalized to the Optimem I only treated cells (100%, positive control) or $QD_{608}$-RBD treated cells (0%, negative control).

For Dyngo-4a endocytosis inhibition experiments, cells were pre-incubated with 20 μM Dyngo-4a in Optimem I for 15 min. Afterwards, 2× concentrated solutions of Dyngo-4a and $QD_{608}$-RBD was added to an equal volume of Optimem I for a final concentration of 20 μM Dyngo-4a and 10 nM or 20 nM $QD_{608}$-RBD. Imaging began immediately after the addition of $QD_{608}$-RBD with minimal delay. Images were captured every 10 min. for 3 h. For endocytosis experiments using Dyngo-4a, data was normalized to the Optimem I only treated cells (100%, positive control) or $QD_{608}$-RBD treated cells (0%, negative control).

Image montages were constructed using Fiji (NIH). All images for each channel were first stacked before using the auto feature to equally adjust the brightness and contrast across the conditions. For time-lapse videos, images were registered using the StackReg plugin in Fiji and stacks were saved as .avi files.

Single-Molecule Fluorescence Microscopy

Single-molecule imaging experiments were conducted on a custom-built Nikon Ti microscope coupled with a 100× Oil-immersion objective lens (N.A.=1.49), a multi-band dichroic (405/488/561/633 BrightLine quad-band bandpass filter, Semrock, USA) and a piezo z-stage (ASI, USA). The lasers were focused into the back pupil plane of the objective to generate wide-field illumination. Nikon N-STORM module was used to control the angle of the laser beam for generating inclined illumination. The emission was collected by the same objective passing through a quadband bandpass emission filter (FF01-446/523/600/677-25, Semrock, USA) in front of sCMOS camera (Prime 95B, Teledyne Photometrics). The microscope, lasers and the camera were controlled through NIS-Elements (Nikon, USA). 488 nm laser was used to excite the QDs.

Single-Molecule Tracking and Analysis

Single-molecule tracking was performed with custom written MATLAB software[53]. The MATLAB scripts, SLIMFAST/evalSPT, were used to localize and track single molecules. The positions of the diffraction-limited spots in the trajectories were determined with 2D Gaussian fit. A maximal expected diffusion constant was set to connect localizations between consecutive frames.

Mean square displacements (MSDs) were calculated from x,y positions as previously described[54]. It was determined that the instantaneous diffusion coefficients from a linear fit of the initial points of the MSD (between time lag 1 and 5). The MSD curves for all the tracks were computed with @msdanalyzer script[55].

For jump distance analysis, the probability that a particle located at position r at time t in two dimension, will be found at position r' at time t+tau is given by $$\varphi(r, t) = \left(\frac{1}{4\pi Dt}\right)\exp(-r^2/4Dt)$$

where D is the diffusion constant.[56]

In the case of 2D diffusion, the displacement probability was obtained through integrating the above equation over the circular shell of width (dr)

$$p(r, t)dr = dr \int_0^{2\pi} r\varphi(r, t)d\theta = \frac{2\pi r dr}{4\pi Dt}\exp\left(-\frac{r^2}{4Dt}\right)$$

Experimentally, this probability distribution can be approximated by counting the jump distances within respective intervals (r, r+dr) traveled by a single QD during a given time (camera exposure time).

The diffusion coefficient of different species was determined through nonlinear fitting the jump distance histogram with multi-component. F-test were performed to compare the single, two, and three component fitting models.

Statistical Analysis and Illustration

For biochemical assays, all experiments were performed with at least three independent experiments, and the TEM size was analyzed with 50-100 randomly chosen nanoparticles in different images. For cell-based assays, all experiments where statistical analysis were performed included three independent experiments with three independent wells unless otherwise noted. Data shown as mean±standard deviation (S.D.). Concentration-response curves and $EC_{50}$ values were generated using non-linear regression. Illustration in FIG. 6f created using Biorender.

Further Embodiments

It is expected that this technique could be expanded beyond the SARS-CoV-2 Spike to examine interactions mediated by surface proteins (and subunits thereof) of other viruses. This might include, for example, spike proteins of other coronaviruses.

Also contemplated are variations in the RBDs. SEQ ID NO: 11 is a consensus sequence of the RBDs of SEQ ID NOs: 1 through 5, inclusive. It is expected that an RBD closely matching this consensus sequence would operate as desired. For example, a suitable RBD protein might have 95% or greater identity to SEQ ID NO: 11, for example 96%, 97%, 98%, or 99% or greater identity.

CONCLUDING REMARKS

QD nanoparticles labeled with SARS-CoV-2 RBD can act as pseudo-virions that effectively bind ACE2, thus providing an efficient and facile biosensor for biochemical and cell-based assays. Importantly, the QD-RBD constructs and ACE2 enter cells together via dynamin/clathrin-dependent receptor-mediated endocytosis, bound together by the RBD's high affinity to the ACE2 extracellular domain.

The utility of this NP-based sensing probe was explored in multiple ways, demonstrating that biologics such as neutralizing antibodies and recombinant protein can act as very potent inhibitors of the viral Spike. Extrapolating to live virus infection assays, the data supports the idea that the biologics bind the Spike on the surface of the viral particle, preventing its recognition by the ACE2 receptor, and blocking the downstream effects such as membrane fusion[37] and viral endocytosis[23,35,38]. The stably transfected ACE2-GFP cell line has proven an invaluable tool in this approach, and suggests that some appreciable level of ACE2 is required for recognition of the viral particle. However, there may be other viral receptors that participate in viral entry and infection[23,39] and they could be investigated with these QD probes.

Future work involving advanced human airway epithelial tissue models[40] is expected to allow one to probe the spatiotemporal dynamics and features of Spike-ACE2 interactions. These probes can also be used for HTS of potent anti-virals for drug repurposing[41]. Additional studies using full length Spike with cells expressing the host cell protease TMPRSS2 will shed further light on virus-host cell interactions[36]. Altogether, the above work describes a platform technology not only for this SARS-CoV-2 viral pandemic, but also other viruses that have a Spike-mediated cell recognition and entry step as the first step in viral infection[42]. Furthermore, the QD-Spike conjugates may act as highly specific and potent delivery vehicles for drugs and other molecules of therapeutic interest.

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

1. Rothan, H. A. & Byrareddy, S. N. The epidemiology and pathogenesis of coronavirus disease (COVID-19) outbreak. *Journal of autoimmunity,* 102433 (2020).
2. WHO COVID-19 Dashboard. Geneva: World Health Organization, 2020. Available online: https://covid19 who int/
3. Walls, A. C. et al. Structure, function, and antigenicity of the SARS-CoV-2 spike glycoprotein. *Cell* (2020).
4. Kuba, K. et al. A crucial role of angiotensin converting enzyme 2 (ACE2) in SARS coronavirus-induced lung injury. *Nature medicine* 11, 875-879 (2005).
5. Zhou, Y. et al. Network-based drug repurposing for novel coronavirus 2019-nCoV/SARS-CoV-2. *Cell Discov* 6, 1-18 (2020).
6. Bruchez, M., Jr., Moronne, M., Gin, P., Weiss, S. & Alivisatos, A. P. Semiconductor nanocrystals as fluores-cent biological labels. *Science* (New York, N.Y.) 281, 2013-2016, doi:10.1126/science.281.5385.2013 (1998).
7. Alivisatos, P. The use of nanocrystals in biological detection. *Nature biotechnology* 22, 47-52, doi:10.1038/nbt927 (2004).
8. Sapsford, K. E., Pons, T., Medintz, I. L. & Mattoussi, H. Biosensing with luminescent semiconductor quantum dots. *Sensors* 6, 925-953 (2006).
9. Algar, W. R., Susumu, K., Delehanty, J. B. & Medintz, I. L. Semiconductor Quantum Dots in Bioanalysis: Crossing the Valley of Death. *Anal. Chem.* 83, 8826-8837. (2011).
10. Oh, E. et al. Inhibition Assay of Biomolecules based on Fluorescence Resonance Energy Transfer (FRET) between Quantum Dots and Gold Nanoparticles. *Journal of the American Chemical Society* 127, 3270-3271, doi: 10.1021/ja0433323 (2005).
11. Dyadyusha, L. et al. Quenching of CdSe quantum dot emission, a new approach for biosensing. *Chemical Communications,* 3201-3203, doi:10.1039/B500664C (2005).
12. Pons, T. et al. On the quenching of semiconductor quantum dot photoluminescence by proximal gold nanoparticles. *Nano letters* 7, 3157-3164 (2007).
13. Kim, Y-P. et al. Energy transfer-based multiplexed assay of proteases by using gold nanoparticle and quantum dot conjugates on a surface. *Analytical Chemistry* 80, 4634-4641 (2008).
14. Wang, H. et al. SARS coronavirus entry into host cells through a novel clathrin- and caveolae-independent endocytic pathway. *Cell Research* 18, 290-301, doi:10.1038/cr.2008.15 (2008).
15. Udugama, B. et al. Diagnosing COVID-19: The Disease and Tools for Detection. *ACS Nano* 14, 3822-3835, doi: 10.1021/acsnano.0c02624 (2020).
16. Weiss, C. et al. Toward Nanotechnology-Enabled Approaches against the COVID-19 Pandemic. *ACS Nano* 14, 6383-6406, doi:10.1021/acsnano.0c03697 (2020).
17. Breger, J. C. et al. Nanoparticle Size Influences Localized Enzymatic Enhancement—A Case Study with Phosphotriesterase. *Bioconjugate Chemistry* 30, 2060-2074, doi:10.1021/acs.bioconjchem.9b00362 (2019).
18. Oh, E., Susumu, K., Goswami, R. & Mattoussi, H. One-phase synthesis of water-soluble gold nanoparticles with control over size and surface functionalities. *Langmuir* 26, 7604-7613 (2010).
19. Förster, T. Zwischenmolekulare energiewanderung und fluoreszenz. *Annalen der physik* 437, 55-75 (1948).
20. Jennings, T. L., Singh, M. P. & Strouse, G. F. Fluorescent Lifetime Quenching near d=1.5 nm Gold Nanoparticles: Probing NSET Validity. *Journal of the American Chemical Society* 128, 5462-5467, doi:10.1021/ja0583665 (2006).
21. Oh, E. et al. Energy Transfer Sensitization of Luminescent Gold Nanoclusters: More than Just the Classical Forster Mechanism. *Scientific reports* 6, 35538, doi: 10.1038/srep35538 (2016).
22. Uddayasankar, U. & Krull, U. J. Energy Transfer Assays Using Quantum Dot-Gold Nanoparticle Complexes: Optimizing Oligonucleotide Assay Configuration Using Monovalently Conjugated Quantum Dots. *Langmuir* 31, 8194-8204 (2015).
23. Ou, X. et al. Characterization of spike glycoprotein of SARS-CoV-2 on virus entry and its immune cross-reactivity with SARS-CoV. *Nat Commun* 11, 1620, doi: 10.1038/s41467-020-15562-9 (2020).
24. Robertson, M. J., Deane, F. M., Robinson, P. J. & McCluskey, A. Synthesis of Dynole 34-2, Dynole 2-24 and Dyngo 4a for investigating dynamin GTPase. *Nature protocols* 9, 851-870 (2014).

25. Young, L. J., Ströhl, F. & Kaminski, C. F. A Guide to Structured Illumination TIRF Microscopy at High Speed with Multiple Colors. *J Vis Exp*, 53988, doi:10.3791/53988 (2016).

26. Bhatia, D. et al. Quantum dot-loaded monofunctional-ized DNA icosahedra for single-particle tracking of endo-cytic pathways. *Nat Nanotechnol* 11, 1112-1119, doi:10.1038/nnano.2016.150 (2016).

27. Li, D. et al. Extended-resolution structured illumination imaging of endocytic and cytoskeletal dynamics. *Science* (New York, N Y) 349, aab3500, doi:10.1126/science.aab3500 (2015).

28. Jiang, S., Hillyer, C. & Du, L. Neutralizing antibodies against SARS-CoV-2 and other human coronaviruses. *Trends in immunology* (2020).

29. Wang, C. et al. A human monoclonal antibody blocking SARS-CoV-2 infection. *Nat Commun* 11, 1-6 (2020).

30. Ju, B. et al. Potent human neutralizing antibodies elicited by SARS-CoV-2 infection. *BioRxiv* (2020).

31. Maksoudian, C. et al. A Multiparametric Evaluation of Quantum Dot Size and Surface-Grafted Peptide Density on Cellular Uptake and Cytotoxicity. *Bioconjugate Chemistry* 31, 1077-1087, doi:10.1021/acs.bioconjchem.0c00078 (2020).

32. Letko, M., Marzi, A. & Munster, V. Functional assess-ment of cell entry and receptor usage for SARS-CoV-2 and other lineage B betacoronaviruses. *Nature microbi-ology* 5, 562-569 (2020).

33. Chen, L., Li, X., Chen, M., Feng, Y & Xiong, C. The ACE2 expression in human heart indicates new potential mechanism of heart injury among patients infected with SARS-CoV-2. *Cardiovascular research* 116, 1097-1100 (2020).

34. Lukassen, S. et al. SARS-CoV-2 receptor ACE 2 and TMPRSS 2 are primarily expressed in bronchial transient secretory cells. *The EMBO journal* 39, e105114 (2020).

35. Gorshkov, K.; Chen, C. Z.; Bostwick, R.; Rasmussen, L.; Nguyen Tran, B.; Cheng, Y-S.; Xu, M.; Pradhan, M.; Henderson, M.; Zhu, W; Oh, E.; Susumu, K.; Wolak, M.; Shamim, K.; Huang, W; Hu, X.; Shen, M.; Klumpp-Thomas, C.; Itkin, Z.; Shinn, P.; de la Torre, J. C.; Simeonov, A.; Michael, S. G.; Hall, M. D.; Lo, D. C.; Zheng, W The SARS-CoV-2 cytopathic effect is blocked by lysosome alkalizing small molecules ACS Infectious Diseases, 7 (6), 1389-1408 (2020).

36. Hoffmann, M. et al. SARS-CoV-2 cell entry depends on ACE2 and TMPRSS2 and is blocked by a clinically proven protease inhibitor. *Cell* (2020).

37. Wang, X. et al. SARS-CoV-2 infects T lymphocytes through its spike protein-mediated membrane fusion. *Cel-lular & Molecular Immunology*, 1-3 (2020).

38. Yang, N. & Shen, H.-M. Targeting the endocytic path-way and autophagy process as a novel therapeutic strategy in COVID-19. *Int J Biol Sci* 16, 1724 (2020).

39. Yan, S., Sun, H., Bu, X. & Wan, G. New Strategy for COVID-19: An Evolutionary Role for RGD Motif in SARS-CoV-2 and Potential Inhibitors for Virus Infection. *Frontiers in Pharmacology* 11, doi:10.3389/fphar.2020.00912 (2020).

40. Monteil, V. et al. Inhibition of SARS-CoV-2 infections in engineered human tissues using clinical-grade soluble human ACE2. *Cell* (2020).

41. Glebov, O. O. Understanding SARS-CoV-2 endocytosis for COVID-19 drug repurposing. *The FEBS journal*, doi:10.1111/febs.15369 (2020).

42. Gallagher, T. M. & Buchmeier, M. J. Coronavirus spike proteins in viral entry and pathogenesis. *Virology* 279, 371-374 (2001).

43. Susumu, K. et al. Purple-, Blue-, and Green-Emitting Multishell Alloyed Quantum Dots: Synthesis, Character-ization, and Application for Ratiometric Extracellular pH Sensing. *Chemistry of Materials* 29, 7330-7344, doi:10.1021/acs.chemmater.7b02174 (2017).

44. Susumu, K. et al. A new family of pyridine-appended multidentate polymers as hydrophilic surface ligands for preparing stable biocompatible quantum dots. *Chemistry of Materials* 26, 5327-5344 (2014).

45. Chen, O. et al. Synthesis of Metal-Selenide Nanocrystals Using Selenium Dioxide as the Selenium Precursor. *Ang-ewandte Chemie International Edition* 47, 8638-8641, doi:10.1002/anie.200804266 (2008).

46. Jasieniak, J., Smith, L., Van Embden, J., Mulvaney, P. & Califano, M. Re-examination of the size-dependent absorption properties of CdSe quantum dots. *The Journal of Physical Chemistry C* 113, 19468-19474 (2009).

47. Chen, D., Zhao, F., Qi, H., Rutherford, M. & Peng, X. Bright and stable purple/blue emitting CdS/ZnS core/shell nanocrystals grown by thermal cycling using a single-source precursor. *Chemistry of Materials* 22, 1437-1444 (2010).

48. Susumu, K. et al. Multifunctional compact zwitterionic ligands for preparing robust biocompatible semiconductor quantum dots and gold nanoparticles. *Journal of the American Chemical Society* 133, 9480-9496 (2011).

49. Lakowicz, J. R. *Principles of fluorescence spectroscopy*. (Springer science & business media, 2013).

50. Dwyer, C. L. et al. Chemoenzymatic sensitization of DNA photonic wires mediated through quantum dot energy transfer relays. *Chemistry of Materials* 27, 6490-6494 (2015).

51. Magde, D., Wong, R. & Seybold, P. G. Fluorescence quantum yields and their relation to lifetimes of rhod-amine 6G and fluorescein in nine solvents: Improved absolute standards for quantum yields¶. *Photochemistry and photobiology* 75, 327-334 (2002).

52. Karstens, T. & Kobs, K. Rhodamine B and rhodamine 101 as reference substances for fluorescence quantum yield measurements. *The journal of physical chemistry* 84, 1871-1872 (1980).

53. Chen, J. et al. Single-Molecule Dynamics of Enhan-ceosome Assembly in Embryonic Stem Cells. *Cell* 156, 1274-1285, doi:10.1016/j.cell.2014.01.062 (2014).

54. Saxton, M. J. & Jacobson, K. Single-particle tracking: applications to membrane dynamics. *Annual review of biophysics and biomolecular structure* 26, 373-399, doi:10.1146/annurev.biophys.26.1.373 (1997).

55. Tarantino, N. et al. TNF and IL-1 exhibit distinct ubiquitin requirements for inducing NEMO-IKK supra-molecular structures. *J Cell Biol* 204, 231-245, doi:10.1083/jcb.201307172 (2014).

56. Mazza, D., Abernathy, A., Golob, N., Morisaki, T. & McNally, J. G. A benchmark for chromatin binding mea-surements in live cells. *Nucleic acids research* 40, e119, doi:10.1093/nar/gks701 (2012).

BIOLOGICAL SEQUENCES

WT-RBD

SEQ ID NO: 1

RVQPTESIVRFPNITNLCPFGEVFNATRFASVYAWNRKRISNCVADYSVLYNSASFSTF

KCYGVSPTKLNDLCFTNVYADSFVIRGDEVRQIAPGQTGKIADYNYKLPDDFTGCVIAWN

SNNLDSKVGGNYNYLYRLFRKSNLKPFERDISTEIYQAGSTPCNGVEGFNCYFPLQSYGF

QPTNGVGYQPYRVVVLSFELLHAPATVCGPKKSTNLVKNKCVNF

ALPHA-RBD

SEQ ID NO: 2

RVQPTESIVRFPNITNLCPFGEVFNATRFASVYAWNRKRISNCVADYSVLYNSASFSTF

KCYGVSPTKLNDLCFTNVYADSFVIRGDEVRQIAPGQTGKIADYNYKLPDDFTGCVIAWN

SNNLDSKVGGNYNYLYRLFRKSNLKPFERDISTEIYQAGSTPCNGVEGFNCYFPLQSYGF

QPTYGVGYQPYRVVVLSFELLHAPATVCGPKKSTNLVKNKCVNF

BETA-RBD

SEQ ID NO: 3

RVQPTESIVRFPNITNLCPFGEVFNATRFASVYAWNRKRISNCVADYSVLYNSASFSTF

KCYGVSPTKLNDLCFTNVYADSFVIRGDEVRQIAPGQTGNIADYNYKLPDDFTGCVIAWN

SNNLDSKVGGNYNYLYRLFRKSNLKPFERDISTEIYQAGSTPCNGVKGFNCYFPLQSYGF

QPTYGVGYQPYRVVVLSFELLHAPATVCGPKKSTNLVKNKCVNF

GAMMA-RBD

SEQ ID NO: 4

RVQPTESIVRFPNITNLCPFGEVFNATRFASVYAWNRKRISNCVADYSVLYNSASFSTF

KCYGVSPTKLNDLCFTNVYADSFVIRGDEVRQIAPGQTGTIADYNYKLPDDFTGCVIAWN

SNNLDSKVGGNYNYLYRLFRKSNLKPFERDISTEIYQAGSTPCNGVKGFNCYFPLQSYGF

QPTYGVGYQPYRVVVLSFELLHAPATVCGPKKSTNLVKNKCVNF

DELTA-RBD

SEQ ID NO: 5

RVQPTESIVRFPNITNLCPFGEVFNATRFASVYAWNRKRISNCVADYSVLYNSASFSTF

KCYGVSPTKLNDLCFTNVYADSFVIRGDEVRQIAPGQTGKIADYNYKLPDDFTGCVIAWN

SNNLDSKVGGNYNYRYRLFRKSNLKPFERDISTEIYQAGSKPCNGVEGFNCYFPLQSYGF

QPTNGVGYQPYRVVVLSFELLHAPATVCGPKKSTNLVKNKCVNF

WT-FULL

SEQ ID NO: 6

VNLTTRTQLPPAYTNSFTRGVYYPDKVFRSSVLHSTQDLFLPFFSNVTWFHAIHVSG

TNGTKRFDNPVLPFNDGVYFASTEKSNIIRGWIFGTTLDSKTQSLLIVNNATNVVIKVCEFQ

FCNDPFLGVYYHKNNKSWMESEFRVYSSANNCTFEYVSQPFLMDLEGKQGNFKNLREF

VFKNIDGYFKIYSKHTPINLVRDLPQGFSALEPLVDLPIGINITRFQTLLALHRSYLTPGDSS

SGWTAGAAAYYVGYLQPRTFLLKYNENGTITDAVDCALDPLSETKCTLKSFTVEKGIYQT

SNFRVQPTESIVRFPNITNLCPFGEVFNATRFASVYAWNRKRISNCVADYSVLYNSASFSTFK

CYGVSPTKLNDLCFTNVYADSFVIRGDEVRQIAPGQTGKIADYNYKLPDDFTGCVIAWNS

NNLDSKVGGNYNYLYRLFRKSNLKPFERDISTEIYQAGSTPCNGVEGFNCYFPLQSYGFQ

PTNGVGYQPYRVVVLSFELLHAPATVCGPKKSTNLVKNKCVNFNFNGLTGTGVLTESNKK

FLPFQQFGRDIADTTDAVRDPQTLEILDITPCSFGGVSVITPGTNTSNQVAVLYQDVNCTEV

PVAIHADQLTPTWRVYSTGSNVFQTRAGCLIGAEHVNNSYECDIPIGAGICASYQTQTNSP

RAAASVASQSIIAYTMSLGAENSVAYSNNSIAIPTNFTISVTTEILPVSMTKTSVDCTMYICGD

STECSNLLLQYGSFCTQLNRALTGIAVEQDKNTQEVFAQVKQIYKTPPIKDFGGFNFSQILP

DPSKPSKRSPIEDLLFNKVTLADAGFIKQYGDCLGDIAARDLICAQKFNGLTVLPPLLTDE

-continued

BIOLOGICAL SEQUENCES

MIAQYTSALLAGTITSGWTFGAGPALQIPFPMQMAYRFNGIGVTQNVLYENQKLIANQFN

SAIGKIQDSLSSTPSALGKLQDVVNQNAQALNTLVKQLSSNFGAISSVLNDILSRLDPPEAE

VQIDRLITGRLQSLQTYVTQQLIRAAEIRASANLAATKMSECVLGQSKRVDFCGKGYHLM

SFPQSAPHGVVFLHVTYVPAQEKNFTTAPAICHDGKAHFPREGVFVSNGTHWFVTQRNFY

EPQIITTDNTFVSGNCDVVIGIVNNTVYDPLQPELDSFKEELDKYFKNHTSPDVDLGDISGI

NASVVNIQKEIDRLNEVAKNLNESLIDLQELGKYEQYIKWP

ALPHA-FULL
SEQ ID NO: 7
VNLTTRTQLPPAYTNSFTRGVYYPDKVFRSSVLHSTQDLFLPFFSNVTWFHATSGTN

GTKRFDNPVLPFNDGVYFASTEKSNIIRGWIFGTTLDSKTQSLLIVNNATNVVIKVCEFQFC

NDPFLGVYHKNNKSWMESEFRVYSSANNCTFEYVSQPFLMDLEGKQGNFKNLREFVFK

NIDGYFKIYSKHTPINLVRDLPQGFSALEPLVDLPIGINITRFQTLLALHRSYLTPGDSSSGW

TAGAAAYYVGYLQPRTFLLKYNENGTITDAVDCALDPLSETKCTLKSFTVEKGIYQTSNFR

VQPTESIVRFPNITNLCPFGEVFNATRFASVYAWNRKRISNCVADYSVLYNSASFSTFKCYGV

SPTKLNDLCFTNVYADSFVIRGDEVRQIAPGQTGKIADYNYKLPDDFTGCVIAWNSNNLD

SKVGGNYNYLYRLFRKSNLKPFERDISTEIYQAGSTPCNGVEGFNCYFPLQSYGFQPTYGV

GYQPYRVVVLSFELLHAPATVCGPKKSTNLVKNKCVNFNFNGLTGTGVLTESNKKFLPFQ

QFGRDIDDTTDAVRDPQTLEILDITPCSFGGVSVITPGTNTSNQVAVLYQGVNCTEVPVAIH

ADQLTPTWRVYSTGSNVFQTRAGCLIGAEHVNNSYECDIPIGAGICASYQTQTNSHRAAA

SVASQSIIAYTMSLGAENSVAYSNNSIAIPINFTISVTTEILPVSMTKTSVDCTMYICGDSTECS

NLLLQYGSFCTQLNRALTGIAVEQDKNTQEVFAQVKQIYKTPPIKDFGGFNFSQILPDPSKP

SKRSPIEDLLFNKVTLADAGFIKQYGDCLGDIAARDLICAQKFNGLTVLPPLLTDEMIAQY

TSALLAGTITSGWTFGAGPALQIPFPMQMAYRFNGIGVTQNVLYENQKLIANQFNSAIGKI

QDSLSSTPSALGKLQDVVNQNAQALNTLVKQLSSNFGAISSVLNDILARLDPPEAEVQIDR

LITGRLQSLQTYVTQQLIRAAEIRASANLAATKMSECVLGQSKRVDFCGKGYHLMSFPQS

APHGVVFLHVTYVPAQEKNFTTAPAICHDGKAHFPREGVFVSNGTHWFVTQRNFYEPQII

TTHNTFVSGNCDVVIGIVNNTVYDPLQPELDSFKEELDKYFKNHTSPDVDLGDISGINASV

VNIQKEIDRLNEVAKNLNESLIDLQELGKYEQYIKWP

BETA-FULL
SEQ ID NO: 8
VNFTTRTQLPPAYTNSFTRGVYYPDKVFRSSVLHSTQDLFLPFFSNVTWFHAIHVSG

TNGTKRFANPVLPFNDGVYFASTEKSNIIRGWIFGTTLDSKTQSLLIVNNATNVVIKVCEFQ

FCNDPFLGVYYHKNNKSWMESEFRVYSSANNCTFEYVSQPFLMDLEGKQGNFKNLREF

VFKNIDGYFKIYSKHTPINLVRGLPQGFSALEPLVDLPIGINITRFQTLLALHISYLTPGDSSS

GWTAGAAAYYVGYLQPRTFLLKYNENGTITDAVDCALDPLSETKCTLKSFTVEKGIYQTS

NFRVQPTESIVRFPNITNLCPFGEVFNATRFASVYAWNRKRISNCVADYSVLYNSASFSTFKC

YGVSPTKLNDLCFTNVYADSFVIRGDEVRQIAPGQTGNIADYNYKLPDDFTGCVIAWNSN

NLDSKVGGNYNYLYRLFRKSNLKPFERDISTEIYQAGSTPCNGVKGFNCYFPLQSYGFQP

TYGVGYQPYRVVVLSFELLHAPATVCGPKKSTNLVKNKCVNFNFNGLTGTGVLTESNKKF

LPFQQFGRDIADTTDAVRDPQTLEILDITPCSFGGVSVITPGTNTSNQVAVLYQGVNCTEVP

-continued

BIOLOGICAL SEQUENCES

VAIHADQLTPTWRVYSTGSNVFQTRAGCLIGAEHVNNSYECDIPIGAGICASYQTQTNSPR

AAASVASQSIIAYTMSLGVENSVAYSNNSIAIPTNFTISVTTEILPVSMTKTSVDCTMYICGDS

TECSNLLLQYGSFCTQLNRALTGIAVEQDKNTQEVFAQVKQIYKTPPIKDFGGFNFSQILP

DPSKPSKRSPIEDLLFNKVTLADAGFIKQYGDCLGDIAARDLICAQKFNGLTVLPPLLTDE

MIAQYTSALLAGTITSGWTFGAGPALQIPFPMQMAYRFNGIGVTQNVLYENQKLIANQFN

SAIGKIQDSLSSTPSALGKLQDVVNQNAQALNTLVKQLSSNFGAISSVLNDILSRLDPPEAE

VQIDRLITGRLQSLQTYVTQQLIRAAEIRASANLAATKMSECVLGQSKRVDFCGKGYHLM

SFPQSAPHGVVFLHVTYVPAQEKNFTTAPAICHDGKAHFPREGVFVSNGTHWFVTQRNFY

EPQIITTDNTFVSGNCDVVIGIVNNTVYDPLQPELDSFKEELDKYFKNHTSPDVDLGDISGI

NASVVNIQKEIDRLNEVAKNLNESLIDLQELGKYEQYIKWP

GAMMA-FULL

SEQ ID NO: 9

VNFTNRTQLPSAYTNSFTRGVYYPDKVFRSSVLHSTQDLFLPFFSNVTWFHAIHVSG

TNGTKRFDNPVLPFNDGVYFASTEKSNIIRGWIFGTTLDSKTQSLLIVNNATNVVIKVCEFQ

FCNYPFLGVYYHKNNKSWMESEFRVYSSANNCTFEYVSQPFLMDLEGKQGNFKNLSEFV

FKNIDGYFKIYSKHTPINLVRDLPQGFSALEPLVDLPIGINITRFQTLLALHRSYLTPGDSSS

GWTAGAAAYYVGYLQPRTFLLKYNENGTITDAVDCALDPLSETKCTLKSFTVEKGIYQTS

NFRVQPTESIVRFPNITNLCPFGEVFNATRFASVYAWNRKRISNCVADYSVLYNSASFSTFKC

YGVSPTKLNDLCFTNVYADSFVIRGDEVRQIAPGQTGTIADYNYKLPDDFTGCVIAWNSN

NLDSKVGGNYNYLYRLFRKSNLKPFERDISTEIYQAGSTPCNGVKGFNCYFPLQSYGFQP

TYGVGYQPYRVVVLSFELLHAPATVCGPKKSTNLVKNKCVNFNFNGLTGTGVLTESNKKF

LPFQQFGRDIADTTDAVRDPQTLEILDITPCSFGGVSVITPGTNTSNQVAVLYQGVNCTEVP

VAIHADQLTPTWRVYSTGSNVFQTRAGCLIGAEYVNNSYECDIPIGAGICASYQTQTNSPR

AAASVASQSIIAYTMSLGAENSVAYSNNSIAIPTNFTISVTTEILPVSMTKTSVDCTMYICGDS

TECSNLLLQYGSFCTQLNRALTGIAVEQDKNTQEVFAQVKQIYKTPPIKDFGGFNFSQILP

DPSKPSKRSPIEDLLFNKVTLADAGFIKQYGDCLGDIAARDLICAQKFNGLTVLPPLLTDE

MIAQYTSALLAGTITSGWTFGAGPALQIPFPMQMAYRFNGIGVTQNVLYENQKLIANQFN

SAIGKIQDSLSSTPSALGKLQDVVNQNAQALNTLVKQLSSNFGAISSVLNDILSRLDPPEAE

VQIDRLITGRLQSLQTYVTQQLIRAAEIRASANLAAIKMSECVLGQSKRVDFCGKGYHLMS

FPQSAPHGVVFLHVTYVPAQEKNFTTAPAICHDGKAHFPREGVFVSNGTHWFVTQRNFY

EPQIITTDNTFVSGNCDVVIGIVNNTVYDPLQPELDSFKEELDKYFKNHTSPDVDLGDISGI

NASFVNIQKEIDRLNEVAKNLNESLIDLQELGKYEQYIKWP

DELTA-FULL

SEQ ID NO: 10

VNLRTRTQLPPAYTNSFTRGVYYPDKVFRSSVLHSTQDLFLPFFSNVTWFHAIHVSG

TNGTKRFDNPVLPFNDGVYFASTEKSNIIRGWIFGTTLDSKTQSLLIVNNATNVVIKVCEFQ

FCNDPFLDVYYHKNNKSWMESGVYSSANNCTFEYVSQPFLMDLEGKQGNFKNLREFVF

KNIDGYFKIYSKHTPINLVRDLPQGFSALEPLVDLPIGINITRFQTLLALHRSYLTPGDSSSG

WTAGAAAYYVGYLQPRTFLLKYNENGTITDAVDCALDPLSETKCTLKSFTVEKGIYQTSN

FRVQPTESIVRFPNITNLCPFGEVFNATRFASVYAWNRKRISNCVADYSVLYNSASFSTFKCY

GVSPTKLNDLCFTNVYADSFVIRGDEVRQIAPGQTGKIADYNYKLPDDFTGCVIAWNSNN

-continued

BIOLOGICAL SEQUENCES

LDSKVGGNYNYRYRLFRKSNLKPFERDISTEIYQAGSKPCNGVEGFNCYFPLQSYGFQPT

NGVGYQPYRVVVLSFELLHAPATVCGPKKSTNLVKNKCVNFNFNGLTGTGVLTESNKKFL

PFQQFGRDIADTTDAVRDPQTLEILDITPCSFGGVSVITPGTNTSNQVAVLYQGVNCTEVPV

AIHADQLTPTWRVYSTGSNVFQTRAGCLIGAEHVNNSYECDIPIGAGICASYQTQTNSRRA

AASVASQSIIAYTMSLGAENSVAYSNNSIAIPTNFTISVTTEILPVSMTKTSVDCTMYICGDST

ECSNLLLQYGSFCTQLNRALTGIAVEQDKNTQEVFAQVKQIYKTPPIKDFGGFNFSQILPDP

SKPSKRSPIEDLLFNKVTLADAGFIKQYGDCLGDIAARDLICAQKFNGLTVLPPLLTDEMI

AQYTSALLAGTITSGWTFGAGPALQIPFPMQMAYRFNGIGVTQNVLYENQKLIANQFNSA

IGKIQDSLSSTPSALGKLQNVVNQNAQALNTLVKQLSSNFGAISSVLNDILSRLDPPEAEVQI

DRLITGRLQSLQTYVTQQLIRAAEIRASANLAATKMSECVLGQSKRVDFCGKGYHLMSFP

QSAPHGVVFLHVTYVPAQEKNFTTAPAICHDGKAHFPREGVFVSNGTHWFVTQRNFYEP

QIITTDNTFVSGNCDVVIGIVNNTVYDPLQPELDSFKEELDKYFKNHTSPDVDLGDISGINA

SVVNIQKEIDRLNEVAKNLNESLIDLQELGKYEQYIKWP

RBD CONSENSUS
                                                     SEQ ID NO: 11
RVQPTESIVRFPNITNLCPFGEVFNATRFASVYAWNRKRISNCVADYSYLYNSASFSTF

KCYGVSPTKLNDLCFTNVYADSFVIRGDEVRQIAPGQTGxIADYNYKLPDDFTGCVIAWNS

NNLDSKVGGNYNYxYRLFRKSNLKPFERDISTEIYQAGSxPCNGVxGFNCYFPLQSYGFQP

TxGVGYQPYRWVLSFELLITAPATVCGPKKSINLVKNKCVNF

What is claimed is:

1. A method of assaying inhibitors of Spike protein binding, comprising:

providing a quantum dot labeled with a protein comprising SARS-COV-2 Spike protein receptor binding domain (RBD) comprising a Spike protein trimer;

contacting the quantum dot with a gold nanoparticle conjugated to angiotensin converting enzyme 2 (ACE2) in the presence of a possible inhibitor of binding between the RBD and ACE2; and measuring energy transfer between the quantum dot and the gold nanoparticle, wherein the energy transfer when compared to a control indicates binding between the RBD and ACE2 and thereby possible inhibition thereof.

2. The method of claim 1, wherein the possible inhibitor is an antibody against the SARS-COV-2 Spike protein.

3. The method of claim 2, wherein the possible inhibitor is a drug.

4. The method of claim 1, wherein said protein comprising RBD is a Histidine-tagged RBD (RBD-His).

5. The method of claim 1, wherein said RBD has at least 98% sequence identity to SEQ ID NO: 11.

* * * * *

SEQUENCE LISTING

<160> NUMBER OF SEQ ID NOS: 11

<210> SEQ ID NO 1
<211> LENGTH: 223
<212> TYPE: PRT
<213> ORGANISM: SARS-CoV-2

<400> SEQUENCE: 1

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys

-continued

```
        130               135               140

Pro Phe Glu Arg Asp Ile Ser Thr Glu Ile Tyr Gln Ala Gly Ser Thr
145               150               155               160

Pro Cys Asn Gly Val Glu Gly Phe Asn Cys Tyr Phe Pro Leu Gln Ser
                  165               170               175

Tyr Gly Phe Gln Pro Thr Asn Gly Val Gly Tyr Gln Pro Tyr Arg Val
                  180               185               190

Val Val Leu Ser Phe Glu Leu Leu His Ala Pro Ala Thr Val Cys Gly
              195               200               205

Pro Lys Lys Ser Thr Asn Leu Val Lys Asn Lys Cys Val Asn Phe
          210               215               220

<210> SEQ ID NO 2
<211> LENGTH: 223
<212> TYPE: PRT
<213> ORGANISM: SARS-CoV-2

<400> SEQUENCE: 2

Arg Val Gln Pro Thr Glu Ser Ile Val Arg Phe Pro Asn Ile Thr Asn
1               5               10               15

Leu Cys Pro Phe Gly Glu Val Phe Asn Ala Thr Arg Phe Ala Ser Val
                  20               25               30

Tyr Ala Trp Asn Arg Lys Arg Ile Ser Asn Cys Val Ala Asp Tyr Ser
              35               40               45

Val Leu Tyr Asn Ser Ala Ser Phe Ser Thr Phe Lys Cys Tyr Gly Val
          50               55               60

Ser Pro Thr Lys Leu Asn Asp Leu Cys Phe Thr Asn Val Tyr Ala Asp
65               70               75               80

Ser Phe Val Ile Arg Gly Asp Glu Val Arg Gln Ile Ala Pro Gly Gln
                  85               90               95

Thr Gly Lys Ile Ala Asp Tyr Asn Tyr Lys Leu Pro Asp Asp Phe Thr
                  100               105               110

Gly Cys Val Ile Ala Trp Asn Ser Asn Asn Leu Asp Ser Lys Val Gly
              115               120               125

Gly Asn Tyr Asn Tyr Leu Tyr Arg Leu Phe Arg Lys Ser Asn Leu Lys
          130               135               140

Pro Phe Glu Arg Asp Ile Ser Thr Glu Ile Tyr Gln Ala Gly Ser Thr
145               150               155               160

Pro Cys Asn Gly Val Glu Gly Phe Asn Cys Tyr Phe Pro Leu Gln Ser
                  165               170               175

Tyr Gly Phe Gln Pro Thr Tyr Gly Val Gly Tyr Gln Pro Tyr Arg Val
                  180               185               190

Val Val Leu Ser Phe Glu Leu Leu His Ala Pro Ala Thr Val Cys Gly
              195               200               205

Pro Lys Lys Ser Thr Asn Leu Val Lys Asn Lys Cys Val Asn Phe
          210               215               220

<210> SEQ ID NO 3
<211> LENGTH: 223
<212> TYPE: PRT
<213> ORGANISM: SARS-CoV-2

<400> SEQUENCE: 3

Arg Val Gln Pro Thr Glu Ser Ile Val Arg Phe Pro Asn Ile Thr Asn
1               5               10               15

Leu Cys Pro Phe Gly Glu Val Phe Asn Ala Thr Arg Phe Ala Ser Val
```

-continued

```
                20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Asn Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Lys Gly Phe Asn Cys Tyr Phe Pro Leu Gln Ser
            165                 170                 175

Tyr Gly Phe Gln Pro Thr Tyr Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220

<210> SEQ ID NO 4
<211> LENGTH: 223
<212> TYPE: PRT
<213> ORGANISM: SARS-CoV-2

<400> SEQUENCE: 4

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Thr Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Lys Gly Phe Asn Cys Tyr Phe Pro Leu Gln Ser
            165                 170                 175
```

-continued

Tyr Gly Phe Gln Pro Thr Tyr Gly Val Gly Tyr Gln Pro Tyr Arg Val
            180                     185                     190

Val Val Leu Ser Phe Glu Leu Leu His Ala Pro Ala Thr Val Cys Gly
            195                     200                     205

Pro Lys Lys Ser Thr Asn Leu Val Lys Asn Lys Cys Val Asn Phe
    210                     215                     220

<210> SEQ ID NO 5
<211> LENGTH: 223
<212> TYPE: PRT
<213> ORGANISM: SARS-CoV-2

<400> SEQUENCE: 5

Arg Val Gln Pro Thr Glu Ser Ile Val Arg Phe Pro Asn Ile Thr Asn
1                   5                      10                      15

Leu Cys Pro Phe Gly Glu Val Phe Asn Ala Thr Arg Phe Ala Ser Val
            20                      25                      30

Tyr Ala Trp Asn Arg Lys Arg Ile Ser Asn Cys Val Ala Asp Tyr Ser
            35                      40                      45

Val Leu Tyr Asn Ser Ala Ser Phe Ser Thr Phe Lys Cys Tyr Gly Val
    50                      55                      60

Ser Pro Thr Lys Leu Asn Asp Leu Cys Phe Thr Asn Val Tyr Ala Asp
65                      70                      75                      80

Ser Phe Val Ile Arg Gly Asp Glu Val Arg Gln Ile Ala Pro Gly Gln
                85                      90                      95

Thr Gly Lys Ile Ala Asp Tyr Asn Tyr Lys Leu Pro Asp Asp Phe Thr
            100                     105                     110

Gly Cys Val Ile Ala Trp Asn Ser Asn Asn Leu Asp Ser Lys Val Gly
            115                     120                     125

Gly Asn Tyr Asn Tyr Arg Tyr Arg Leu Phe Arg Lys Ser Asn Leu Lys
            130                     135                     140

Pro Phe Glu Arg Asp Ile Ser Thr Glu Ile Tyr Gln Ala Gly Ser Lys
145                     150                     155                     160

Pro Cys Asn Gly Val Glu Gly Phe Asn Cys Tyr Phe Pro Leu Gln Ser
                165                     170                     175

Tyr Gly Phe Gln Pro Thr Asn Gly Val Gly Tyr Gln Pro Tyr Arg Val
            180                     185                     190

Val Val Leu Ser Phe Glu Leu Leu His Ala Pro Ala Thr Val Cys Gly
            195                     200                     205

Pro Lys Lys Ser Thr Asn Leu Val Lys Asn Lys Cys Val Asn Phe
    210                     215                     220

<210> SEQ ID NO 6
<211> LENGTH: 1198
<212> TYPE: PRT
<213> ORGANISM: SARS-CoV-2

<400> SEQUENCE: 6

Val Asn Leu Thr Thr Arg Thr Gln Leu Pro Pro Ala Tyr Thr Asn Ser
1                   5                      10                      15

Phe Thr Arg Gly Val Tyr Tyr Pro Asp Lys Val Phe Arg Ser Ser Val
            20                      25                      30

Leu His Ser Thr Gln Asp Leu Phe Leu Pro Phe Phe Ser Asn Val Thr
            35                      40                      45

Trp Phe His Ala Ile His Val Ser Gly Thr Asn Gly Thr Lys Arg Phe
    50                      55                      60

-continued

```
Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr Tyr His Lys Asn Asn Lys Ser Trp Met Glu Ser Glu Phe Arg Val
    130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
                180                 185                 190

Thr Pro Ile Asn Leu Val Arg Asp Leu Pro Gln Gly Phe Ser Ala Leu
            195                 200                 205

Glu Pro Leu Val Asp Leu Pro Ile Gly Ile Asn Ile Thr Arg Phe Gln
    210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
                245                 250                 255

Pro Arg Thr Phe Leu Leu Lys Tyr Asn Glu Asn Gly Thr Ile Thr Asp
            260                 265                 270

Ala Val Asp Cys Ala Leu Asp Pro Leu Ser Glu Thr Lys Cys Thr Leu
        275                 280                 285

Lys Ser Phe Thr Val Glu Lys Gly Ile Tyr Gln Thr Ser Asn Phe Arg
    290                 295                 300

Val Gln Pro Thr Glu Ser Ile Val Arg Phe Pro Asn Ile Thr Asn Leu
305                 310                 315                 320

Cys Pro Phe Gly Glu Val Phe Asn Ala Thr Arg Phe Ala Ser Val Tyr
                325                 330                 335

Ala Trp Asn Arg Lys Arg Ile Ser Asn Cys Val Ala Asp Tyr Ser Val
            340                 345                 350

Leu Tyr Asn Ser Ala Ser Phe Ser Thr Phe Lys Cys Tyr Gly Val Ser
    355                 360                 365

Pro Thr Lys Leu Asn Asp Leu Cys Phe Thr Asn Val Tyr Ala Asp Ser
    370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
                405                 410                 415

Cys Val Ile Ala Trp Asn Ser Asn Asn Leu Asp Ser Lys Val Gly Gly
            420                 425                 430

Asn Tyr Asn Tyr Leu Tyr Arg Leu Phe Arg Lys Ser Asn Leu Lys Pro
        435                 440                 445

Phe Glu Arg Asp Ile Ser Thr Glu Ile Tyr Gln Ala Gly Ser Thr Pro
    450                 455                 460

Cys Asn Gly Val Glu Gly Phe Asn Cys Tyr Phe Pro Leu Gln Ser Tyr
465                 470                 475                 480

Gly Phe Gln Pro Thr Asn Gly Val Gly Tyr Gln Pro Tyr Arg Val Val
```

-continued

```
              485             490             495

Val Leu Ser Phe Glu Leu Leu His Ala Pro Ala Thr Val Cys Gly Pro
              500             505             510

Lys Lys Ser Thr Asn Leu Val Lys Asn Lys Cys Val Asn Phe Asn Phe
              515             520             525

Asn Gly Leu Thr Gly Thr Gly Val Leu Thr Glu Ser Asn Lys Lys Phe
              530             535             540

Leu Pro Phe Gln Gln Phe Gly Arg Asp Ile Ala Asp Thr Thr Asp Ala
545             550             555             560

Val Arg Asp Pro Gln Thr Leu Glu Ile Leu Asp Ile Thr Pro Cys Ser
              565             570             575

Phe Gly Gly Val Ser Val Ile Thr Pro Gly Thr Asn Thr Ser Asn Gln
              580             585             590

Val Ala Val Leu Tyr Gln Asp Val Asn Cys Thr Glu Val Pro Val Ala
              595             600             605

Ile His Ala Asp Gln Leu Thr Pro Thr Trp Arg Val Tyr Ser Thr Gly
              610             615             620

Ser Asn Val Phe Gln Thr Arg Ala Gly Cys Leu Ile Gly Ala Glu His
625             630             635             640

Val Asn Asn Ser Tyr Glu Cys Asp Ile Pro Ile Gly Ala Gly Ile Cys
              645             650             655

Ala Ser Tyr Gln Thr Gln Thr Asn Ser Pro Arg Ala Ala Ala Ser Val
              660             665             670

Ala Ser Gln Ser Ile Ile Ala Tyr Thr Met Ser Leu Gly Ala Glu Asn
              675             680             685

Ser Val Ala Tyr Ser Asn Asn Ser Ile Ala Ile Pro Thr Asn Phe Thr
              690             695             700

Ile Ser Val Thr Thr Glu Ile Leu Pro Val Ser Met Thr Lys Thr Ser
705             710             715             720

Val Asp Cys Thr Met Tyr Ile Cys Gly Asp Ser Thr Glu Cys Ser Asn
              725             730             735

Leu Leu Leu Gln Tyr Gly Ser Phe Cys Thr Gln Leu Asn Arg Ala Leu
              740             745             750

Thr Gly Ile Ala Val Glu Gln Asp Lys Asn Thr Gln Glu Val Phe Ala
              755             760             765

Gln Val Lys Gln Ile Tyr Lys Thr Pro Pro Ile Lys Asp Phe Gly Gly
              770             775             780

Phe Asn Phe Ser Gln Ile Leu Pro Asp Pro Ser Lys Pro Ser Lys Arg
785             790             795             800

Ser Pro Ile Glu Asp Leu Leu Phe Asn Lys Val Thr Leu Ala Asp Ala
              805             810             815

Gly Phe Ile Lys Gln Tyr Gly Asp Cys Leu Gly Asp Ile Ala Ala Arg
              820             825             830

Asp Leu Ile Cys Ala Gln Lys Phe Asn Gly Leu Thr Val Leu Pro Pro
              835             840             845

Leu Leu Thr Asp Glu Met Ile Ala Gln Tyr Thr Ser Ala Leu Leu Ala
              850             855             860

Gly Thr Ile Thr Ser Gly Trp Thr Phe Gly Ala Gly Pro Ala Leu Gln
865             870             875             880

Ile Pro Phe Pro Met Gln Met Ala Tyr Arg Phe Asn Gly Ile Gly Val
              885             890             895

Thr Gln Asn Val Leu Tyr Glu Asn Gln Lys Leu Ile Ala Asn Gln Phe
              900             905             910
```

-continued

```
Asn Ser Ala Ile Gly Lys Ile Gln Asp Ser Leu Ser Ser Thr Pro Ser
        915             920             925

Ala Leu Gly Lys Leu Gln Asp Val Val Asn Gln Asn Ala Gln Ala Leu
        930             935             940

Asn Thr Leu Val Lys Gln Leu Ser Ser Asn Phe Gly Ala Ile Ser Ser
945             950             955             960

Val Leu Asn Asp Ile Leu Ser Arg Leu Asp Pro Pro Glu Ala Glu Val
            965             970             975

Gln Ile Asp Arg Leu Ile Thr Gly Arg Leu Gln Ser Leu Gln Thr Tyr
            980             985             990

Val Thr Gln Gln Leu Ile Arg Ala  Ala Glu Ile Arg Ala  Ser Ala Asn
            995             1000            1005

Leu Ala  Ala Thr Lys Met Ser  Glu Cys Val Leu Gly  Gln Ser Lys
        1010            1015            1020

Arg Val  Asp Phe Cys Gly Lys  Gly Tyr His Leu Met  Ser Phe Pro
        1025            1030            1035

Gln Ser  Ala Pro His Gly Val  Val Phe Leu His Val  Thr Tyr Val
        1040            1045            1050

Pro Ala  Gln Glu Lys Asn Phe  Thr Thr Ala Pro Ala  Ile Cys His
        1055            1060            1065

Asp Gly  Lys Ala His Phe Pro  Arg Glu Gly Val Phe  Val Ser Asn
        1070            1075            1080

Gly Thr  His Trp Phe Val Thr  Gln Arg Asn Phe Tyr  Glu Pro Gln
        1085            1090            1095

Ile Ile  Thr Thr Asp Asn Thr  Phe Val Ser Gly Asn  Cys Asp Val
        1100            1105            1110

Val Ile  Gly Ile Val Asn Asn  Thr Val Tyr Asp Pro  Leu Gln Pro
        1115            1120            1125

Glu Leu  Asp Ser Phe Lys Glu  Glu Leu Asp Lys Tyr  Phe Lys Asn
        1130            1135            1140

His Thr  Ser Pro Asp Val Asp  Leu Gly Asp Ile Ser  Gly Ile Asn
        1145            1150            1155

Ala Ser  Val Val Asn Ile Gln  Lys Glu Ile Asp Arg  Leu Asn Glu
        1160            1165            1170

Val Ala  Lys Asn Leu Asn Glu  Ser Leu Ile Asp Leu  Gln Glu Leu
        1175            1180            1185

Gly Lys  Tyr Glu Gln Tyr Ile  Lys Trp Pro
        1190            1195
```

```
<210> SEQ ID NO 7
<211> LENGTH: 1195
<212> TYPE: PRT
<213> ORGANISM: SARS-CoV-2

<400> SEQUENCE: 7

Val Asn Leu Thr Thr Arg Thr Gln Leu Pro Pro Ala Tyr Thr Asn Ser
1               5               10              15

Phe Thr Arg Gly Val Tyr Tyr Pro Asp Lys Val Phe Arg Ser Ser Val
            20              25              30

Leu His Ser Thr Gln Asp Leu Phe Leu Pro Phe Phe Ser Asn Val Thr
        35              40              45

Trp Phe His Ala Ile Ser Gly Thr Asn Gly Thr Lys Arg Phe Asp Asn
    50              55              60

Pro Val Leu Pro Phe Asn Asp Gly Val Tyr Phe Ala Ser Thr Glu Lys
```

-continued

```
65                  70                  75                  80

Ser Asn Ile Ile Arg Gly Trp Ile Phe Gly Thr Thr Leu Asp Ser Lys
                85                  90                  95

Thr Gln Ser Leu Leu Ile Val Asn Asn Ala Thr Asn Val Val Ile Lys
            100                 105                 110

Val Cys Glu Phe Gln Phe Cys Asn Asp Pro Phe Leu Gly Val Tyr His
            115                 120                 125

Lys Asn Asn Lys Ser Trp Met Glu Ser Glu Phe Arg Val Tyr Ser Ser
        130                 135                 140

Ala Asn Asn Cys Thr Phe Glu Tyr Val Ser Gln Pro Phe Leu Met Asp
145                 150                 155                 160

Leu Glu Gly Lys Gln Gly Asn Phe Lys Asn Leu Arg Glu Phe Val Phe
                165                 170                 175

Lys Asn Ile Asp Gly Tyr Phe Lys Ile Tyr Ser Lys His Thr Pro Ile
            180                 185                 190

Asn Leu Val Arg Asp Leu Pro Gln Gly Phe Ser Ala Leu Glu Pro Leu
            195                 200                 205

Val Asp Leu Pro Ile Gly Ile Asn Ile Thr Arg Phe Gln Thr Leu Leu
        210                 215                 220

Ala Leu His Arg Ser Tyr Leu Thr Pro Gly Asp Ser Ser Ser Gly Trp
225                 230                 235                 240

Thr Ala Gly Ala Ala Ala Tyr Tyr Val Gly Tyr Leu Gln Pro Arg Thr
                245                 250                 255

Phe Leu Leu Lys Tyr Asn Glu Asn Gly Thr Ile Thr Asp Ala Val Asp
            260                 265                 270

Cys Ala Leu Asp Pro Leu Ser Glu Thr Lys Cys Thr Leu Lys Ser Phe
            275                 280                 285

Thr Val Glu Lys Gly Ile Tyr Gln Thr Ser Asn Phe Arg Val Gln Pro
        290                 295                 300

Thr Glu Ser Ile Val Arg Phe Pro Asn Ile Thr Asn Leu Cys Pro Phe
305                 310                 315                 320

Gly Glu Val Phe Asn Ala Thr Arg Phe Ala Ser Val Tyr Ala Trp Asn
                325                 330                 335

Arg Lys Arg Ile Ser Asn Cys Val Ala Asp Tyr Ser Val Leu Tyr Asn
            340                 345                 350

Ser Ala Ser Phe Ser Thr Phe Lys Cys Tyr Gly Val Ser Pro Thr Lys
            355                 360                 365

Leu Asn Asp Leu Cys Phe Thr Asn Val Tyr Ala Asp Ser Phe Val Ile
        370                 375                 380

Arg Gly Asp Glu Val Arg Gln Ile Ala Pro Gly Gln Thr Gly Lys Ile
385                 390                 395                 400

Ala Asp Tyr Asn Tyr Lys Leu Pro Asp Asp Phe Thr Gly Cys Val Ile
                405                 410                 415

Ala Trp Asn Ser Asn Asn Leu Asp Ser Lys Val Gly Gly Asn Tyr Asn
            420                 425                 430

Tyr Leu Tyr Arg Leu Phe Arg Lys Ser Asn Leu Lys Pro Phe Glu Arg
            435                 440                 445

Asp Ile Ser Thr Glu Ile Tyr Gln Ala Gly Ser Thr Pro Cys Asn Gly
        450                 455                 460

Val Glu Gly Phe Asn Cys Tyr Phe Pro Leu Gln Ser Tyr Gly Phe Gln
465                 470                 475                 480

Pro Thr Tyr Gly Val Gly Tyr Gln Pro Tyr Arg Val Val Val Leu Ser
                485                 490                 495
```

-continued

```
Phe Glu Leu Leu His Ala Pro Ala Thr Val Cys Gly Pro Lys Lys Ser
            500                     505                 510

Thr Asn Leu Val Lys Asn Lys Cys Val Asn Phe Asn Phe Asn Gly Leu
            515                 520                 525

Thr Gly Thr Gly Val Leu Thr Glu Ser Asn Lys Lys Phe Leu Pro Phe
            530                 535                 540

Gln Gln Phe Gly Arg Asp Ile Asp Asp Thr Thr Asp Ala Val Arg Asp
545                 550                 555                 560

Pro Gln Thr Leu Glu Ile Leu Asp Ile Thr Pro Cys Ser Phe Gly Gly
                565                 570                 575

Val Ser Val Ile Thr Pro Gly Thr Asn Thr Ser Asn Gln Val Ala Val
            580                 585                 590

Leu Tyr Gln Gly Val Asn Cys Thr Glu Val Pro Val Ala Ile His Ala
            595                 600                 605

Asp Gln Leu Thr Pro Thr Trp Arg Val Tyr Ser Thr Gly Ser Asn Val
            610                 615                 620

Phe Gln Thr Arg Ala Gly Cys Leu Ile Gly Ala Glu His Val Asn Asn
625                 630                 635                 640

Ser Tyr Glu Cys Asp Ile Pro Ile Gly Ala Gly Ile Cys Ala Ser Tyr
                645                 650                 655

Gln Thr Gln Thr Asn Ser His Arg Ala Ala Ala Ser Val Ala Ser Gln
            660                 665                 670

Ser Ile Ile Ala Tyr Thr Met Ser Leu Gly Ala Glu Asn Ser Val Ala
            675                 680                 685

Tyr Ser Asn Asn Ser Ile Ala Ile Pro Ile Asn Phe Thr Ile Ser Val
            690                 695                 700

Thr Thr Glu Ile Leu Pro Val Ser Met Thr Lys Thr Ser Val Asp Cys
705                 710                 715                 720

Thr Met Tyr Ile Cys Gly Asp Ser Thr Glu Cys Ser Asn Leu Leu Leu
                725                 730                 735

Gln Tyr Gly Ser Phe Cys Thr Gln Leu Asn Arg Ala Leu Thr Gly Ile
            740                 745                 750

Ala Val Glu Gln Asp Lys Asn Thr Gln Glu Val Phe Ala Gln Val Lys
            755                 760                 765

Gln Ile Tyr Lys Thr Pro Pro Ile Lys Asp Phe Gly Gly Phe Asn Phe
            770                 775                 780

Ser Gln Ile Leu Pro Asp Pro Ser Lys Pro Ser Lys Arg Ser Pro Ile
785                 790                 795                 800

Glu Asp Leu Leu Phe Asn Lys Val Thr Leu Ala Asp Ala Gly Phe Ile
                805                 810                 815

Lys Gln Tyr Gly Asp Cys Leu Gly Asp Ile Ala Ala Arg Asp Leu Ile
                820                 825                 830

Cys Ala Gln Lys Phe Asn Gly Leu Thr Val Leu Pro Pro Leu Leu Thr
            835                 840                 845

Asp Glu Met Ile Ala Gln Tyr Thr Ser Ala Leu Leu Ala Gly Thr Ile
            850                 855                 860

Thr Ser Gly Trp Thr Phe Gly Ala Gly Pro Ala Leu Gln Ile Pro Phe
865                 870                 875                 880

Pro Met Gln Met Ala Tyr Arg Phe Asn Gly Ile Gly Val Thr Gln Asn
                885                 890                 895

Val Leu Tyr Glu Asn Gln Lys Leu Ile Ala Asn Gln Phe Asn Ser Ala
            900                 905                 910
```

```
Ile Gly Lys Ile Gln Asp Ser Leu Ser Ser Thr Pro Ser Ala Leu Gly
        915                 920                 925

Lys Leu Gln Asp Val Val Asn Gln Asn Ala Gln Ala Leu Asn Thr Leu
        930                 935                 940

Val Lys Gln Leu Ser Ser Asn Phe Gly Ala Ile Ser Ser Val Leu Asn
945                 950                 955                 960

Asp Ile Leu Ala Arg Leu Asp Pro Pro Glu Ala Glu Val Gln Ile Asp
                965                 970                 975

Arg Leu Ile Thr Gly Arg Leu Gln Ser Leu Gln Thr Tyr Val Thr Gln
                980                 985                 990

Gln Leu Ile Arg Ala Ala Glu Ile  Arg Ala Ser Ala Asn  Leu Ala Ala
        995                 1000                1005

Thr Lys  Met Ser Glu Cys Val  Leu Gly Gln Ser Lys  Arg Val Asp
        1010                1015                1020

Phe Cys  Gly Lys Gly Tyr His  Leu Met Ser Phe Pro  Gln Ser Ala
        1025                1030                1035

Pro His  Gly Val Val Phe Leu  His Val Thr Tyr Val  Pro Ala Gln
        1040                1045                1050

Glu Lys  Asn Phe Thr Thr Ala  Pro Ala Ile Cys His  Asp Gly Lys
        1055                1060                1065

Ala His  Phe Pro Arg Glu Gly  Val Phe Val Ser Asn  Gly Thr His
        1070                1075                1080

Trp Phe  Val Thr Gln Arg Asn  Phe Tyr Glu Pro Gln  Ile Ile Thr
        1085                1090                1095

Thr His  Asn Thr Phe Val Ser  Gly Asn Cys Asp Val  Val Ile Gly
        1100                1105                1110

Ile Val  Asn Asn Thr Val Tyr  Asp Pro Leu Gln Pro  Glu Leu Asp
        1115                1120                1125

Ser Phe  Lys Glu Glu Leu Asp  Lys Tyr Phe Lys Asn  His Thr Ser
        1130                1135                1140

Pro Asp  Val Asp Leu Gly Asp  Ile Ser Gly Ile Asn  Ala Ser Val
        1145                1150                1155

Val Asn  Ile Gln Lys Glu Ile  Asp Arg Leu Asn Glu  Val Ala Lys
        1160                1165                1170

Asn Leu  Asn Glu Ser Leu Ile  Asp Leu Gln Glu Leu  Gly Lys Tyr
        1175                1180                1185

Glu Gln  Tyr Ile Lys Trp Pro
        1190                1195

<210> SEQ ID NO 8
<211> LENGTH: 1198
<212> TYPE: PRT
<213> ORGANISM: SARS-CoV-2

<400> SEQUENCE: 8

Val Asn Phe Thr Thr Arg Thr Gln Leu Pro Pro Ala Tyr Thr Asn Ser
1               5                   10                  15

Phe Thr Arg Gly Val Tyr Tyr Pro Asp Lys Val Phe Arg Ser Ser Val
                20                  25                  30

Leu His Ser Thr Gln Asp Leu Phe Leu Pro Phe Phe Ser Asn Val Thr
            35                  40                  45

Trp Phe His Ala Ile His Val Ser Gly Thr Asn Gly Thr Lys Arg Phe
        50                  55                  60

Ala Asn Pro Val Leu Pro Phe Asn Asp Gly Val Tyr Phe Ala Ser Thr
65                  70                  75                  80
```

```
Glu Lys Ser Asn Ile Ile Arg Gly Trp Ile Phe Gly Thr Thr Leu Asp
            85              90              95

Ser Lys Thr Gln Ser Leu Leu Ile Val Asn Asn Ala Thr Asn Val Val
            100             105             110

Ile Lys Val Cys Glu Phe Gln Phe Cys Asn Asp Pro Phe Leu Gly Val
            115             120             125

Tyr Tyr His Lys Asn Asn Lys Ser Trp Met Glu Ser Glu Phe Arg Val
        130             135             140

Tyr Ser Ser Ala Asn Asn Cys Thr Phe Glu Tyr Val Ser Gln Pro Phe
145             150             155             160

Leu Met Asp Leu Glu Gly Lys Gln Gly Asn Phe Lys Asn Leu Arg Glu
            165             170             175

Phe Val Phe Lys Asn Ile Asp Gly Tyr Phe Lys Ile Tyr Ser Lys His
            180             185             190

Thr Pro Ile Asn Leu Val Arg Gly Leu Pro Gln Gly Phe Ser Ala Leu
            195             200             205

Glu Pro Leu Val Asp Leu Pro Ile Gly Ile Asn Ile Thr Arg Phe Gln
            210             215             220

Thr Leu Leu Ala Leu His Ile Ser Tyr Leu Thr Pro Gly Asp Ser Ser
225             230             235             240

Ser Gly Trp Thr Ala Gly Ala Ala Ala Tyr Tyr Val Gly Tyr Leu Gln
            245             250             255

Pro Arg Thr Phe Leu Leu Lys Tyr Asn Glu Asn Gly Thr Ile Thr Asp
            260             265             270

Ala Val Asp Cys Ala Leu Asp Pro Leu Ser Glu Thr Lys Cys Thr Leu
            275             280             285

Lys Ser Phe Thr Val Glu Lys Gly Ile Tyr Gln Thr Ser Asn Phe Arg
        290             295             300

Val Gln Pro Thr Glu Ser Ile Val Arg Phe Pro Asn Ile Thr Asn Leu
305             310             315             320

Cys Pro Phe Gly Glu Val Phe Asn Ala Thr Arg Phe Ala Ser Val Tyr
            325             330             335

Ala Trp Asn Arg Lys Arg Ile Ser Asn Cys Val Ala Asp Tyr Ser Val
            340             345             350

Leu Tyr Asn Ser Ala Ser Phe Ser Thr Phe Lys Cys Tyr Gly Val Ser
            355             360             365

Pro Thr Lys Leu Asn Asp Leu Cys Phe Thr Asn Val Tyr Ala Asp Ser
        370             375             380

Phe Val Ile Arg Gly Asp Glu Val Arg Gln Ile Ala Pro Gly Gln Thr
385             390             395             400

Gly Asn Ile Ala Asp Tyr Asn Tyr Lys Leu Pro Asp Asp Phe Thr Gly
            405             410             415

Cys Val Ile Ala Trp Asn Ser Asn Asn Leu Asp Ser Lys Val Gly Gly
            420             425             430

Asn Tyr Asn Tyr Leu Tyr Arg Leu Phe Arg Lys Ser Asn Leu Lys Pro
        435             440             445

Phe Glu Arg Asp Ile Ser Thr Glu Ile Tyr Gln Ala Gly Ser Thr Pro
        450             455             460

Cys Asn Gly Val Lys Gly Phe Asn Cys Tyr Phe Pro Leu Gln Ser Tyr
465             470             475             480

Gly Phe Gln Pro Thr Tyr Gly Val Gly Tyr Gln Pro Tyr Arg Val Val
            485             490             495
```

-continued

```
Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe Asn Phe
            515                 520                 525

Asn Gly Leu Thr Gly Thr Gly Val Leu Thr Glu Ser Asn Lys Lys Phe
            530                 535                 540

Leu Pro Phe Gln Gln Phe Gly Arg Asp Ile Ala Asp Thr Thr Asp Ala
545                 550                 555                 560

Val Arg Asp Pro Gln Thr Leu Glu Ile Leu Asp Ile Thr Pro Cys Ser
                565                 570                 575

Phe Gly Gly Val Ser Val Ile Thr Pro Gly Thr Asn Thr Ser Asn Gln
                580                 585                 590

Val Ala Val Leu Tyr Gln Gly Val Asn Cys Thr Glu Val Pro Val Ala
                595                 600                 605

Ile His Ala Asp Gln Leu Thr Pro Thr Trp Arg Val Tyr Ser Thr Gly
            610                 615                 620

Ser Asn Val Phe Gln Thr Arg Ala Gly Cys Leu Ile Gly Ala Glu His
625                 630                 635                 640

Val Asn Asn Ser Tyr Glu Cys Asp Ile Pro Ile Gly Ala Gly Ile Cys
                645                 650                 655

Ala Ser Tyr Gln Thr Gln Thr Asn Ser Pro Arg Ala Ala Ala Ser Val
                660                 665                 670

Ala Ser Gln Ser Ile Ile Ala Tyr Thr Met Ser Leu Gly Val Glu Asn
                675                 680                 685

Ser Val Ala Tyr Ser Asn Asn Ser Ile Ala Ile Pro Thr Asn Phe Thr
            690                 695                 700

Ile Ser Val Thr Thr Glu Ile Leu Pro Val Ser Met Thr Lys Thr Ser
705                 710                 715                 720

Val Asp Cys Thr Met Tyr Ile Cys Gly Asp Ser Thr Glu Cys Ser Asn
                725                 730                 735

Leu Leu Leu Gln Tyr Gly Ser Phe Cys Thr Gln Leu Asn Arg Ala Leu
            740                 745                 750

Thr Gly Ile Ala Val Glu Gln Asp Lys Asn Thr Gln Glu Val Phe Ala
            755                 760                 765

Gln Val Lys Gln Ile Tyr Lys Thr Pro Pro Ile Lys Asp Phe Gly Gly
            770                 775                 780

Phe Asn Phe Ser Gln Ile Leu Pro Asp Pro Ser Lys Pro Ser Lys Arg
785                 790                 795                 800

Ser Pro Ile Glu Asp Leu Leu Phe Asn Lys Val Thr Leu Ala Asp Ala
                805                 810                 815

Gly Phe Ile Lys Gln Tyr Gly Asp Cys Leu Gly Asp Ile Ala Ala Arg
                820                 825                 830

Asp Leu Ile Cys Ala Gln Lys Phe Asn Gly Leu Thr Val Leu Pro Pro
            835                 840                 845

Leu Leu Thr Asp Glu Met Ile Ala Gln Tyr Thr Ser Ala Leu Leu Ala
            850                 855                 860

Gly Thr Ile Thr Ser Gly Trp Thr Phe Gly Ala Gly Pro Ala Leu Gln
865                 870                 875                 880

Ile Pro Phe Pro Met Gln Met Ala Tyr Arg Phe Asn Gly Ile Gly Val
                885                 890                 895

Thr Gln Asn Val Leu Tyr Glu Asn Gln Lys Leu Ile Ala Asn Gln Phe
                900                 905                 910

Asn Ser Ala Ile Gly Lys Ile Gln Asp Ser Leu Ser Ser Thr Pro Ser
```

-continued

```
            915                 920                 925
Ala Leu Gly Lys Leu Gln Asp Val Val Asn Gln Asn Ala Gln Ala Leu
    930                 935                 940
Asn Thr Leu Val Lys Gln Leu Ser Ser Asn Phe Gly Ala Ile Ser Ser
945                 950                 955                 960
Val Leu Asn Asp Ile Leu Ser Arg Leu Asp Pro Pro Glu Ala Glu Val
                965                 970                 975
Gln Ile Asp Arg Leu Ile Thr Gly Arg Leu Gln Ser Leu Gln Thr Tyr
            980                 985                 990
Val Thr Gln Gln Leu Ile Arg Ala  Ala Glu Ile Arg Ala  Ser Ala Asn
        995                 1000                1005
Leu Ala  Ala Thr Lys Met Ser  Glu Cys Val Leu Gly  Gln Ser Lys
    1010                1015                1020
Arg Val  Asp Phe Cys Gly Lys  Gly Tyr His Leu Met  Ser Phe Pro
    1025                1030                1035
Gln Ser  Ala Pro His Gly Val  Val Phe Leu His Val  Thr Tyr Val
    1040                1045                1050
Pro Ala  Gln Glu Lys Asn Phe  Thr Thr Ala Pro Ala  Ile Cys His
    1055                1060                1065
Asp Gly  Lys Ala His Phe Pro  Arg Glu Gly Val Phe  Val Ser Asn
    1070                1075                1080
Gly Thr  His Trp Phe Val Thr  Gln Arg Asn Phe Tyr  Glu Pro Gln
    1085                1090                1095
Ile Ile  Thr Thr Asp Asn Thr  Phe Val Ser Gly Asn  Cys Asp Val
    1100                1105                1110
Val Ile  Gly Ile Val Asn Asn  Thr Val Tyr Asp Pro  Leu Gln Pro
    1115                1120                1125
Glu Leu  Asp Ser Phe Lys Glu  Glu Leu Asp Lys Tyr  Phe Lys Asn
    1130                1135                1140
His Thr  Ser Pro Asp Val Asp  Leu Gly Asp Ile Ser  Gly Ile Asn
    1145                1150                1155
Ala Ser  Val Val Asn Ile Gln  Lys Glu Ile Asp Arg  Leu Asn Glu
    1160                1165                1170
Val Ala  Lys Asn Leu Asn Glu  Ser Leu Ile Asp Leu  Gln Glu Leu
    1175                1180                1185
Gly Lys  Tyr Glu Gln Tyr Ile  Lys Trp Pro
    1190                1195
```

```
<210> SEQ ID NO 9
<211> LENGTH: 1198
<212> TYPE: PRT
<213> ORGANISM: SARS-CoV-2

<400> SEQUENCE: 9

Val Asn Phe Thr Asn Arg Thr Gln Leu Pro Ser Ala Tyr Thr Asn Ser
1               5                   10                  15
Phe Thr Arg Gly Val Tyr Tyr Pro Asp Lys Val Phe Arg Ser Ser Val
                20                  25                  30
Leu His Ser Thr Gln Asp Leu Phe Leu Pro Phe Phe Ser Asn Val Thr
            35                  40                  45
Trp Phe His Ala Ile His Val Ser Gly Thr Asn Gly Thr Lys Arg Phe
        50                  55                  60
Asp Asn Pro Val Leu Pro Phe Asn Asp Gly Val Tyr Phe Ala Ser Thr
65                  70                  75                  80
```

-continued

```
Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Tyr Pro Phe Leu Gly Val
        115                 120                 125

Tyr Tyr His Lys Asn Asn Lys Ser Trp Met Glu Ser Glu Phe Arg Val
    130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Ser Glu
                165                 170                 175

Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
        195                 200                 205

Glu Pro Leu Val Asp Leu Pro Ile Gly Ile Asn Ile Thr Arg Phe Gln
    210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
                245                 250                 255

Pro Arg Thr Phe Leu Leu Lys Tyr Asn Glu Asn Gly Thr Ile Thr Asp
                260                 265                 270

Ala Val Asp Cys Ala Leu Asp Pro Leu Ser Glu Thr Lys Cys Thr Leu
            275                 280                 285

Lys Ser Phe Thr Val Glu Lys Gly Ile Tyr Gln Thr Ser Asn Phe Arg
    290                 295                 300

Val Gln Pro Thr Glu Ser Ile Val Arg Phe Pro Asn Ile Thr Asn Leu
305                 310                 315                 320

Cys Pro Phe Gly Glu Val Phe Asn Ala Thr Arg Phe Ala Ser Val Tyr
                325                 330                 335

Ala Trp Asn Arg Lys Arg Ile Ser Asn Cys Val Ala Asp Tyr Ser Val
                340                 345                 350

Leu Tyr Asn Ser Ala Ser Phe Ser Thr Phe Lys Cys Tyr Gly Val Ser
            355                 360                 365

Pro Thr Lys Leu Asn Asp Leu Cys Phe Thr Asn Val Tyr Ala Asp Ser
    370                 375                 380

Phe Val Ile Arg Gly Asp Glu Val Arg Gln Ile Ala Pro Gly Gln Thr
385                 390                 395                 400

Gly Thr Ile Ala Asp Tyr Asn Tyr Lys Leu Pro Asp Asp Phe Thr Gly
                405                 410                 415

Cys Val Ile Ala Trp Asn Ser Asn Asn Leu Asp Ser Lys Val Gly Gly
            420                 425                 430

Asn Tyr Asn Tyr Leu Tyr Arg Leu Phe Arg Lys Ser Asn Leu Lys Pro
        435                 440                 445

Phe Glu Arg Asp Ile Ser Thr Glu Ile Tyr Gln Ala Gly Ser Thr Pro
    450                 455                 460

Cys Asn Gly Val Lys Gly Phe Asn Cys Tyr Phe Pro Leu Gln Ser Tyr
465                 470                 475                 480

Gly Phe Gln Pro Thr Tyr Gly Val Gly Tyr Gln Pro Tyr Arg Val Val
                485                 490                 495

Val Leu Ser Phe Glu Leu Leu His Ala Pro Ala Thr Val Cys Gly Pro
```

-continued

```
                500                 505                 510

Lys Lys Ser Thr Asn Leu Val Lys Asn Lys Cys Val Asn Phe Asn Phe
            515                 520                 525

Asn Gly Leu Thr Gly Thr Gly Val Leu Thr Glu Ser Asn Lys Lys Phe
            530                 535                 540

Leu Pro Phe Gln Gln Phe Gly Arg Asp Ile Ala Asp Thr Thr Asp Ala
545                 550                 555                 560

Val Arg Asp Pro Gln Thr Leu Glu Ile Leu Asp Ile Thr Pro Cys Ser
                565                 570                 575

Phe Gly Gly Val Ser Val Ile Thr Pro Gly Thr Asn Thr Ser Asn Gln
                580                 585                 590

Val Ala Val Leu Tyr Gln Gly Val Asn Cys Thr Glu Val Pro Val Ala
            595                 600                 605

Ile His Ala Asp Gln Leu Thr Pro Thr Trp Arg Val Tyr Ser Thr Gly
            610                 615                 620

Ser Asn Val Phe Gln Thr Arg Ala Gly Cys Leu Ile Gly Ala Glu Tyr
625                 630                 635                 640

Val Asn Asn Ser Tyr Glu Cys Asp Ile Pro Ile Gly Ala Gly Ile Cys
                645                 650                 655

Ala Ser Tyr Gln Thr Gln Thr Asn Ser Pro Arg Ala Ala Ala Ser Val
                660                 665                 670

Ala Ser Gln Ser Ile Ile Ala Tyr Thr Met Ser Leu Gly Ala Glu Asn
            675                 680                 685

Ser Val Ala Tyr Ser Asn Asn Ser Ile Ala Ile Pro Thr Asn Phe Thr
            690                 695                 700

Ile Ser Val Thr Thr Glu Ile Leu Pro Val Ser Met Thr Lys Thr Ser
705                 710                 715                 720

Val Asp Cys Thr Met Tyr Ile Cys Gly Asp Ser Thr Glu Cys Ser Asn
                725                 730                 735

Leu Leu Leu Gln Tyr Gly Ser Phe Cys Thr Gln Leu Asn Arg Ala Leu
                740                 745                 750

Thr Gly Ile Ala Val Glu Gln Asp Lys Asn Thr Gln Glu Val Phe Ala
            755                 760                 765

Gln Val Lys Gln Ile Tyr Lys Thr Pro Pro Ile Lys Asp Phe Gly Gly
            770                 775                 780

Phe Asn Phe Ser Gln Ile Leu Pro Asp Pro Ser Lys Pro Ser Lys Arg
785                 790                 795                 800

Ser Pro Ile Glu Asp Leu Leu Phe Asn Lys Val Thr Leu Ala Asp Ala
                805                 810                 815

Gly Phe Ile Lys Gln Tyr Gly Asp Cys Leu Gly Asp Ile Ala Ala Arg
            820                 825                 830

Asp Leu Ile Cys Ala Gln Lys Phe Asn Gly Leu Thr Val Leu Pro Pro
            835                 840                 845

Leu Leu Thr Asp Glu Met Ile Ala Gln Tyr Thr Ser Ala Leu Leu Ala
            850                 855                 860

Gly Thr Ile Thr Ser Gly Trp Thr Phe Gly Ala Gly Pro Ala Leu Gln
865                 870                 875                 880

Ile Pro Phe Pro Met Gln Met Ala Tyr Arg Phe Asn Gly Ile Gly Val
                885                 890                 895

Thr Gln Asn Val Leu Tyr Glu Asn Gln Lys Leu Ile Ala Asn Gln Phe
                900                 905                 910

Asn Ser Ala Ile Gly Lys Ile Gln Asp Ser Leu Ser Ser Thr Pro Ser
            915                 920                 925
```

-continued

```
Ala Leu Gly Lys Leu Gln Asp Val Val Asn Gln Asn Ala Gln Ala Leu
    930             935             940

Asn Thr Leu Val Lys Gln Leu Ser Ser Asn Phe Gly Ala Ile Ser Ser
945             950             955             960

Val Leu Asn Asp Ile Leu Ser Arg Leu Asp Pro Pro Glu Ala Glu Val
            965             970             975

Gln Ile Asp Arg Leu Ile Thr Gly Arg Leu Gln Ser Leu Gln Thr Tyr
            980             985             990

Val Thr Gln Gln Leu Ile Arg Ala  Ala Glu Ile Arg Ala  Ser Ala Asn
        995             1000            1005

Leu Ala  Ala Ile Lys Met Ser  Glu Cys Val Leu Gly  Gln Ser Lys
    1010            1015            1020

Arg Val  Asp Phe Cys Gly Lys  Gly Tyr His Leu Met  Ser Phe Pro
    1025            1030            1035

Gln Ser  Ala Pro His Gly Val  Val Phe Leu His Val  Thr Tyr Val
    1040            1045            1050

Pro Ala  Gln Glu Lys Asn Phe  Thr Thr Ala Pro Ala  Ile Cys His
    1055            1060            1065

Asp Gly  Lys Ala His Phe Pro  Arg Glu Gly Val Phe  Val Ser Asn
    1070            1075            1080

Gly Thr  His Trp Phe Val Thr  Gln Arg Asn Phe Tyr  Glu Pro Gln
    1085            1090            1095

Ile Ile  Thr Thr Asp Asn Thr  Phe Val Ser Gly Asn  Cys Asp Val
    1100            1105            1110

Val Ile  Gly Ile Val Asn Asn  Thr Val Tyr Asp Pro  Leu Gln Pro
    1115            1120            1125

Glu Leu  Asp Ser Phe Lys Glu  Glu Leu Asp Lys Tyr  Phe Lys Asn
    1130            1135            1140

His Thr  Ser Pro Asp Val Asp  Leu Gly Asp Ile Ser  Gly Ile Asn
    1145            1150            1155

Ala Ser  Phe Val Asn Ile Gln  Lys Glu Ile Asp Arg  Leu Asn Glu
    1160            1165            1170

Val Ala  Lys Asn Leu Asn Glu  Ser Leu Ile Asp Leu  Gln Glu Leu
    1175            1180            1185

Gly Lys  Tyr Glu Gln Tyr Ile  Lys Trp Pro
    1190            1195

<210> SEQ ID NO 10
<211> LENGTH: 1196
<212> TYPE: PRT
<213> ORGANISM: SARS-CoV-2

<400> SEQUENCE: 10

Val Asn Leu Arg Thr Arg Thr Gln Leu Pro Pro Ala Tyr Thr Asn Ser
1               5               10              15

Phe Thr Arg Gly Val Tyr Tyr Pro Asp Lys Val Phe Arg Ser Ser Val
            20              25              30

Leu His Ser Thr Gln Asp Leu Phe Leu Pro Phe Phe Ser Asn Val Thr
        35              40              45

Trp Phe His Ala Ile His Val Ser Gly Thr Asn Gly Thr Lys Arg Phe
    50              55              60

Asp Asn Pro Val Leu Pro Phe Asn Asp Gly Val Tyr Phe Ala Ser Thr
65              70              75              80

Glu Lys Ser Asn Ile Ile Arg Gly Trp Ile Phe Gly Thr Thr Leu Asp
```

-continued

```
                    85              90              95

Ser Lys Thr Gln Ser Leu Leu Ile Val Asn Asn Ala Thr Asn Val Val
            100             105             110

Ile Lys Val Cys Glu Phe Gln Phe Cys Asn Asp Pro Phe Leu Asp Val
            115             120             125

Tyr Tyr His Lys Asn Asn Lys Ser Trp Met Glu Ser Gly Val Tyr Ser
    130             135             140

Ser Ala Asn Asn Cys Thr Phe Glu Tyr Val Ser Gln Pro Phe Leu Met
145             150             155             160

Asp Leu Glu Gly Lys Gln Gly Asn Phe Lys Asn Leu Arg Glu Phe Val
                165             170             175

Phe Lys Asn Ile Asp Gly Tyr Phe Lys Ile Tyr Ser Lys His Thr Pro
            180             185             190

Ile Asn Leu Val Arg Asp Leu Pro Gln Gly Phe Ser Ala Leu Glu Pro
            195             200             205

Leu Val Asp Leu Pro Ile Gly Ile Asn Ile Thr Arg Phe Gln Thr Leu
    210             215             220

Leu Ala Leu His Arg Ser Tyr Leu Thr Pro Gly Asp Ser Ser Ser Gly
225             230             235             240

Trp Thr Ala Gly Ala Ala Ala Tyr Tyr Val Gly Tyr Leu Gln Pro Arg
                245             250             255

Thr Phe Leu Leu Lys Tyr Asn Glu Asn Gly Thr Ile Thr Asp Ala Val
            260             265             270

Asp Cys Ala Leu Asp Pro Leu Ser Glu Thr Lys Cys Thr Leu Lys Ser
            275             280             285

Phe Thr Val Glu Lys Gly Ile Tyr Gln Thr Ser Asn Phe Arg Val Gln
    290             295             300

Pro Thr Glu Ser Ile Val Arg Phe Pro Asn Ile Thr Asn Leu Cys Pro
305             310             315             320

Phe Gly Glu Val Phe Asn Ala Thr Arg Phe Ala Ser Val Tyr Ala Trp
                325             330             335

Asn Arg Lys Arg Ile Ser Asn Cys Val Ala Asp Tyr Ser Val Leu Tyr
            340             345             350

Asn Ser Ala Ser Phe Ser Thr Phe Lys Cys Tyr Gly Val Ser Pro Thr
            355             360             365

Lys Leu Asn Asp Leu Cys Phe Thr Asn Val Tyr Ala Asp Ser Phe Val
    370             375             380

Ile Arg Gly Asp Glu Val Arg Gln Ile Ala Pro Gly Gln Thr Gly Lys
385             390             395             400

Ile Ala Asp Tyr Asn Tyr Lys Leu Pro Asp Asp Phe Thr Gly Cys Val
                405             410             415

Ile Ala Trp Asn Ser Asn Asn Leu Asp Ser Lys Val Gly Gly Asn Tyr
            420             425             430

Asn Tyr Arg Tyr Arg Leu Phe Arg Lys Ser Asn Leu Lys Pro Phe Glu
            435             440             445

Arg Asp Ile Ser Thr Glu Ile Tyr Gln Ala Gly Ser Lys Pro Cys Asn
    450             455             460

Gly Val Glu Gly Phe Asn Cys Tyr Phe Pro Leu Gln Ser Tyr Gly Phe
465             470             475             480

Gln Pro Thr Asn Gly Val Gly Tyr Gln Pro Tyr Arg Val Val Val Leu
                485             490             495

Ser Phe Glu Leu Leu His Ala Pro Ala Thr Val Cys Gly Pro Lys Lys
            500             505             510
```

-continued

```
Ser Thr Asn Leu Val Lys Asn Lys Cys Val Asn Phe Asn Phe Asn Gly
    515                 520                 525

Leu Thr Gly Thr Gly Val Leu Thr Glu Ser Asn Lys Lys Phe Leu Pro
    530                 535                 540

Phe Gln Gln Phe Gly Arg Asp Ile Ala Asp Thr Thr Asp Ala Val Arg
545                 550                 555                 560

Asp Pro Gln Thr Leu Glu Ile Leu Asp Ile Thr Pro Cys Ser Phe Gly
                565                 570                 575

Gly Val Ser Val Ile Thr Pro Gly Thr Asn Thr Ser Asn Gln Val Ala
                580                 585                 590

Val Leu Tyr Gln Gly Val Asn Cys Thr Glu Val Pro Val Ala Ile His
    595                 600                 605

Ala Asp Gln Leu Thr Pro Thr Trp Arg Val Tyr Ser Thr Gly Ser Asn
    610                 615                 620

Val Phe Gln Thr Arg Ala Gly Cys Leu Ile Gly Ala Glu His Val Asn
625                 630                 635                 640

Asn Ser Tyr Glu Cys Asp Ile Pro Ile Gly Ala Gly Ile Cys Ala Ser
                645                 650                 655

Tyr Gln Thr Gln Thr Asn Ser Arg Arg Ala Ala Ala Ser Val Ala Ser
                660                 665                 670

Gln Ser Ile Ile Ala Tyr Thr Met Ser Leu Gly Ala Glu Asn Ser Val
    675                 680                 685

Ala Tyr Ser Asn Asn Ser Ile Ala Ile Pro Thr Asn Phe Thr Ile Ser
    690                 695                 700

Val Thr Thr Glu Ile Leu Pro Val Ser Met Thr Lys Thr Ser Val Asp
705                 710                 715                 720

Cys Thr Met Tyr Ile Cys Gly Asp Ser Thr Glu Cys Ser Asn Leu Leu
                725                 730                 735

Leu Gln Tyr Gly Ser Phe Cys Thr Gln Leu Asn Arg Ala Leu Thr Gly
                740                 745                 750

Ile Ala Val Glu Gln Asp Lys Asn Thr Gln Glu Val Phe Ala Gln Val
    755                 760                 765

Lys Gln Ile Tyr Lys Thr Pro Pro Ile Lys Asp Phe Gly Gly Phe Asn
    770                 775                 780

Phe Ser Gln Ile Leu Pro Asp Pro Ser Lys Pro Ser Lys Arg Ser Pro
785                 790                 795                 800

Ile Glu Asp Leu Leu Phe Asn Lys Val Thr Leu Ala Asp Ala Gly Phe
                805                 810                 815

Ile Lys Gln Tyr Gly Asp Cys Leu Gly Asp Ile Ala Ala Arg Asp Leu
                820                 825                 830

Ile Cys Ala Gln Lys Phe Asn Gly Leu Thr Val Leu Pro Pro Leu Leu
    835                 840                 845

Thr Asp Glu Met Ile Ala Gln Tyr Thr Ser Ala Leu Leu Ala Gly Thr
    850                 855                 860

Ile Thr Ser Gly Trp Thr Phe Gly Ala Gly Pro Ala Leu Gln Ile Pro
865                 870                 875                 880

Phe Pro Met Gln Met Ala Tyr Arg Phe Asn Gly Ile Gly Val Thr Gln
                885                 890                 895

Asn Val Leu Tyr Glu Asn Gln Lys Leu Ile Ala Asn Gln Phe Asn Ser
                900                 905                 910

Ala Ile Gly Lys Ile Gln Asp Ser Leu Ser Ser Thr Pro Ser Ala Leu
    915                 920                 925
```

-continued

```
Gly Lys Leu Gln Asn Val Val Asn Gln Asn Ala Gln Ala Leu Asn Thr
    930                 935                 940

Leu Val Lys Gln Leu Ser Ser Asn Phe Gly Ala Ile Ser Ser Val Leu
945                 950                 955                 960

Asn Asp Ile Leu Ser Arg Leu Asp Pro Pro Glu Ala Glu Val Gln Ile
                965                 970                 975

Asp Arg Leu Ile Thr Gly Arg Leu Gln Ser Leu Gln Thr Tyr Val Thr
                980                 985                 990

Gln Gln Leu Ile Arg Ala Ala Glu  Ile Arg Ala Ser Ala  Asn Leu Ala
        995                 1000                1005

Ala Thr  Lys Met Ser Glu Cys  Val Leu Gly Gln Ser  Lys Arg Val
    1010                1015                1020

Asp Phe  Cys Gly Lys Gly Tyr  His Leu Met Ser Phe  Pro Gln Ser
    1025                1030                1035

Ala Pro  His Gly Val Val Phe  Leu His Val Thr Tyr  Val Pro Ala
    1040                1045                1050

Gln Glu  Lys Asn Phe Thr Thr  Ala Pro Ala Ile Cys  His Asp Gly
    1055                1060                1065

Lys Ala  His Phe Pro Arg Glu  Gly Val Phe Val Ser  Asn Gly Thr
    1070                1075                1080

His Trp  Phe Val Thr Gln Arg  Asn Phe Tyr Glu Pro  Gln Ile Ile
    1085                1090                1095

Thr Thr  Asp Asn Thr Phe Val  Ser Gly Asn Cys Asp  Val Val Ile
    1100                1105                1110

Gly Ile  Val Asn Asn Thr Val  Tyr Asp Pro Leu Gln  Pro Glu Leu
    1115                1120                1125

Asp Ser  Phe Lys Glu Glu Leu  Asp Lys Tyr Phe Lys  Asn His Thr
    1130                1135                1140

Ser Pro  Asp Val Asp Leu Gly  Asp Ile Ser Gly Ile  Asn Ala Ser
    1145                1150                1155

Val Val  Asn Ile Gln Lys Glu  Ile Asp Arg Leu Asn  Glu Val Ala
    1160                1165                1170

Lys Asn  Leu Asn Glu Ser Leu  Ile Asp Leu Gln Glu  Leu Gly Lys
    1175                1180                1185

Tyr Glu  Gln Tyr Ile Lys Trp  Pro
    1190                1195

<210> SEQ ID NO 11
<211> LENGTH: 223
<212> TYPE: PRT
<213> ORGANISM: SARS-CoV-2
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
```

-continued

```
<400> SEQUENCE: 11

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Xaa Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Xaa Tyr Arg Leu Phe Arg Lys Ser Asn Leu Lys
    130                 135                 140

Pro Phe Glu Arg Asp Ile Ser Thr Glu Ile Tyr Gln Ala Gly Ser Xaa
145                 150                 155                 160

Pro Cys Asn Gly Val Xaa Gly Phe Asn Cys Tyr Phe Pro Leu Gln Ser
                165                 170                 175

Tyr Gly Phe Gln Pro Thr Xaa Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220
```